(12) United States Patent
Kawakami et al.

(10) Patent No.: US 10,559,760 B2
(45) Date of Patent: Feb. 11, 2020

(54) ORGANIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Sachiko Kawakami, Kanagawa (JP); Yusuke Takita, Kanagawa (JP); Tsunenori Suzuki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 200 days.

(21) Appl. No.: 15/700,532

(22) Filed: Sep. 11, 2017

(65) Prior Publication Data

US 2018/0076394 A1 Mar. 15, 2018

(30) Foreign Application Priority Data

Sep. 14, 2016 (JP) .................................. 2016-179489

(51) Int. Cl.
  *H01L 51/00* (2006.01)
  *C07D 307/77* (2006.01)
  *C07C 211/31* (2006.01)

(52) U.S. Cl.
  CPC ........ *H01L 51/0065* (2013.01); *C07D 307/77* (2013.01); *H01L 51/0061* (2013.01); *C07C 211/31* (2013.01)

(58) Field of Classification Search
  None
  See application file for complete search history.

(56) References Cited

U.S. PATENT DOCUMENTS

| 8,822,434 | B2 | 9/2014 | Liang et al. |
| 9,087,997 | B2 | 7/2015 | Yabunouchi |
| 9,093,649 | B2 | 7/2015 | Kawakami et al. |
| 9,303,053 | B2 | 4/2016 | Liang et al. |
| 9,526,739 | B2 | 12/2016 | Liang et al. |
| 9,586,924 | B2 | 3/2017 | Kawakami et al. |
| 2007/0037011 | A1 | 2/2007 | Nakashima et al. |

(Continued)

FOREIGN PATENT DOCUMENTS

| CN | 102046613 A | 5/2011 |
| CN | 105683173 A | 6/2016 |

(Continued)

OTHER PUBLICATIONS

International Search Report re Application No. PCT/IB2017/055296, dated Oct. 24, 2016.

(Continued)

*Primary Examiner* — Robert S Loewe
(74) *Attorney, Agent, or Firm* — Husch Blackwell LLP

(57) ABSTRACT

A novel organic compound is provided. In particular, a novel organic compound which can improve the element characteristics of a light-emitting element is provided. A novel light-emitting element with high emission efficiency, low driving voltage, and high reliability is provided. An organic compound including an amine skeleton and a benzo[b]naphtho[1,2-d]furan skeleton is provided. A light-emitting element including the organic compound is provided.

15 Claims, 32 Drawing Sheets

(56) References Cited

U.S. PATENT DOCUMENTS

| | | |
|---|---|---|
| 2007/0096639 A1 | 5/2007 | Nakashima et al. |
| 2007/0149784 A1 | 6/2007 | Murata et al. |
| 2007/0215867 A1 | 9/2007 | Kawakami et al. |
| 2007/0215889 A1 | 9/2007 | Kawakami et al. |
| 2008/0206598 A1 | 8/2008 | Ohsawa et al. |
| 2009/0284140 A1 | 11/2009 | Osaka et al. |
| 2010/0001636 A1 | 1/2010 | Yabunouchi |
| 2010/0245217 A1 | 9/2010 | Nomura et al. |
| 2010/0301744 A1 | 12/2010 | Osaka et al. |
| 2011/0168992 A1 | 7/2011 | Bae et al. |
| 2012/0161119 A1 | 6/2012 | Yabunouchi |
| 2012/0305898 A1 | 12/2012 | Okamoto |
| 2013/0105771 A1* | 5/2013 | Ryu ..................... C09K 11/06 257/40 |
| 2014/0183500 A1 | 7/2014 | Ikeda et al. |
| 2015/0031900 A1 | 1/2015 | Kawakami et al. |
| 2015/0060813 A1 | 3/2015 | Kawakami et al. |
| 2015/0318495 A1 | 11/2015 | Kawakami et al. |
| 2015/0329514 A1 | 11/2015 | Kawakami et al. |
| 2016/0079314 A1 | 3/2016 | Seo et al. |
| 2016/0166591 A1 | 6/2016 | Liang et al. |
| 2017/0040535 A1 | 2/2017 | Ogita et al. |
| 2017/0125689 A1 | 5/2017 | Lee et al. |
| 2017/0222156 A1 | 8/2017 | Kawakami et al. |
| 2017/0229648 A1 | 8/2017 | Kawakami et al. |

FOREIGN PATENT DOCUMENTS

| | | |
|---|---|---|
| DE | 11 2014 003 458 T5 | 4/2016 |
| EP | 2 295 421 A1 | 3/2011 |
| JP | 2015-042636 A | 3/2015 |
| JP | 2015-181169 A | 10/2015 |
| KR | 2011-0011647 A | 2/2011 |
| KR | 2015-0145033 A | 12/2015 |
| KR | 2016-0034937 A | 3/2016 |
| TW | 201002678 | 1/2010 |
| TW | 201509937 | 3/2015 |
| TW | 201538498 | 10/2015 |
| WO | WO 2009/145016 A2 | 12/2009 |
| WO | WO 2011/103552 A2 | 8/2011 |
| WO | WO 2015/011614 A1 | 1/2015 |
| WO | WO 2015/194791 A1 | 12/2015 |

OTHER PUBLICATIONS

Written Opinion re Application No. PCT/IB2017/055296, dated Oct. 24, 2016.

* cited by examiner

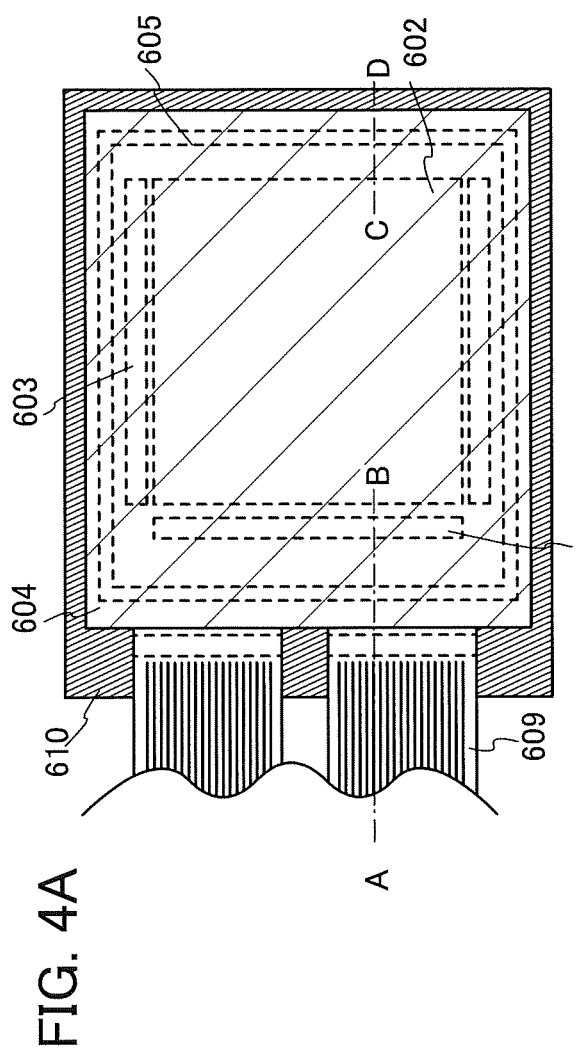
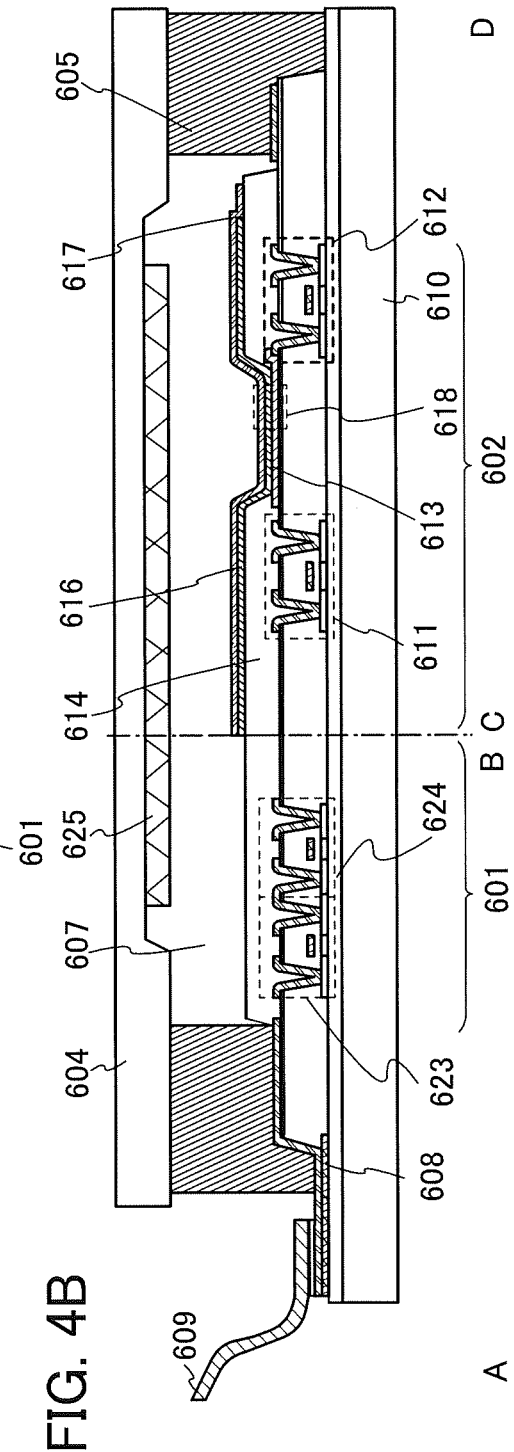
FIG. 4A
FIG. 4B

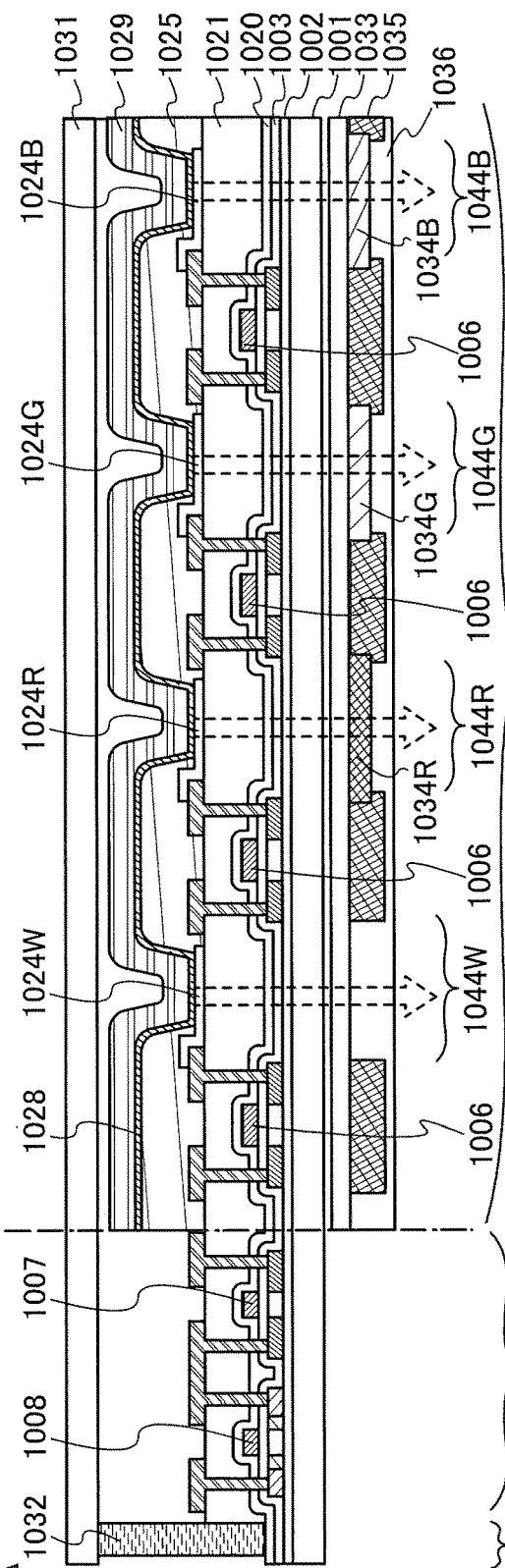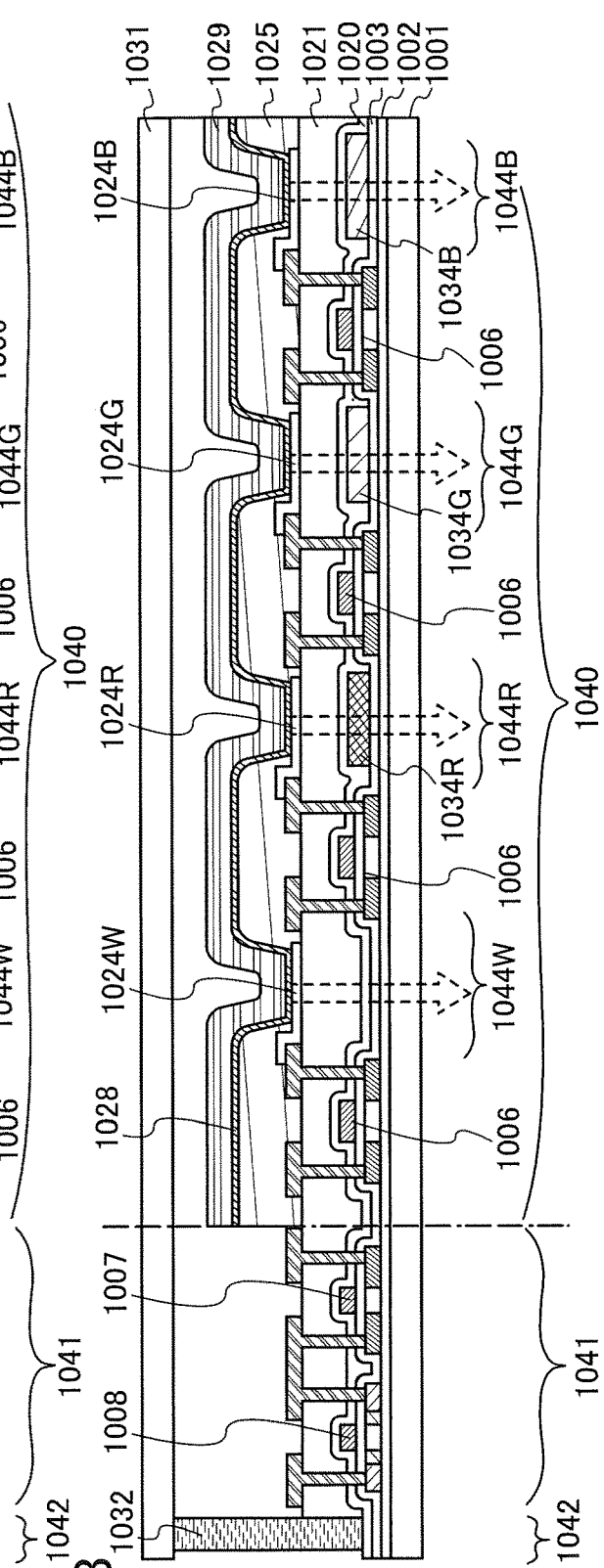
FIG. 5A
FIG. 5B

FIG. 7A
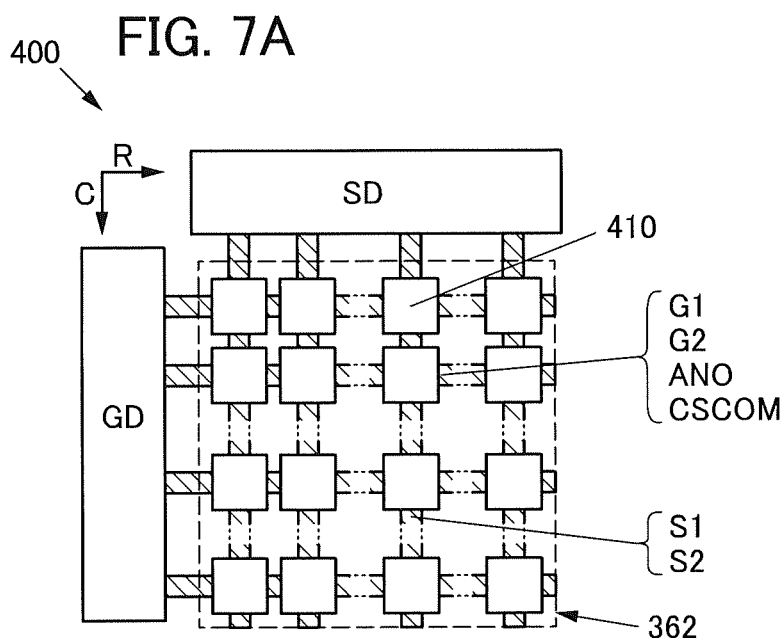
FIG. 7B1
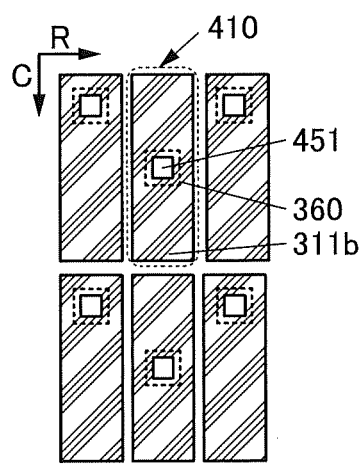
FIG. 7B2
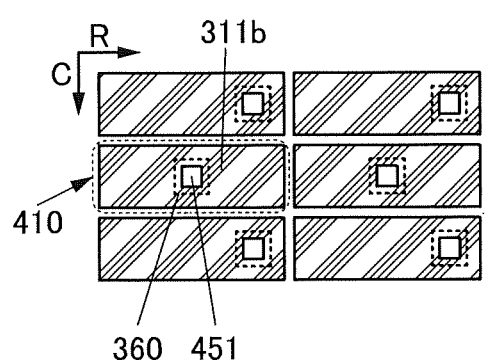

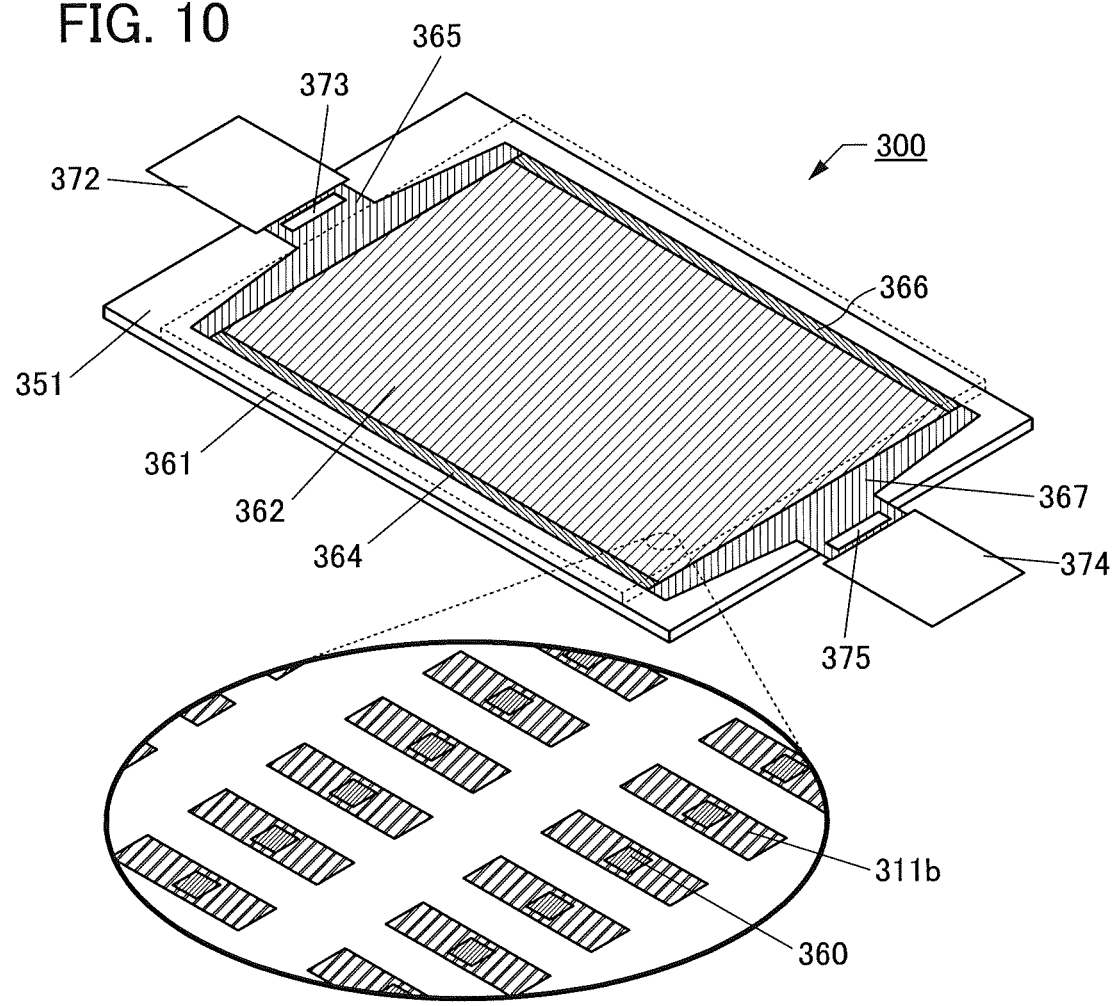

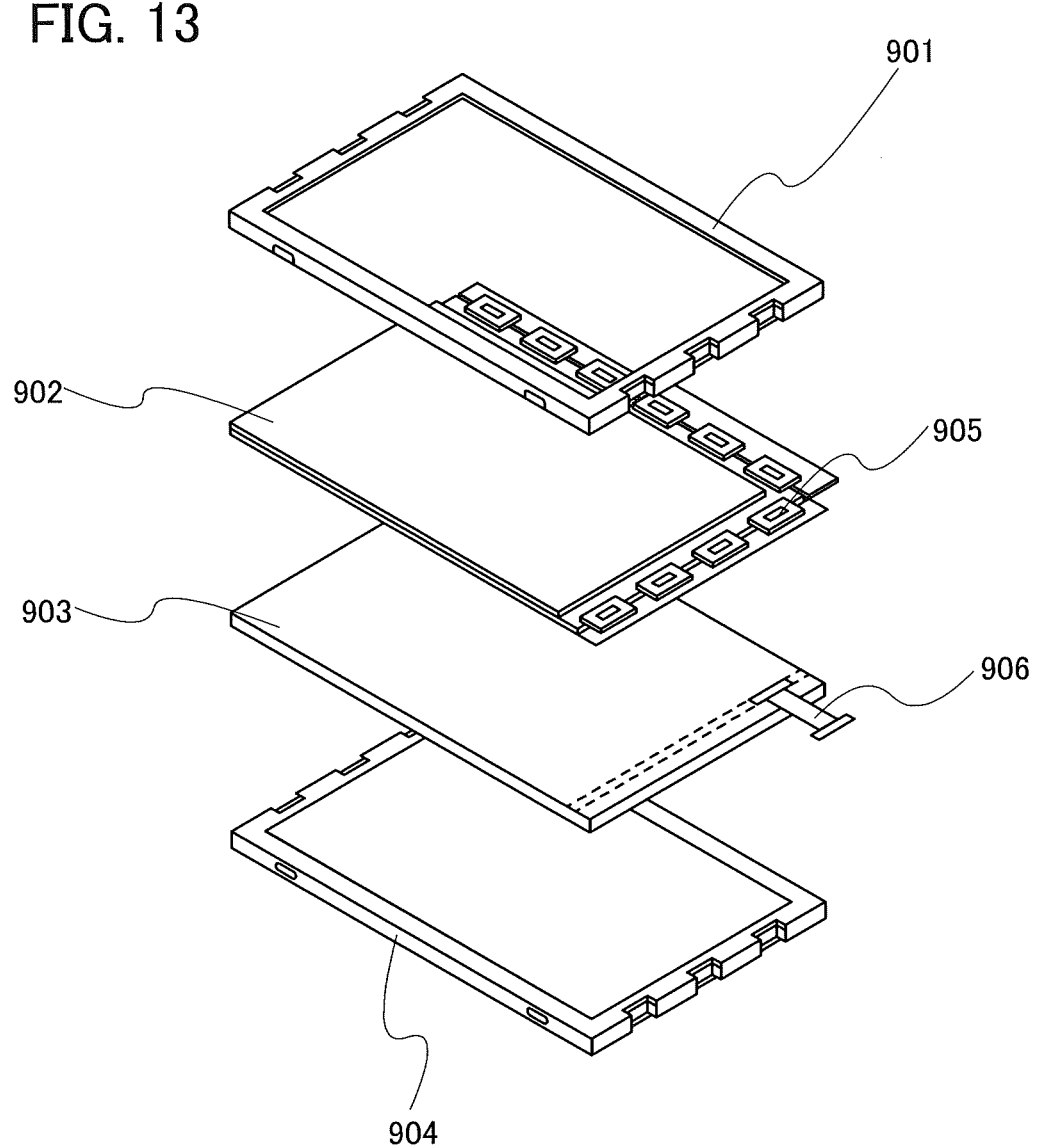

ORGANIC COMPOUND, LIGHT-EMITTING ELEMENT, LIGHT-EMITTING DEVICE, ELECTRONIC DEVICE, AND LIGHTING DEVICE

TECHNICAL FIELD

One embodiment of the present invention relates to a novel organic compound. One embodiment of the present invention also relates to an aromatic amine compound including a benzo[b]naphtho[1,2-d]furan skeleton. In addition, one embodiment of the present invention relates to a light-emitting element, a light-emitting device, an electronic device, and a lighting device each of which includes the organic compound.

Note that one embodiment of the present invention is not limited to the above technical field. One embodiment of the present invention relates to an object, a method, or a manufacturing method. In addition, the present invention relates to a process, a machine, manufacture, or a composition of matter. In particular, one embodiment of the present invention relates to a semiconductor device, a light-emitting device, a display device, a lighting device, a light-emitting element, or a manufacturing method thereof. In addition, one embodiment of the present invention relates to a novel method for synthesizing an aromatic amine compound including a benzonaphthofuran skeleton. Thus, specific examples of one embodiment of the present invention disclosed in this specification include a light-emitting element, a light-emitting device, an electronic device, and a lighting device, each of which includes the organic compound, and manufacturing methods of them.

BACKGROUND ART

Light-emitting elements (organic EL elements) including organic compounds and utilizing electroluminescence (EL) have been put to more practical use. In the basic structure of such a light-emitting element, an organic compound layer containing a light-emitting material (an electroluminescent (EL) layer) is provided between a pair of electrodes. Carriers are injected by application of voltage to the element, and light emission can be obtained from the light-emitting material by using the recombination energy of the carriers.

The light-emitting elements are self-luminous elements and thus have advantages such as high visibility and no need for backlight when used as pixels of a display, and are suitable as flat panel display elements. In addition, it is also a great advantage that a display including such light-emitting elements can be manufactured as a thin and lightweight display. Furthermore, an extremely high response speed is also a feature thereof.

In such light-emitting elements, light-emitting layers can be successively formed two-dimensionally, so that planar light emission can be obtained. This feature is difficult to obtain with point light sources typified by incandescent lamps and LEDs or linear light sources typified by fluorescent lamps. Furthermore, light emission from an organic compound can be light emission which does not include UV light by selecting a material; thus, light-emitting elements also have great potential as planar light sources used in lighting devices and the like.

Displays or lighting devices including light-emitting elements can be suitably used for a variety of electronic devices as described above; thus, research and development of light-emitting elements have progressed for higher efficiency or longer element lifetimes. In particular, an organic compound is mainly used in an EL layer and greatly affects an improvement in the characteristics of the light-emitting element. For this reason, a variety of novel organic compounds have been developed.

The lifetime and properties of a light-emitting element including an organic compound are greatly affected by the properties of a hole-transport material in some cases. In particular, the lifetime and properties of a light-emitting element differ significantly according to the type of hole-transport material.

In general, a compound in which π conjugated systems spread across a molecule, which is typified by an aromatic compound, is used as a hole-transport material. In particular, an aromatic amine compound has been developed. The properties of a hole-transport material in an aromatic amine compound greatly depend on an aromatic skeleton.

Although aromatic amine compounds including various aromatic skeletons have been reported and the properties and reliability of light-emitting elements including the compounds have been improved, advanced requirements for various properties including efficiency and durability are not yet satisfied (Patent Document 1, for example).

REFERENCE

Patent Document

[Patent Document 1] PCT International Publication No. WO2009/145016

DISCLOSURE OF INVENTION

In view of the above, an object of one embodiment of the present invention is to provide a novel organic compound. In particular, an object of one embodiment of the present invention is to provide a novel organic compound having a hole-transport property. Another object of one embodiment of the present invention is to provide a light-emitting element with a long lifetime. Another object of one embodiment of the present invention is to provide a light-emitting element with high emission efficiency. Another object of one embodiment of the present invention is to provide a light-emitting element with low driving voltage.

Another object of one embodiment of the present invention is to provide a light-emitting element, a light-emitting device, and an electronic device each having high reliability. Another object of one embodiment of the present invention is to provide a light-emitting element, a light-emitting device, and an electronic device each with low power consumption.

Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is an aromatic amine compound including two substituted or unsubstituted benzo[b]naphtho[1,2-d]furan skeletons.

Thus, one embodiment of the present invention is an organic compound represented by General Formula (G0).

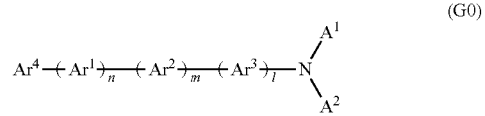

(G0)

In General Formula (G0), $Ar^1$, $Ar^2$, and $Ar^3$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, and n, m, and l independently represent an integer of 0 or 1. Furthermore, $A^1$ and $A^2$ independently represent a group represented by General Formula (g0) or General Formula (g1).

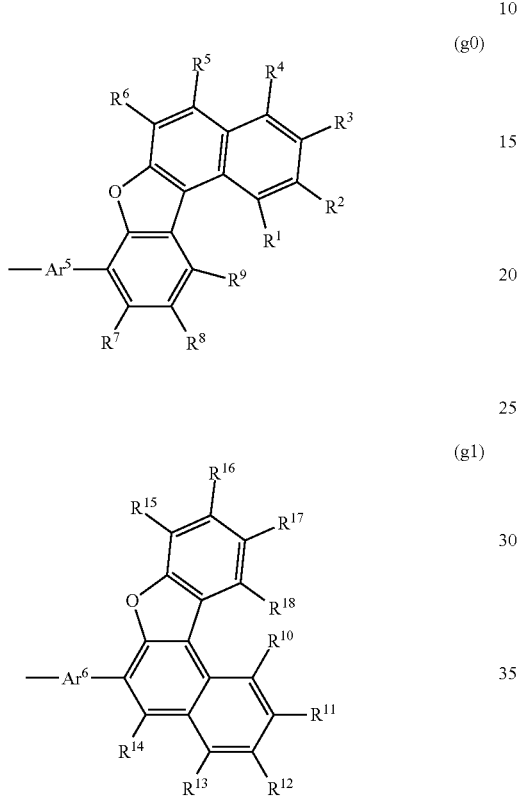

In General Formulae (g0) and (g1), $Ar^5$ and $Ar^6$ independently represent a substituted or unsubstituted divalent aromatic hydrocarbon group having 6 to 13 carbon atoms. In addition, $R^1$ to $R^{18}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 25 carbon atoms.

In General Formulae (g0) and (g1), it is preferable that $R^1$ to $R^{18}$ independently represent hydrogen or a substituted or unsubstituted aromatic hydrocarbon group having 6 to 13 carbon atoms.

Furthermore, in General Formulae (g0) and (g1), it is preferable that $R^6$ and $R^{15}$ independently represent a substituted or unsubstituted aromatic hydrocarbon group having 6 to 13 carbon atoms.

Another embodiment of the present invention is an organic compound in which $A^1$ and $A^2$ in General Formula (G0) are independently represented by General Formula (g0-a) or General Formula (g1-a).

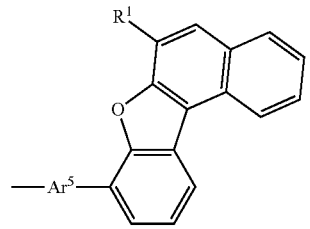

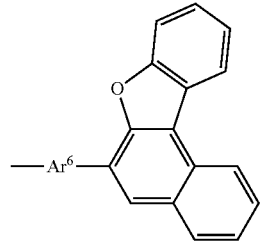

In General Formulae (g0-a) and (g1-a), $Ar^5$ and $Ar^6$ independently represent a substituted or unsubstituted divalent aromatic hydrocarbon group having 6 to 25 carbon atoms, and $R^1$ represents hydrogen or a substituted or unsubstituted phenyl group.

Another embodiment of the present invention is an organic compound represented by General Formula (G1).

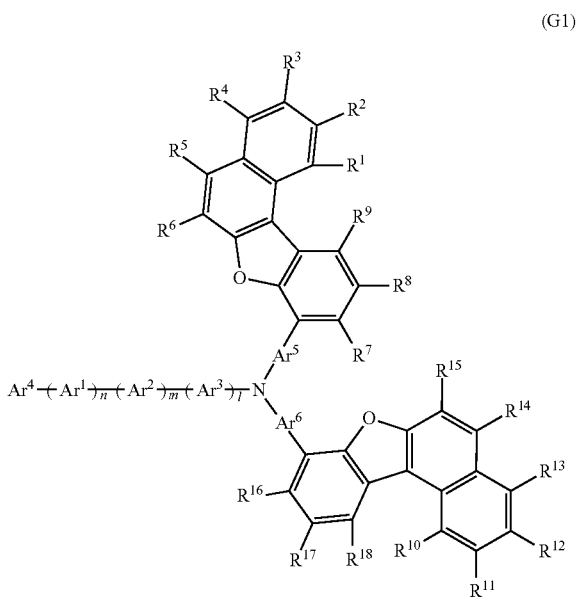

In General Formula (G1), $Ar^1$, $Ar^2$, $Ar^3$, $Ar^5$, and $Ar^6$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, and n, m, and l independently represent an integer of 0 or 1. In addition, $R^1$ to $R^{18}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 25 carbon atoms.

In General Formula (G1), it is preferable that $R^1$ to $R^{18}$ independently represent hydrogen or a substituted or unsubstituted aromatic hydrocarbon group having 6 to 13 carbon atoms.

In General Formula (G1), it is preferable that $R^6$ and $R^{15}$ independently represent a substituted or unsubstituted aromatic hydrocarbon group having 6 to 13 carbon atoms.

Another embodiment of the present invention is an organic compound represented by General Formula (G2).

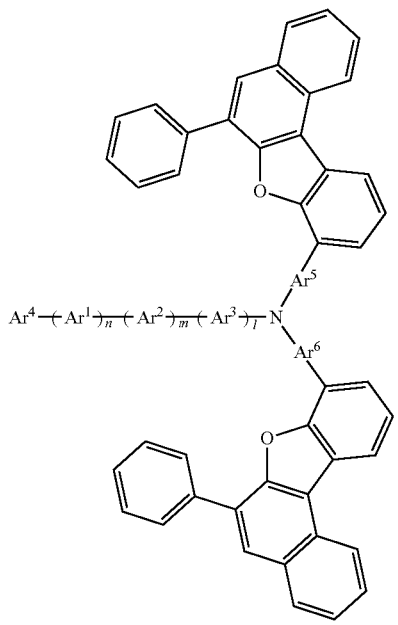
(G2)

In General Formula (G2), $Ar^1$, $Ar^2$, $Ar^3$, $Ar^5$, and $Ar^6$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, and n, m, and l independently represent an integer of 0 or 1.

Another embodiment of the present invention is an organic compound represented by General Formula (G3).

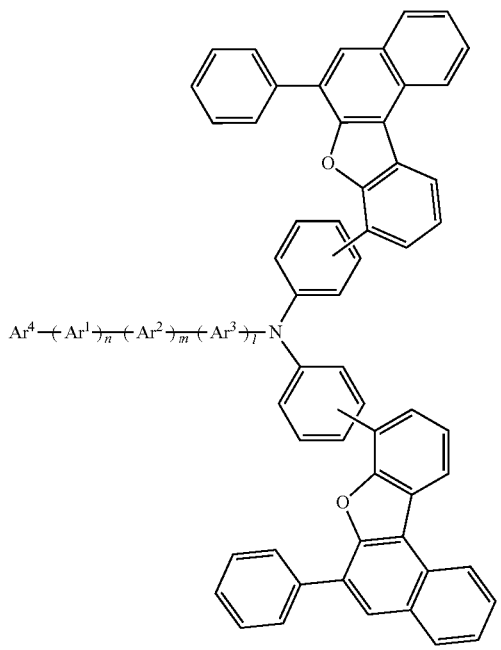
(G3)

In General Formula (G3), $Ar^1$, $Ar^2$, and $Ar^3$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, and n, m, and l independently represent an integer of 0 or 1.

Another embodiment of the present invention is an organic compound represented by General Formula (G4).

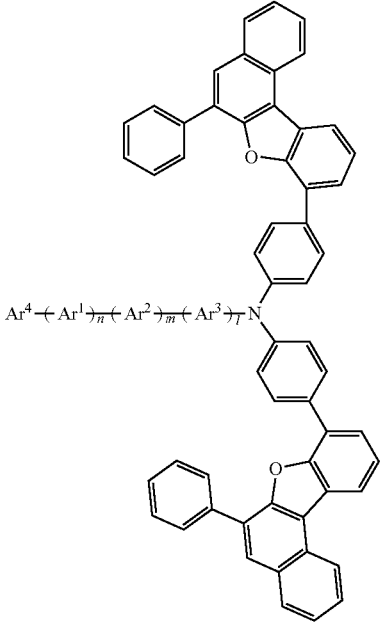
(G4)

In General Formula (G4), $Ar^1$, $Ar^2$, and $Ar^3$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, and n, m, and l independently represent an integer of 0 or 1.
Another embodiment of the present invention is an organic compound represented by General Formula (G5).
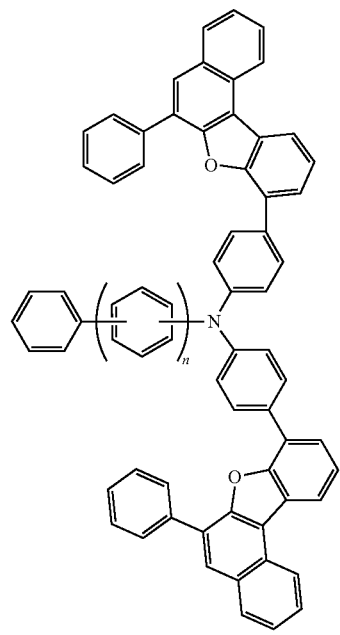
(G5)
In General Formula (G5), n represents an integer of 0 to 3.
Another embodiment of the present invention is an organic compound represented by any one of Structural Formulae (102), (103), (106), and (117).
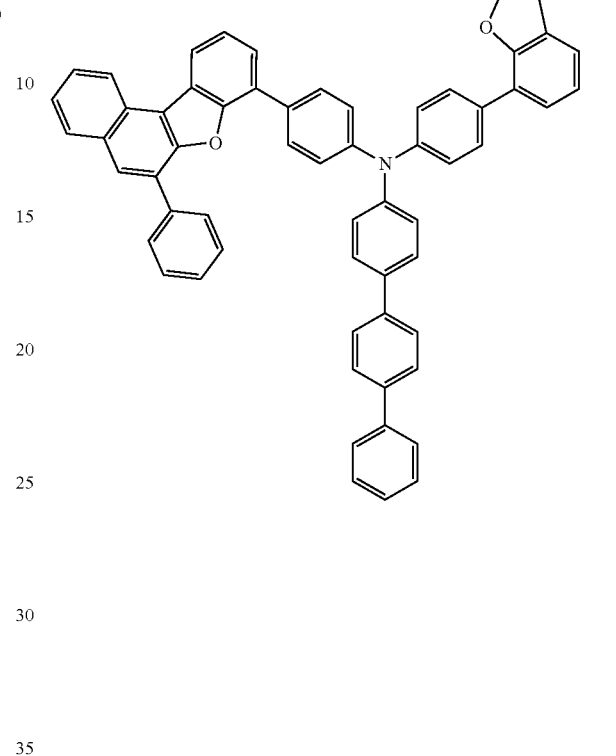
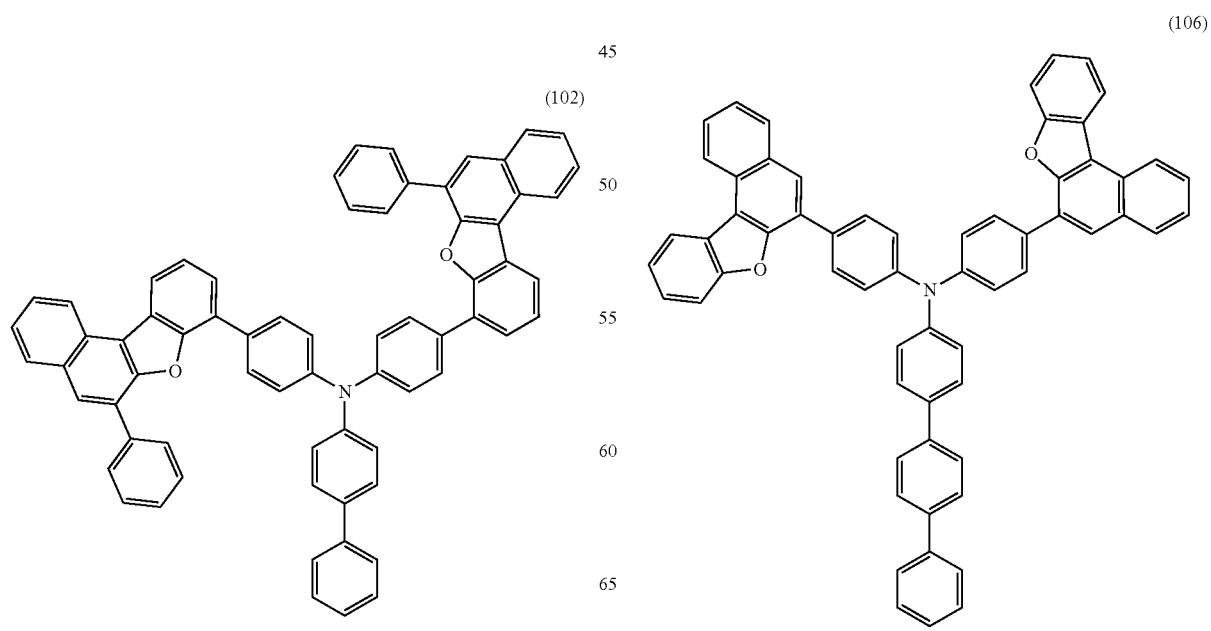

-continued (117)

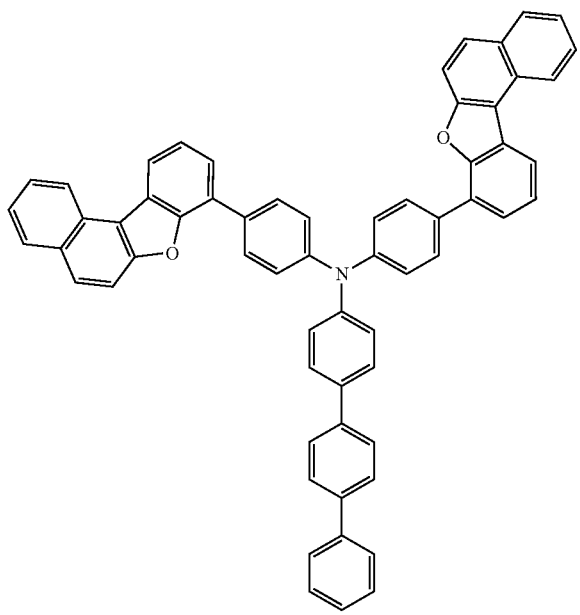

Another embodiment of the present invention is a light-emitting element that contains any of the above-described organic compounds.

The light-emitting element in the above embodiment includes an EL layer between an anode and a cathode. The EL layer includes at least one of a light-emitting layer, a hole-transport layer, a hole-injection layer, an electron-transport layer, and an electron-injection layer. In the above embodiment, the EL layer preferably includes the light-emitting layer and the hole-transport layer. The hole-transport layer is preferably positioned between the anode and the light-emitting layer. Note that the EL layer may include another functional layer.

In the above embodiment, the light-emitting layer preferably contains a light-emitting material.

Another embodiment of the present invention is a display device including the light-emitting element having any of the above-described structures, and at least one of a color filter and a transistor. Another embodiment of the present invention is an electronic device including the above-described display device and at least one of a housing and a touch sensor. Another embodiment of the present invention is a lighting device including the light-emitting element having any of the above-described structures, and at least one of a housing and a touch sensor. The category of one embodiment of the present invention includes not only a light-emitting device including a light-emitting element but also an electronic device including a light-emitting device. Accordingly, a light-emitting device in this specification refers to an image display device or a light source (including a lighting device). The light-emitting device may be included in a module in which a connector such as a flexible printed circuit (FPC) or a tape carrier package (TCP) is connected to a light-emitting element, a module in which a printed wiring board is provided on the tip of a TCP, or a module in which an integrated circuit (IC) is directly mounted on a light-emitting element by a chip on glass (COG) method.

According to one embodiment of the present invention, a novel organic compound can be provided. In particular, a novel organic compound having a hole-transport property can be provided. According to one embodiment of the present invention, a light-emitting element with a long lifetime can be provided. According to one embodiment of the present invention, a light-emitting element with high emission efficiency can be provided. According to one embodiment of the present invention, a light-emitting element with low driving voltage can be provided.

According to another embodiment of the present invention, a light-emitting device and an electronic device each having high reliability can be provided. According to another embodiment of the present invention, a light-emitting device and an electronic device each with low power consumption can be provided.

Note that the descriptions of these effects do not disturb the existence of other effects. In one embodiment of the present invention, there is no need to achieve all the effects. Other effects will be apparent from and can be derived from the description of the specification, the drawings, the claims, and the like.

BRIEF DESCRIPTION OF DRAWINGS

In the accompanying drawings:

FIGS. 4A and 4B are conceptual diagrams of an active matrix light-emitting device of one embodiment of the present invention;

FIGS. 5A and 5B are conceptual diagrams of an active matrix light-emitting device of one embodiment of the present invention;

FIGS. 7A, 7B1, and 7B2 are schematic views of a display device of one embodiment of the present invention;

FIG. 10 is a schematic view of a display device of one embodiment of the present invention;

FIG. 13 illustrates a light source device of one embodiment of the present invention;

BEST MODE FOR CARRYING OUT THE INVENTION

Figure 1A:
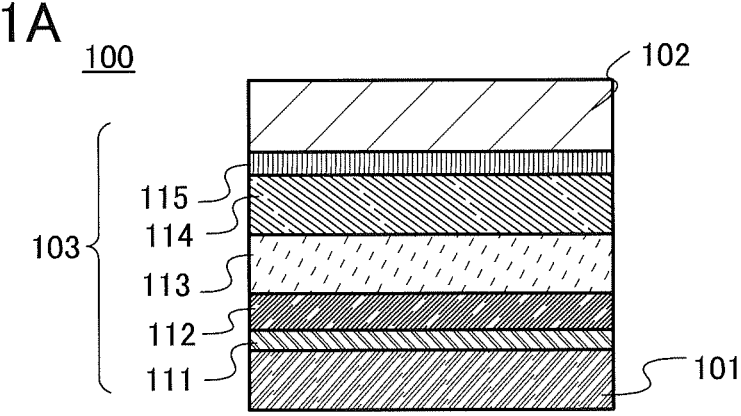
FIGS. 1A to 1C are schematic views of light-emitting elements of one embodiment of the present invention.

Embodiments of the present invention will be described below. Note that it is easily understood by those skilled in the art that modes and details disclosed herein can be modified in various ways without departing from the spirit and scope of the present invention. Therefore, the present invention is not construed as being limited to the description of the following embodiments.

Note that in each drawing described in this specification, the size, the thickness, and the like of components such as an anode, an EL layer, an intermediate layer, and a cathode are exaggerated for clarity in some cases. Therefore, the sizes of the components are not limited to the sizes in the drawings and relative sizes between the components.

Note that the ordinal numbers such as "first", "second", and "third" in this specification and the like are used for convenience and do not denote the order of steps, the positional relation, or the like. Therefore, for example, description can be made even when "first" is replaced with "second" or "third", as appropriate. In addition, the ordinal numbers in this specification and the like are not necessarily the same as those which specify one embodiment of the present invention.

In the structures of the present invention described in this specification and the like, the same portions or portions having similar functions in different drawings are denoted by the same reference numerals, and description of such portions is not repeated. Furthermore, the same hatching pattern is applied to portions having similar functions, and the portions are not especially denoted by reference numerals in some cases.

In this specification, color is defined by three aspects of hue (corresponding to the wavelength of light of a single color), chroma (saturation, i.e., the degree to which it differs from white), and value (brightness, i.e., the intensity of light). In this specification, color may be defined by only one of the above three aspects or two of the aspects which are selected arbitrarily. In this specification, a difference between two colors of light means a difference in at least one of the above three aspects and includes a difference in the shapes of two spectra of light or in the distributions of the relative intensity of the peaks in the spectra.

Note that the terms "film" and "layer" can be interchanged with each other depending on the case or circumstances. For example, the term "conductive layer" can be changed into the term "conductive film" in some cases, and the term "insulating film" can be changed into the term "insulating layer" in some cases.

Embodiment 1

In this embodiment, an organic compound of one embodiment of the present invention is described below, for example.

An organic compound of one embodiment of the present invention is represented by General Formula (G0).

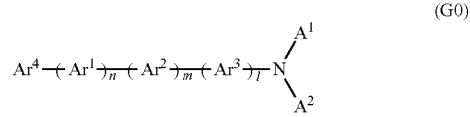

(G0)

In General Formula (G0), $Ar^1$, $Ar^2$, and $Ar^3$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, and n, in, and l independently represent an integer of 0 or 1. In addition, $A^1$ and $A^2$ independently represent a group represented by General Formula (g0) or (g1).

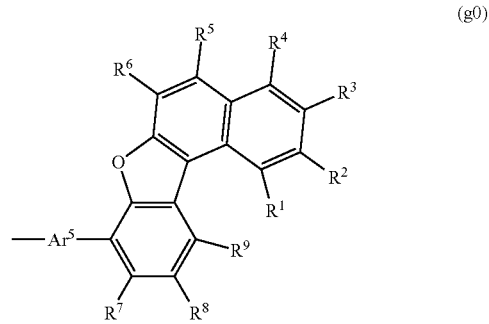

(g0)

-continued (g1)

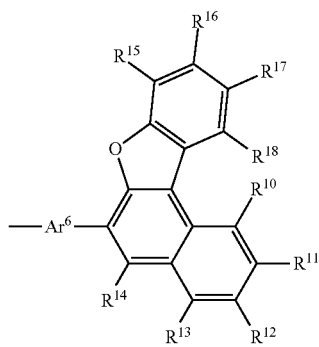

In General Formulae (g0) and (g1), $Ar^5$ and $Ar^6$ independently represent a substituted or unsubstituted divalent aromatic hydrocarbon group having 6 to 13 carbon atoms. In addition, $R^1$ to $R^{18}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 25 carbon atoms.

Another embodiment of the present invention is an organic compound in which $R^1$ to $R^{18}$ in General Formulae (g0) and (g1) independently represent hydrogen or a substituted or unsubstituted aromatic hydrocarbon group having 6 to 13 carbon atoms.

Another embodiment of the present invention is an organic compound in which $R^6$ and $R^{15}$ in General Formulae (g0) and (g1) independently represent a substituted or unsubstituted aromatic hydrocarbon group having 6 to 13 carbon atoms.

Another embodiment of the present invention is an organic compound in which $A^1$ and $A^2$ in General Formula (G0) are independently represented by General Formula (g0-a) or (g1-a).

(g0-a)

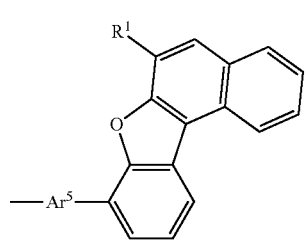

(g1-a)

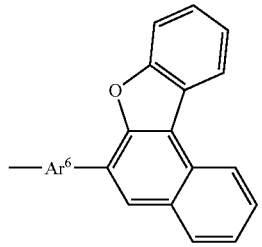

In General Formulae (g0-a) and (g1-a), $Ar^5$ and $Ar^6$ independently represent a substituted or unsubstituted divalent aromatic hydrocarbon group having 6 to 25 carbon atoms, and $R^1$ represents hydrogen or a substituted or unsubstituted phenyl group.

Another embodiment of the present invention is an organic compound represented by General Formula (G1). In the organic compound, distribution of π conjugated systems spreads to a benzo[b]naphtho[1,2-d]furan skeleton, which is a bulky substituent in the organic compound; thus, a high carrier-transport property can be obtained. With such a structure, the organic compound can have a high T1 level.

(G1)

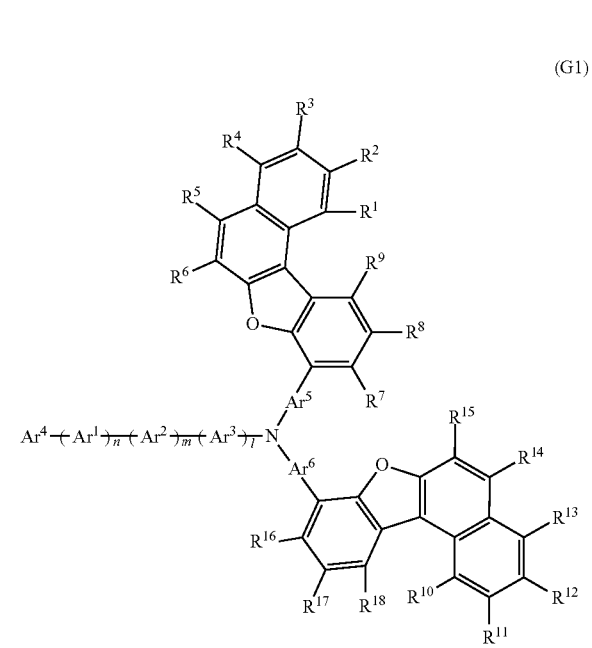

In General Formula (G1), $Ar^1$, $Ar^2$, $Ar^3$, $Ar^5$, and $Ar^6$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, and n, m, and l independently represent an integer of 0 or 1. In addition, $R^1$ to $R^{18}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 25 carbon atoms.

Another embodiment of the present invention is an organic compound represented by General Formula (G2). In the organic compound, distribution of π conjugated systems spreads to a benzo[b]naphtho[1,2-d]furan skeleton; thus, a high carrier-transport property can be obtained. With such a structure, the organic compound can have a high T1 level.

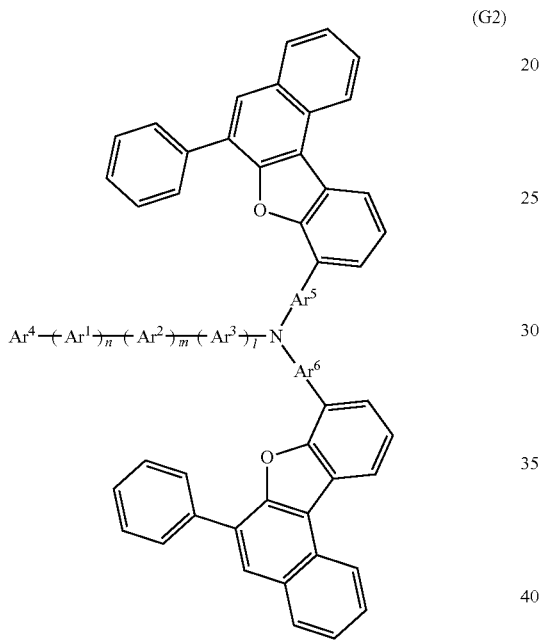

(G2)

In General Formula (G2), $Ar^1$, $Ar^2$, $Ar^3$, $Ar^5$, and $Ar^6$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, and n, m, and l independently represent an integer of 0 or 1.

Another embodiment of the present invention is an organic compound represented by General Formula (G3). In the organic compound, distribution of π conjugated systems spreads to a benzo[b]naphtho[1,2-d]furan skeleton, which is a bulky substituent in the organic compound; thus, a high carrier-transport property can be obtained. Furthermore, in the organic compound represented by General Formula (G3), an amino group is bonded to the 8-position of the benzo[b]naphtho[1,2-d]furan skeleton through a phenylene group; thus, the organic compound can have a high T1 level even when π conjugated systems spread.

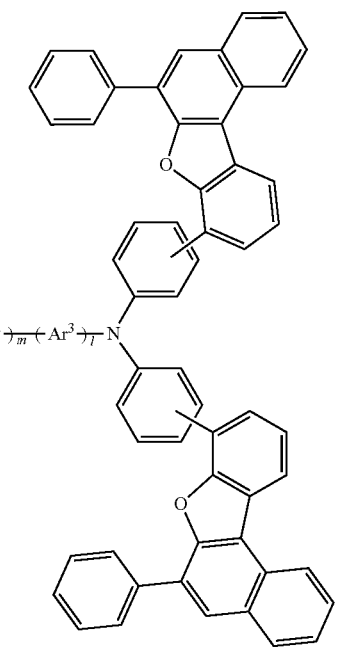

(G3)

In General Formula (G3), $Ar^1$, $Ar^2$, and $Ar^3$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, and n, m, and l independently represent an integer of 0 or 1.

Another embodiment of the present invention is an organic compound represented by General Formula (G4). In the organic compound, distribution of π conjugated systems spreads to a benzo[b]naphtho[1,2-d]furan skeleton, which is a bulky substituent in the organic compound; thus, a high carrier-transport property can be obtained. Furthermore, in the organic compound represented by General Formula (G4), an amino group is bonded to the 8-position of the benzo[b]naphtho[1,2-d]furan skeleton through a phenylene group; thus, the organic compound can have a high T1 level even when π conjugated systems spread.

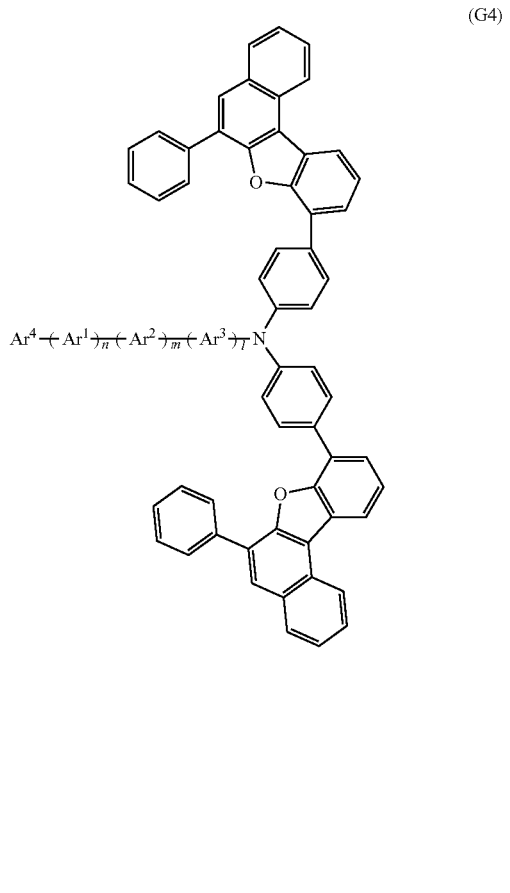

(G4)

$$Ar^4-(Ar^1)_n-(Ar^2)_m-(Ar^3)_l-N$$

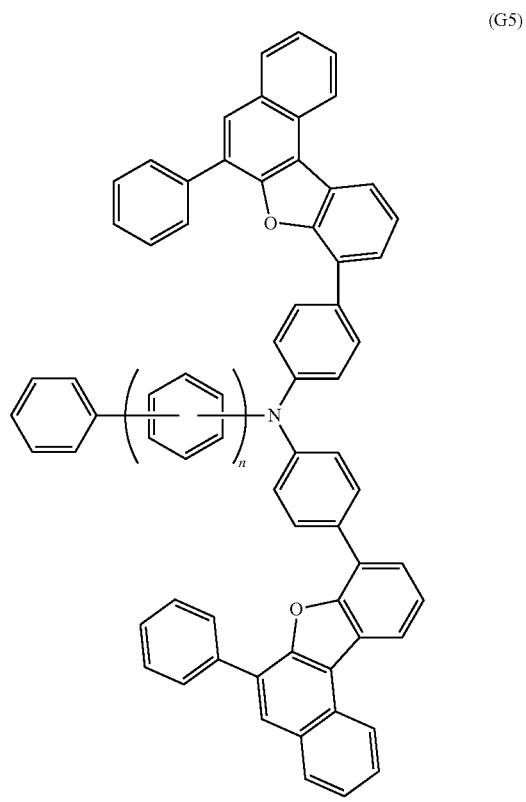

(G5)

In General Formula (G4), $A^1$, $Ar^2$, and $Ar^3$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, and n, m, and l independently represent an integer of 0 or 1.

Another embodiment of the present invention is an organic compound represented by General Formula (G5). In the organic compound, distribution of π conjugated systems spreads to a benzo[b]naphtho[1,2-d]furan skeleton, which is a bulky substituent in the organic compound; thus, a high carrier-transport property can be obtained. In the organic compound represented by General Formula (G5), an amino group is bonded to the 8-position of the benzo[b]naphtho[1,2-d]furan skeleton through a phenylene group; thus, the organic compound can have a high T1 level even when π conjugated systems spread.

Note that in General Formula (G5), n represents an integer of 0 to 3.

Another embodiment of the present invention is an organic compound represented by any one of Structural Formulae (102), (103), (106), and (117).

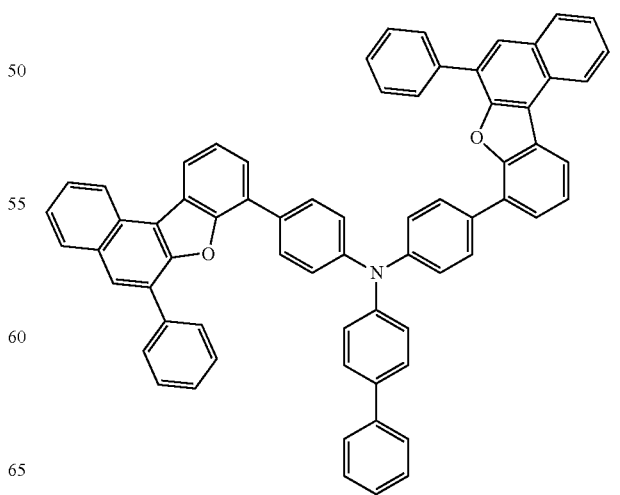

(102)

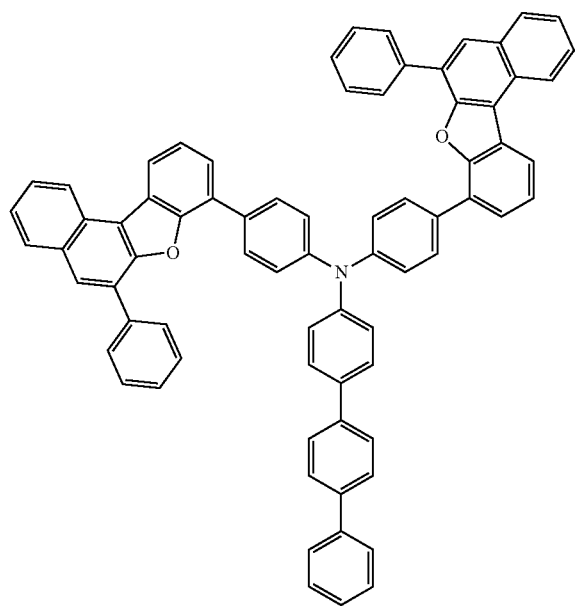

(103)

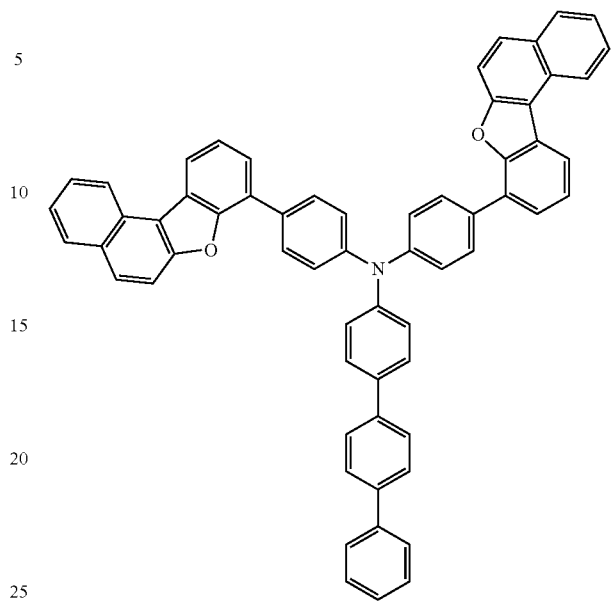

(117)

<Examples of Substituents>

In General Formulae (G0) to (G4) and General Formulae (g0) and (g1), examples of the divalent aromatic hydrocarbon groups represented by $Ar^1$, $Ar^2$, $Ar^3$, $Ar^5$, and $Ar^6$ include a phenylene group, a naphthylene group, a biphenyl-diyl group, a 9H-fluoren-diyl group, and a 9,9'-spirobi[9H-fluoren]-diyl group. Specifically, groups represented by Structural Formulae (Ar-1) to (Ar-18) can be used. Note that the groups represented by $Ar^1$, $Ar^2$, $Ar^3$, $Ar^5$, and $Ar^6$ are not limited thereto and may each include a substituent.

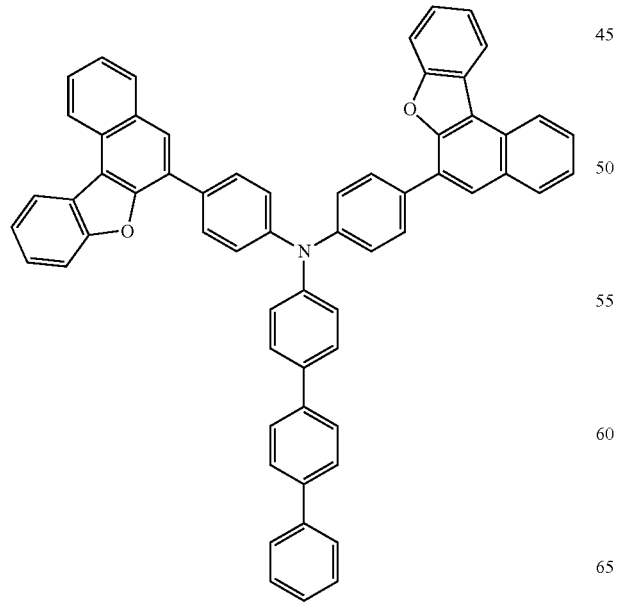

(106)

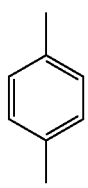

(Ar-1)

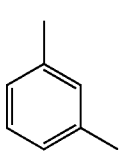

(Ar-2)

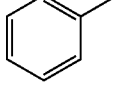

(Ar-3)

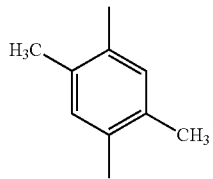

(Ar-4)

(Ar-5) 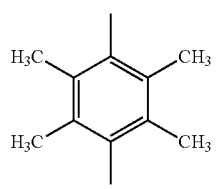
(Ar-6) 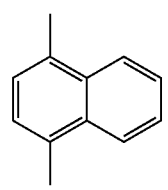
(Ar-7) 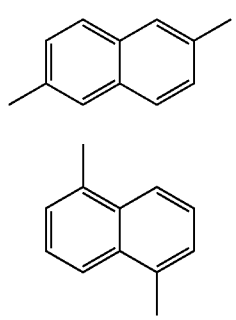
(Ar-8) 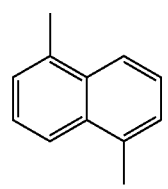
(Ar-9) 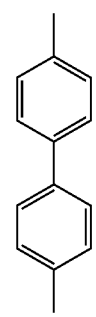
(Ar-10) 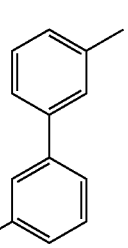
(Ar-11) 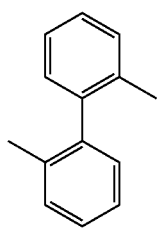
(Ar-12) 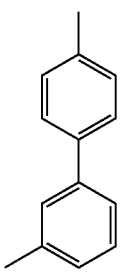
(Ar-13) 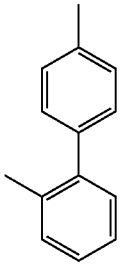
(Ar-14) 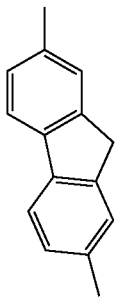
(Ar-15) 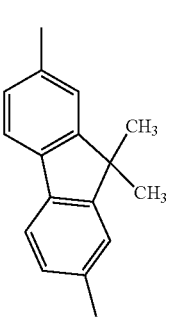
(Ar-16) 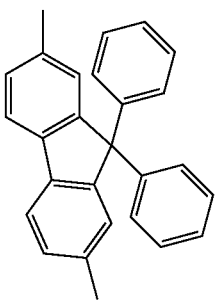

(Ar-17)

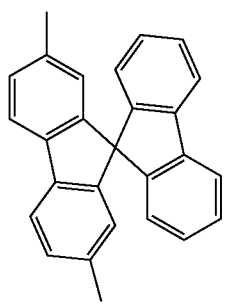

(Ar-18)

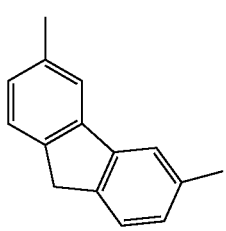

In General Formulae (G0) to (G4) and General Formulae (g0) and (g1), examples of the aromatic hydrocarbon group represented by $Ar^4$ include a phenyl group, a naphthyl group, and a substituent obtained by combining them. Specifically, groups represented by Structural Formulae (Ar-19) to (Ar-31) can be used. Note that the group represented by $Ar^4$ is not limited thereto and may include a substituent.

(Ar-19)

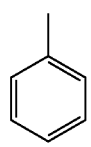

(Ar-20)

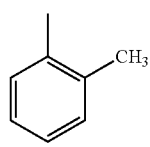

(Ar-21)

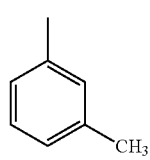

(Ar-22)

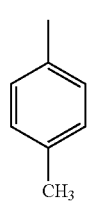

(Ar-23)

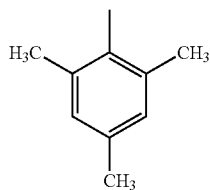

(Ar-24)

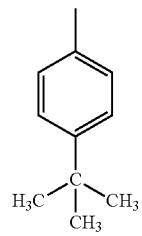

(Ar-25)

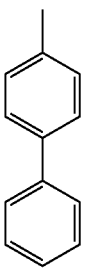

(Ar-26)

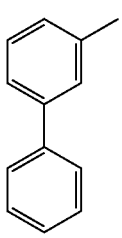

(Ar-27)

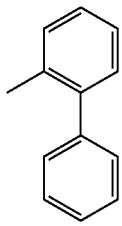

(Ar-28)

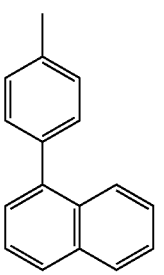

(Ar-29)

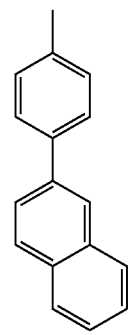

(Ar-30)

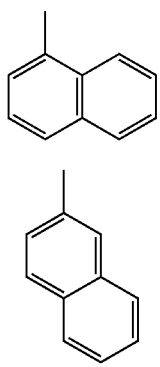

(Ar-31)

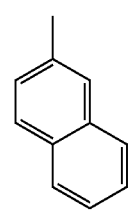

In General Formulae (G0), (g0), and (g1), examples of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 25 carbon atoms, which are represented by $R^1$ to $R^{18}$, include groups represented by Structural Formulae (R-1) to (R-57). Note that the groups represented by $R^1$ to $R^{18}$ are not limited thereto.

When $Ar^1$ to $Ar^6$ and $R^1$ to $R^{18}$ each include a substituent, examples of the substituent include groups represented by Structural Formulae (R-1) to (R-57); however, the substituent is not limited thereto.

(R-1)

H (R-2)

CH$_3$ (R-3)

(R-4)

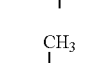

(R-5)

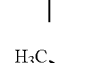

(R-6)

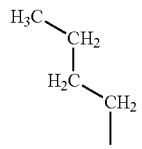

(R-7)

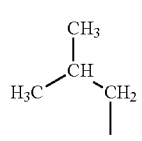

(R-8)

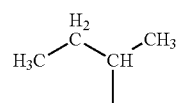

(R-9)

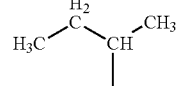

(R-10)

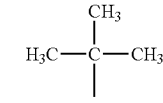

(R-11)

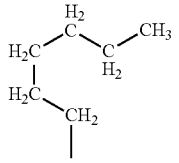

(R-12)

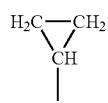

(R-13)

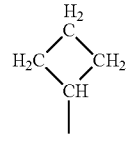

(R-14)

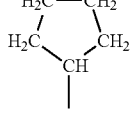

(R-15)

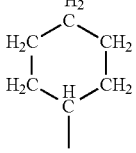

(R-16)

F (R-17)

Cl (R-18)

Br

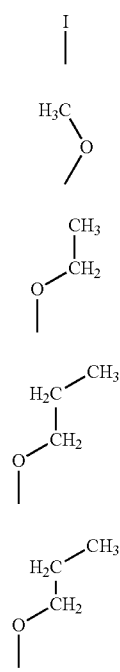 (R-19) (R-20) (R-21) (R-22) (R-23) (R-24)
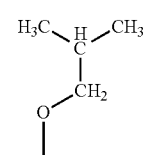 (R-25)
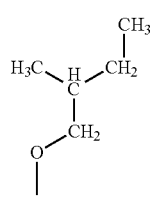 (R-26)
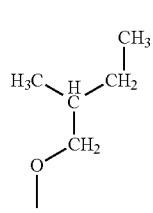 (R-27) (R-28)
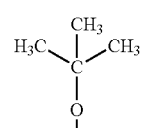 (R-29)
 (R-30)
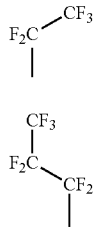 (R-31) (R-32)
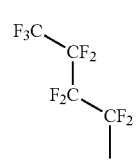 (R-33)
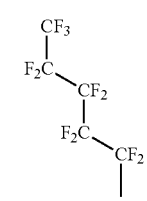 (R-34)
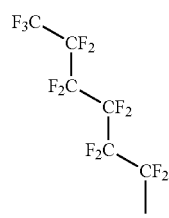 (R-35)
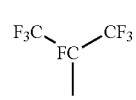 (R-36)
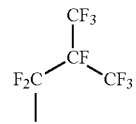 (R-37)
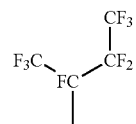 (R-38)
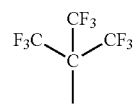 (R-39)

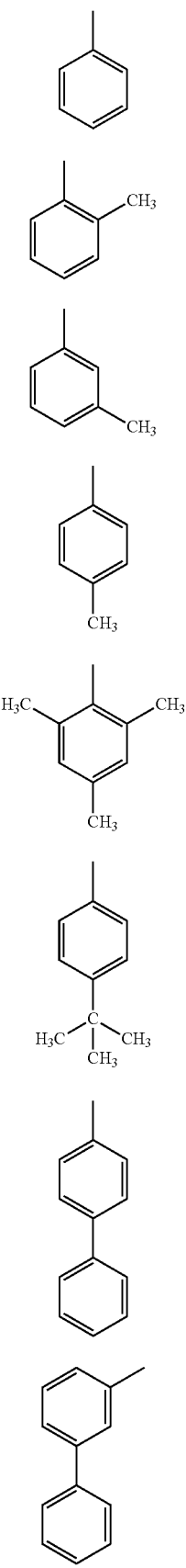

(R-54)
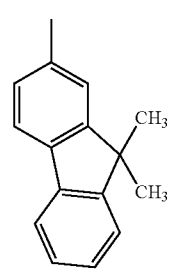
(101)
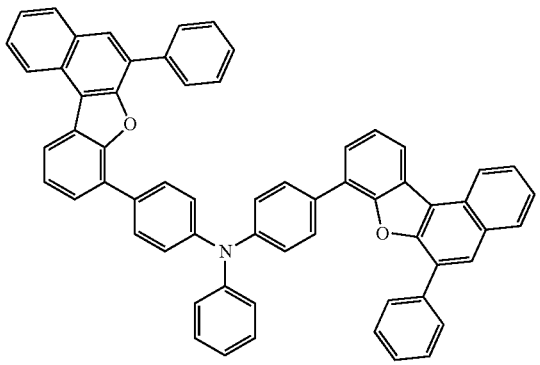
(R-55)
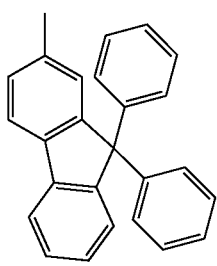
(102)
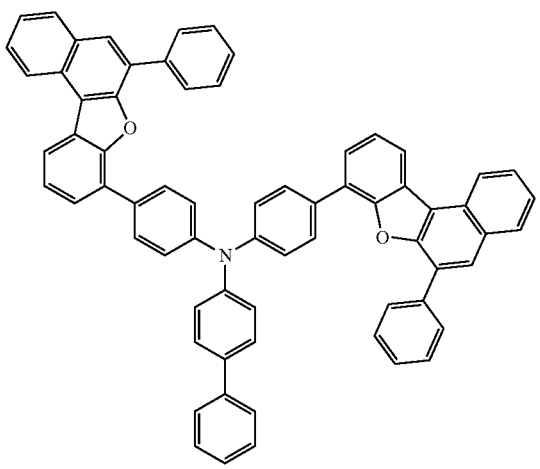
(R-56)
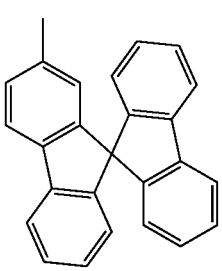
(R-57)
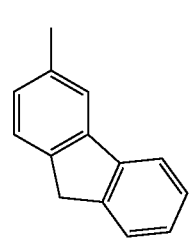
(103)
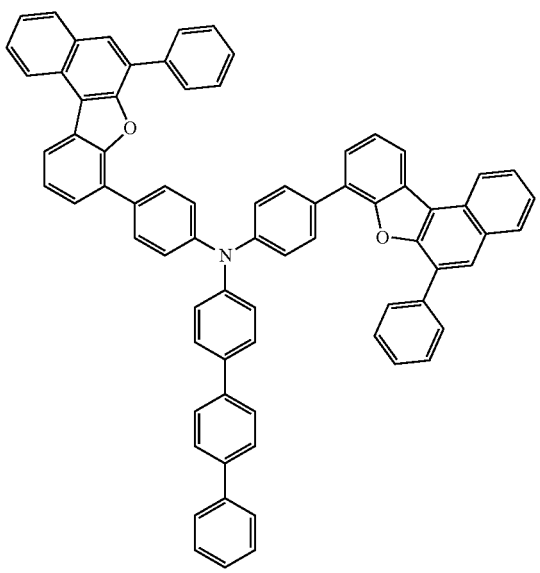
<Specific Examples of Compounds>
Specific examples of structures of the compounds represented by General Formulae (G0) to (G4) include compounds represented by Structural Formulae (101) to (152). Note that the compounds represented by General Formulae (G0) to (G4) are not limited to the following examples.

(104)
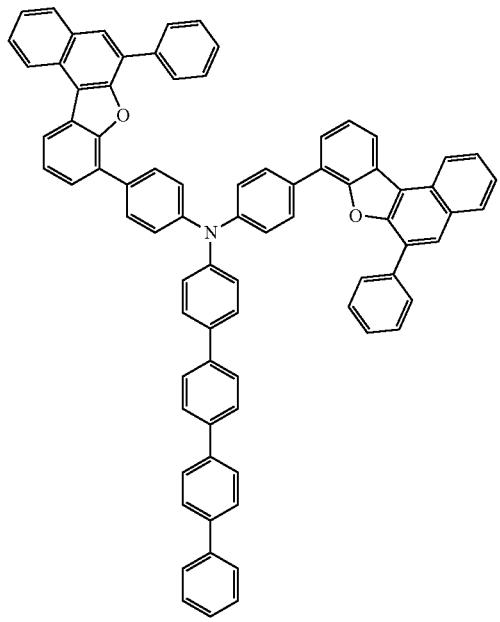
(105)
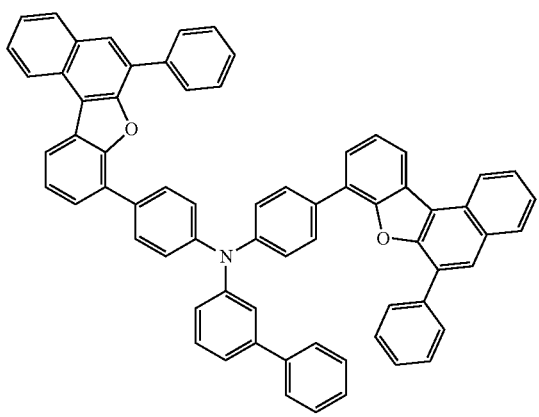
(106)
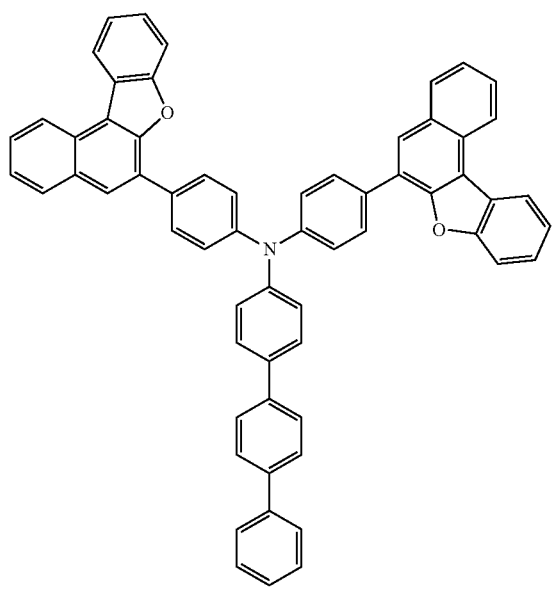
(107)
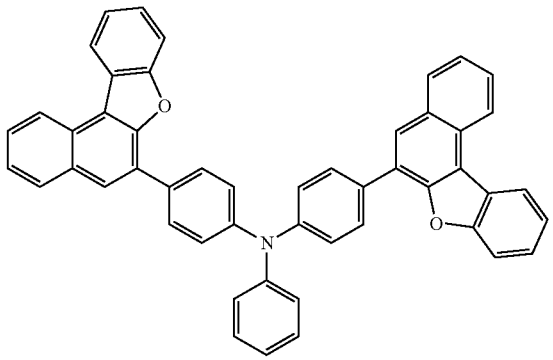
(108)
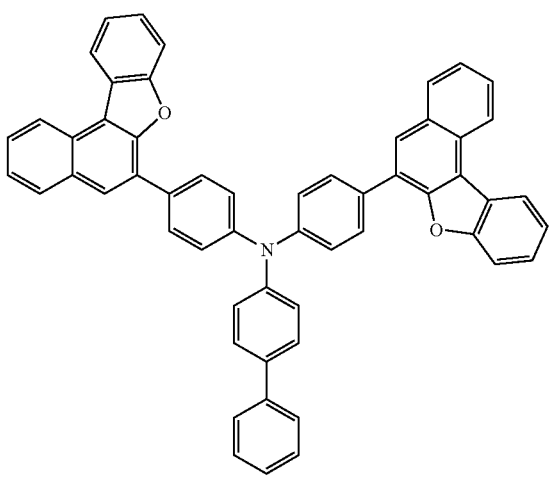
(109)
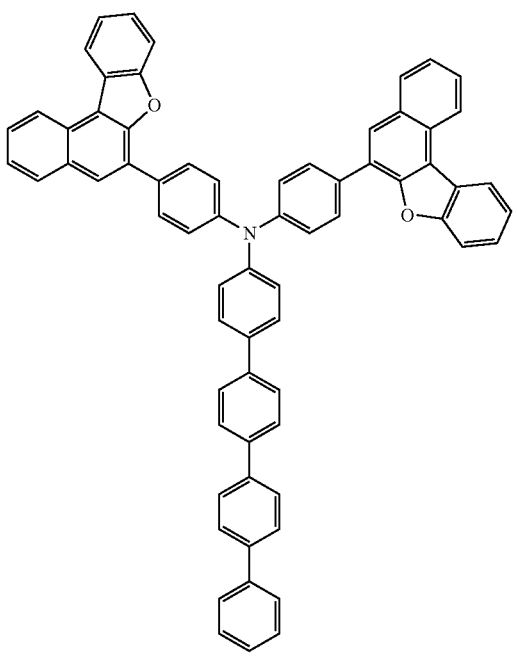

(110)
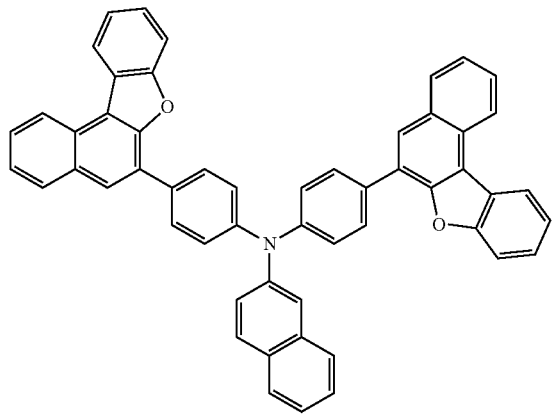
(111)
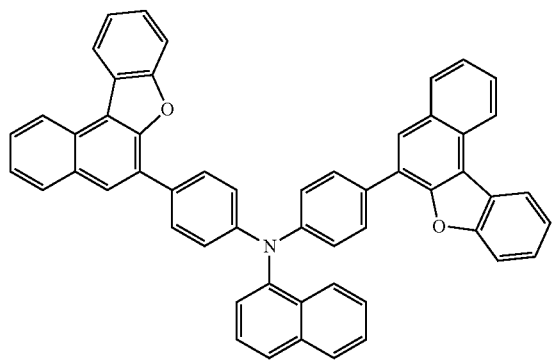
(112)
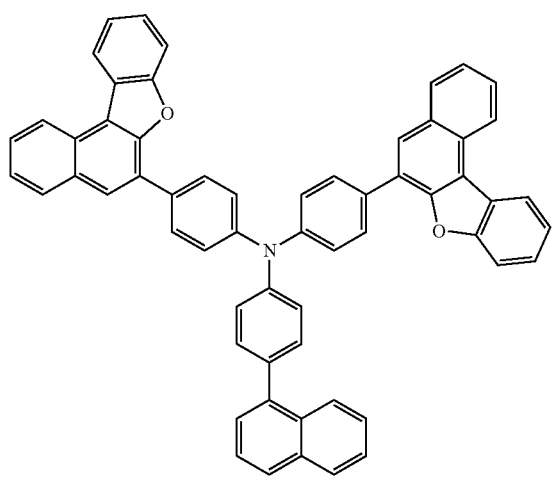
(113)
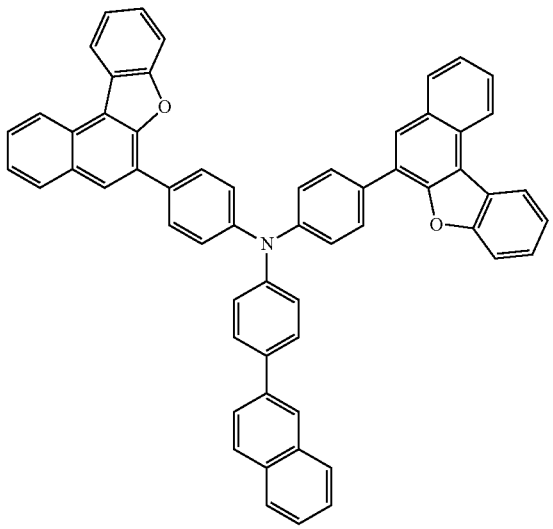
(114)
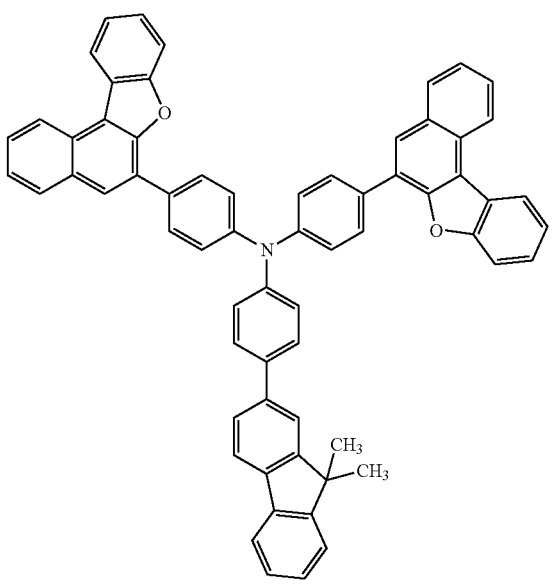
(115)
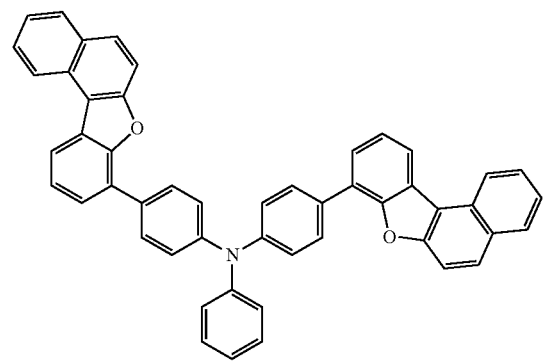

(116)
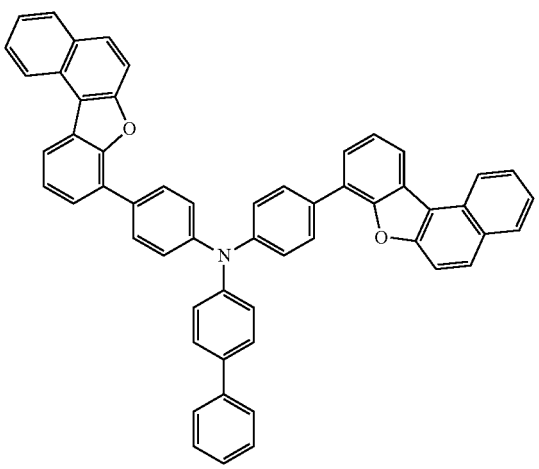
(117)
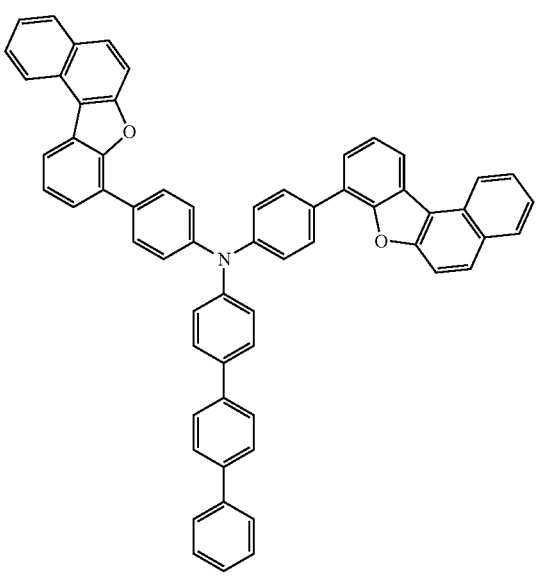
(118)
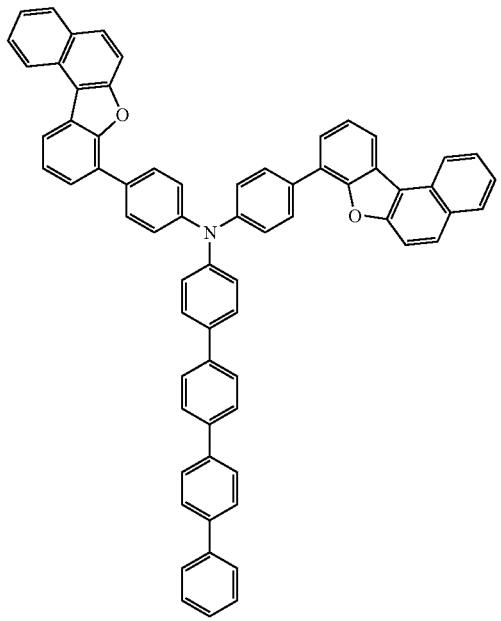
(119)
(120)
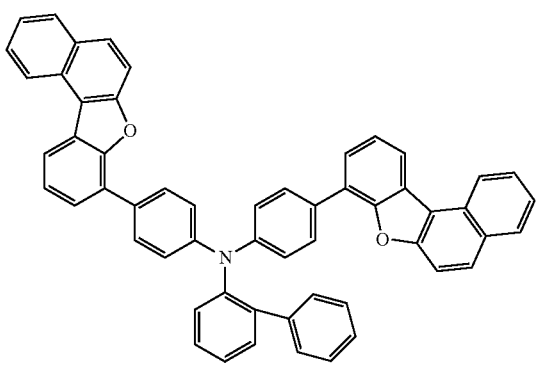

(121)
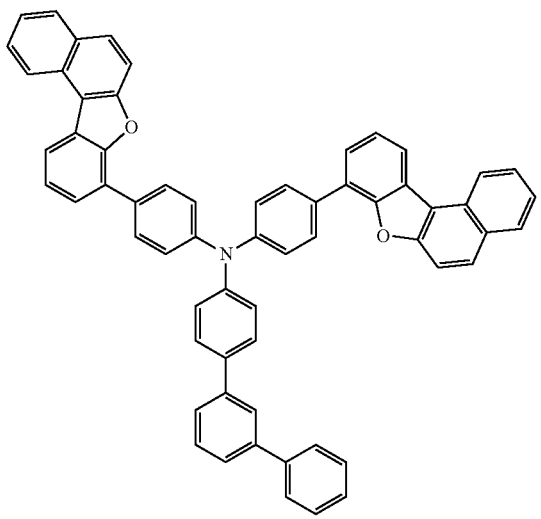
(122)
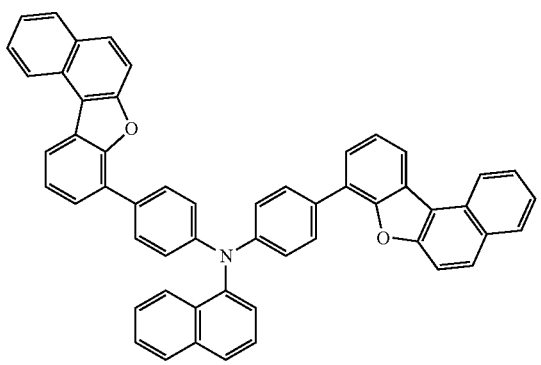
(123)
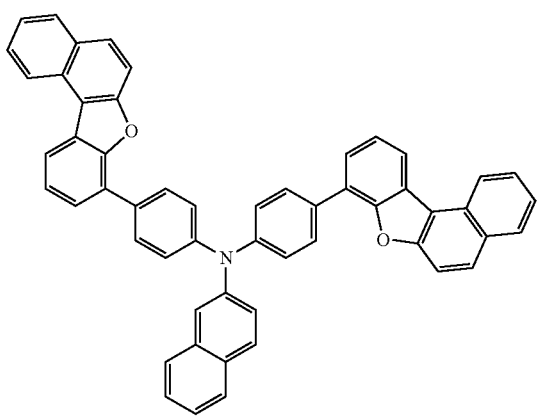
(124)
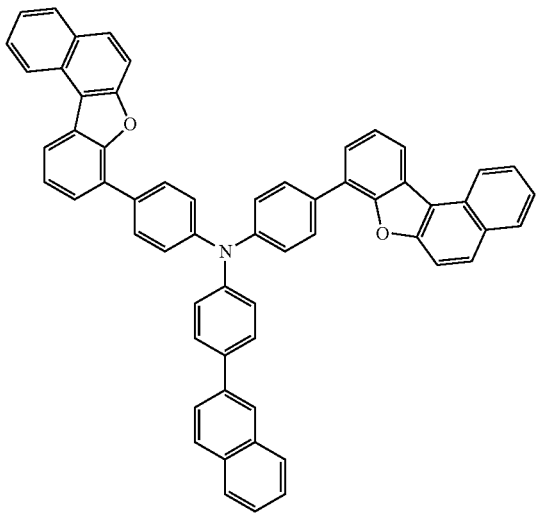
(125)
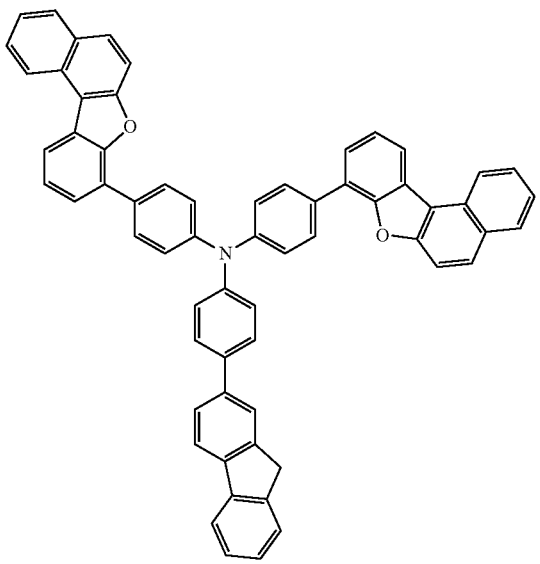
(126)

(127)
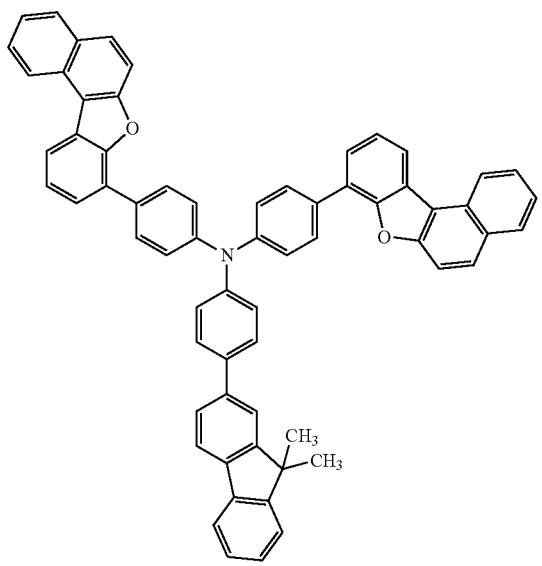
(128)
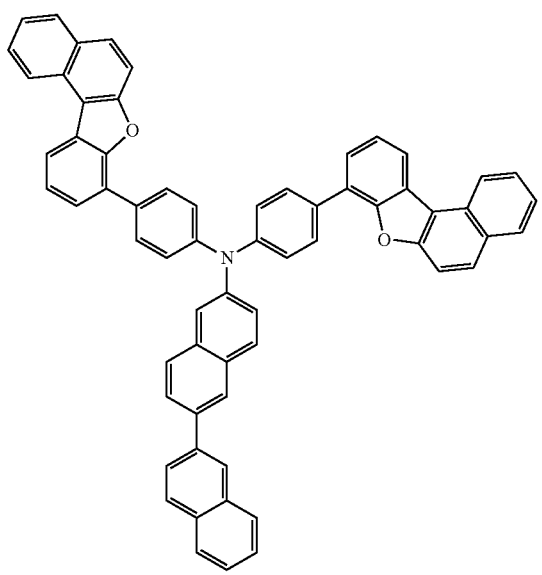
(129)
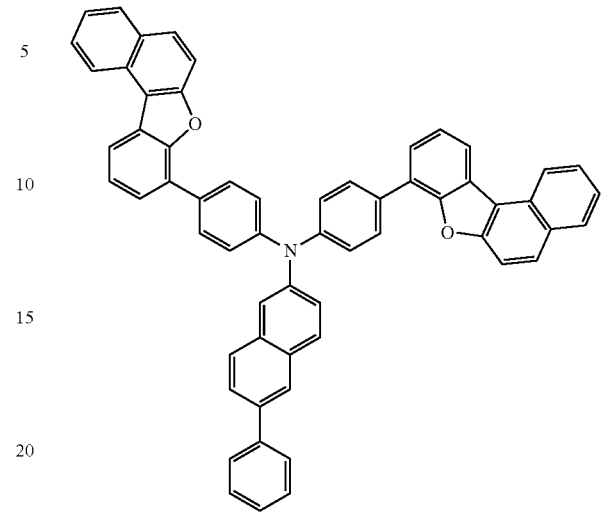
(130)
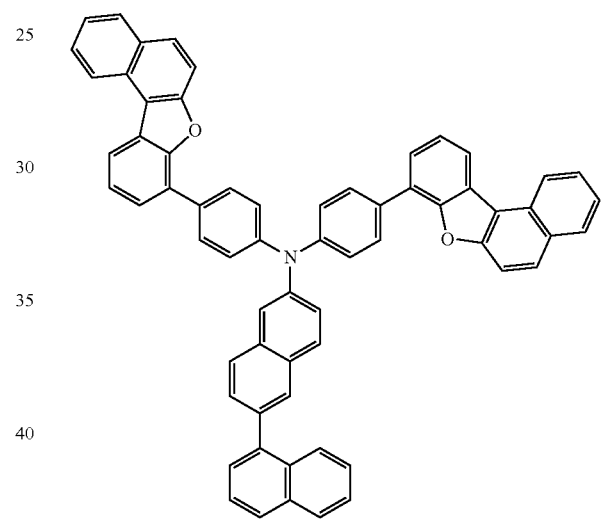
(131)
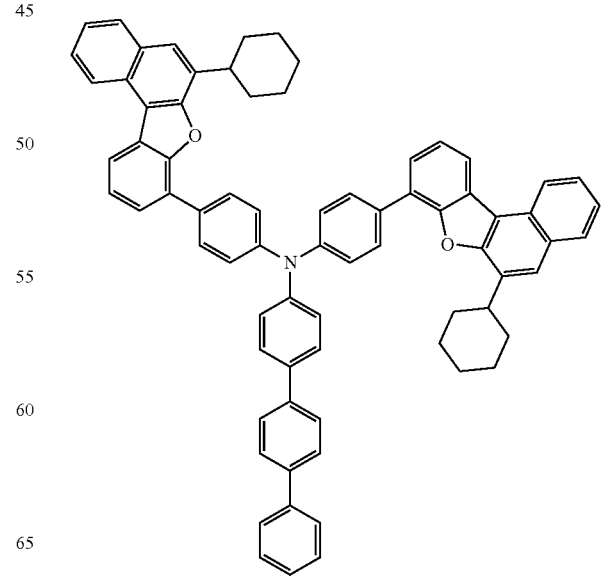

(132)
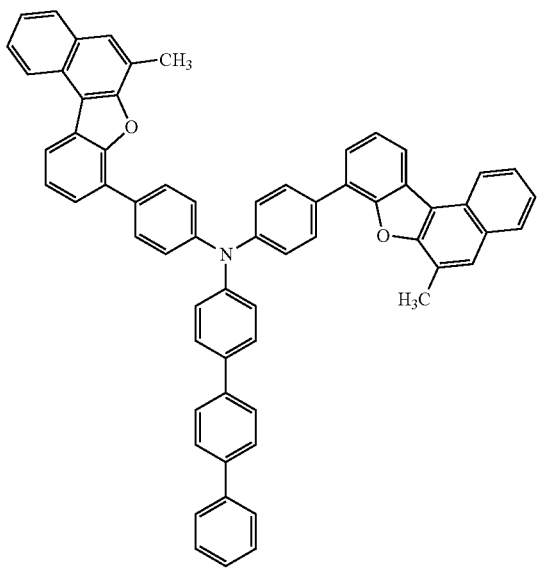
(135)
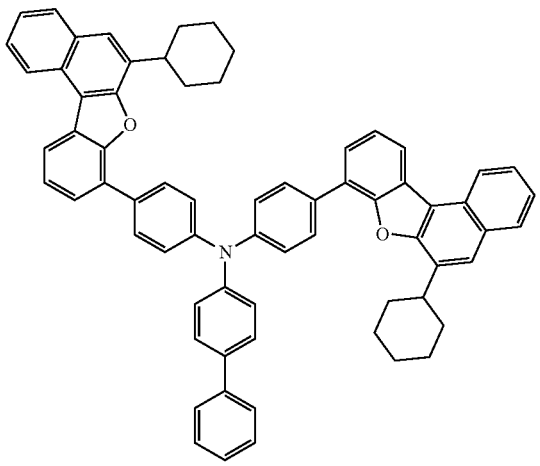
(133)
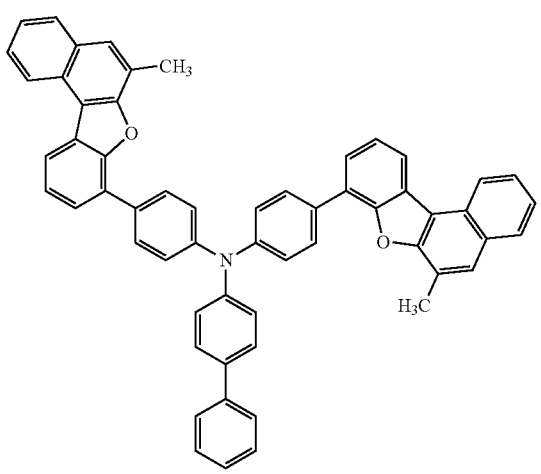
(136)
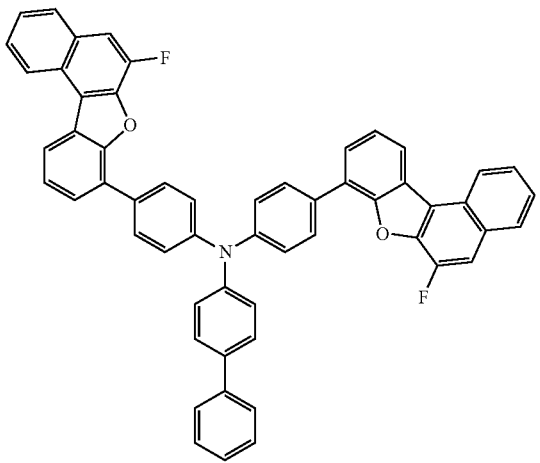
(134)
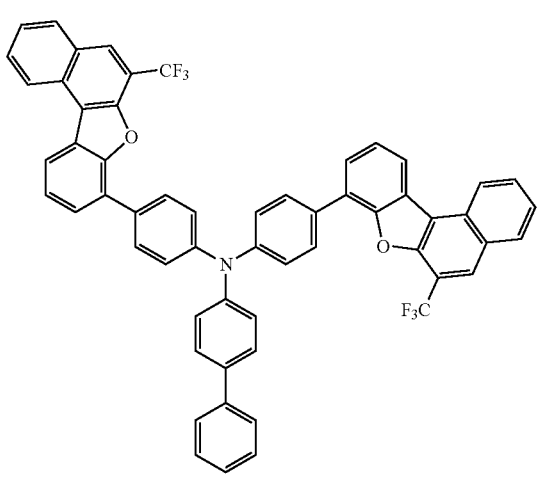
(137)
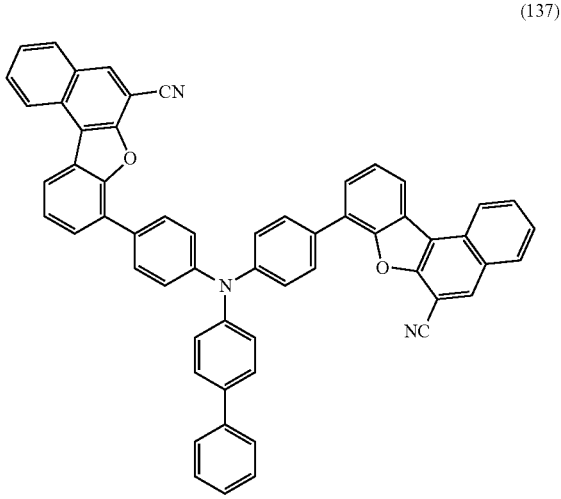

(138)
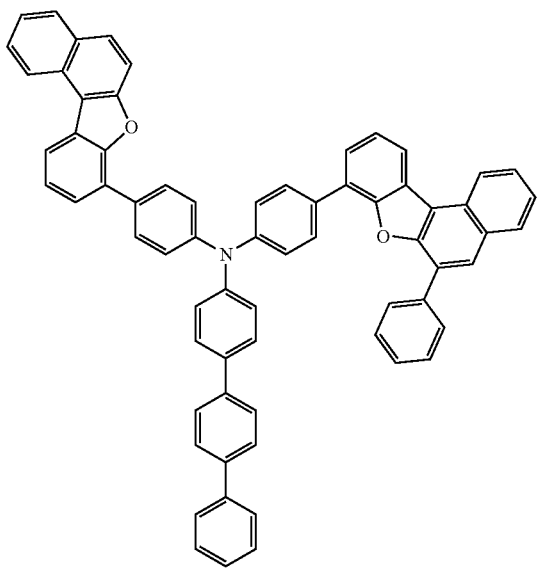
(139)
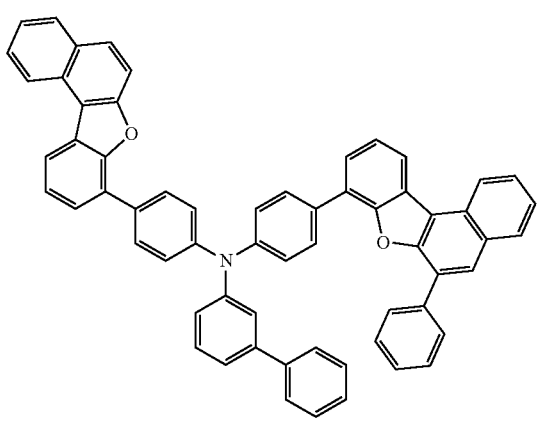
(140)
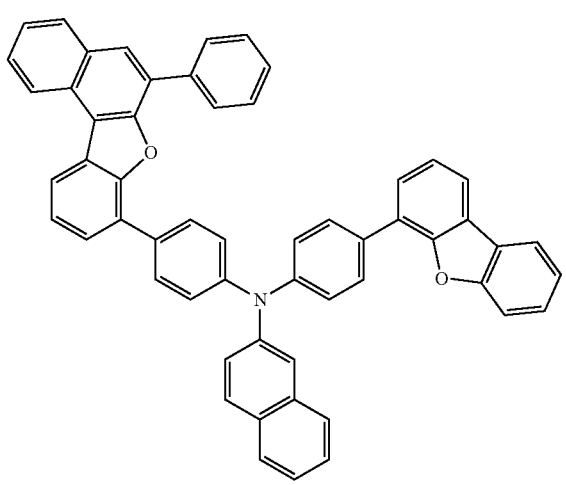
(141)
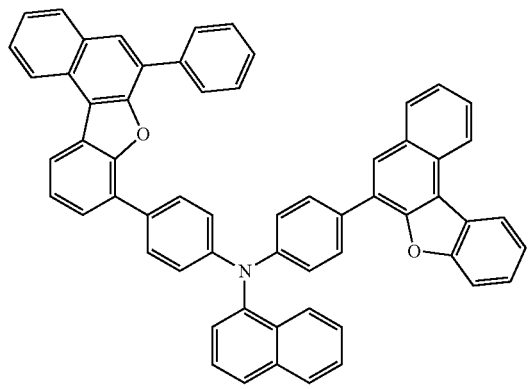
(142)
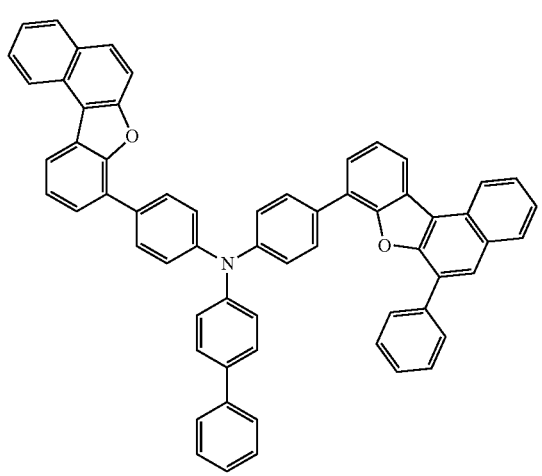
(143)
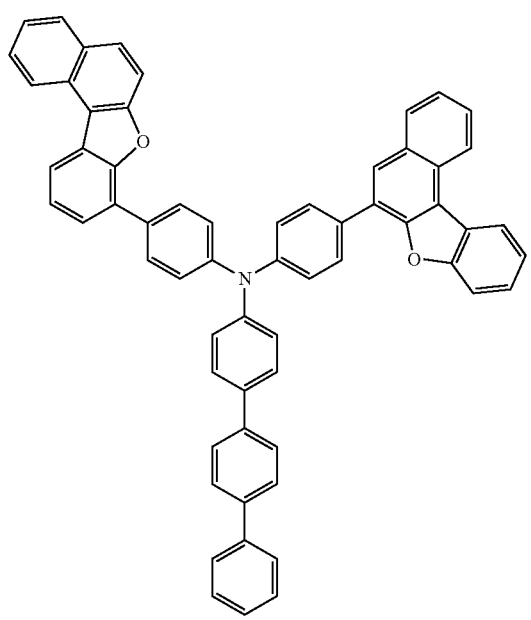

(144)
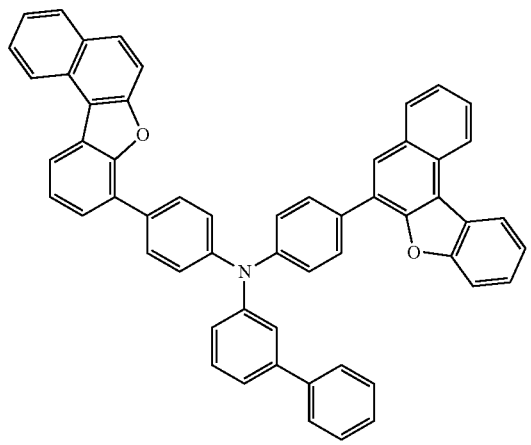
(145)
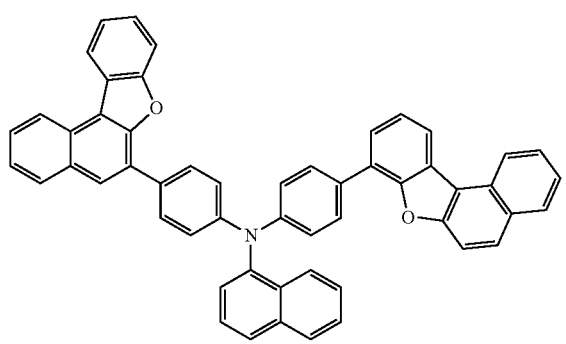
(146)
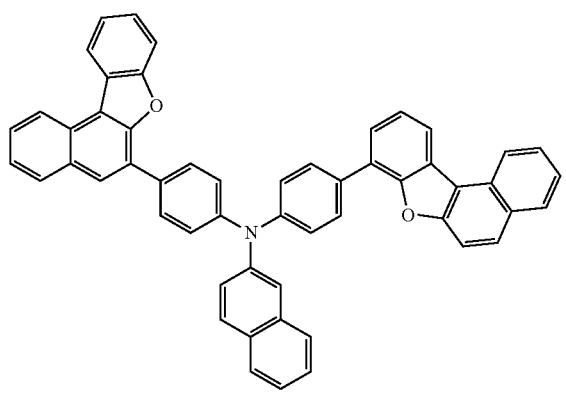
(147)
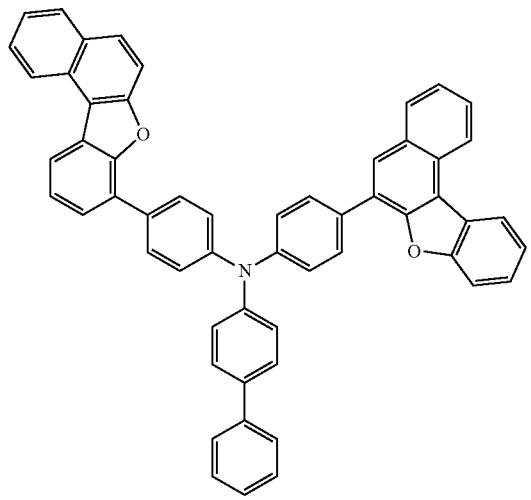
(148)
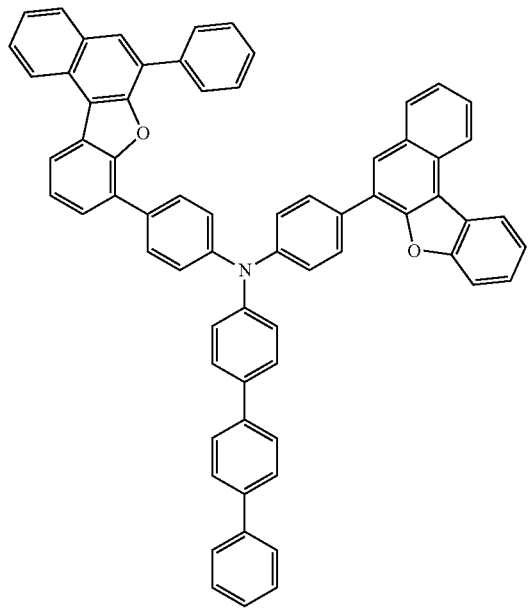
(149)
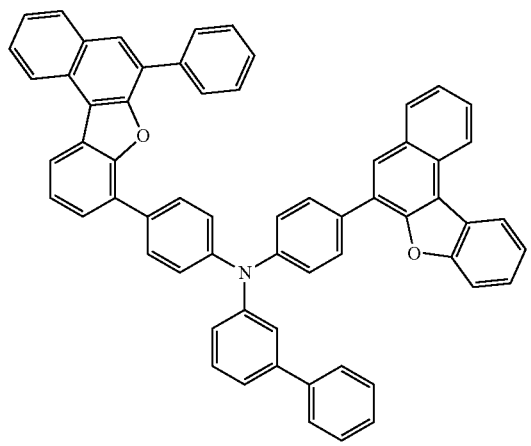

(150)

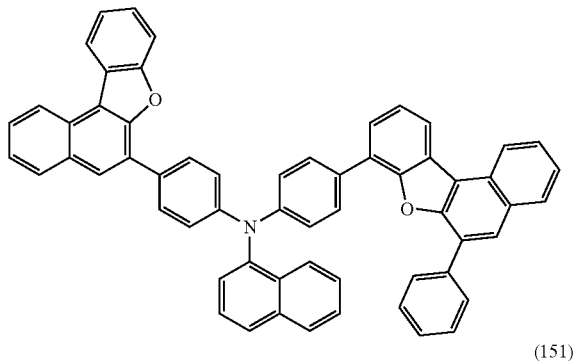

(151)

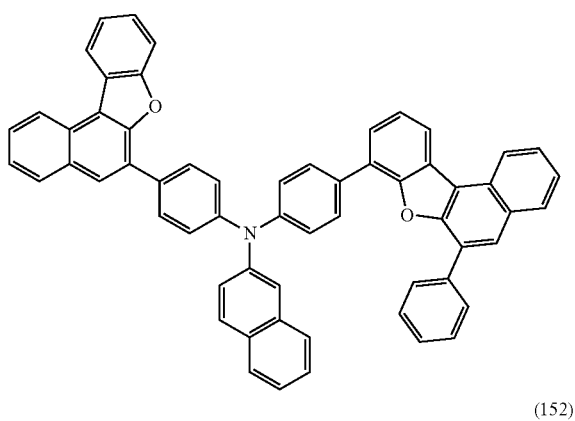

(152)

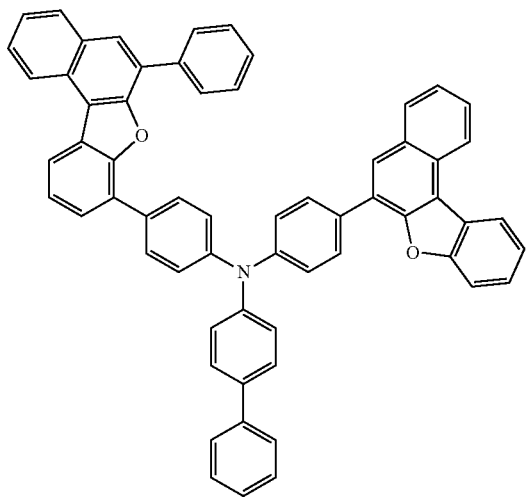

In the organic compound of one embodiment of the present invention, distribution of π conjugated systems spreads to the benzo[b]naphtho[1,2-d]furan skeleton, which is the bulky substituent in the organic compound; thus, the organic compound has an excellent carrier-transport property. Accordingly, a light-emitting element including the organic compound can be driven at a low voltage. In addition, the organic compound has a wide band gap; thus, a light-emitting element including the organic compound can have high emission efficiency.

The lifetime of a light-emitting element including an organic compound is particularly affected by the properties of a hole-transport material in some cases. In particular, the transporting properties of the hole-transport material have considerable influence on the lifetime of the element, which differs significantly according to the type of hole-transport material.

As a hole-transport material, a compound in which π conjugated systems spread over a molecule is generally used. A typical example of the compound is an aromatic amine compound. In general, an aromatic amine compound containing π conjugated systems has uneven charge distribution in a molecule; thus, an aromatic amine compound has a high hole-transport property and can be suitably used as a hole-transport material. In recent years, a variety of aromatic amine compounds have been developed.

Note that the oxidation-reduction characteristics, distribution of π conjugated systems, charge density, and the like in an aromatic amine compound depend on the properties of an aromatic skeleton and a position where an aromatic skeleton and an amine skeleton are bonded to each other. Thus, the selection of an aromatic skeleton and bonding position is extremely important in development of a hole-transport material.

The present inventors have found that an aromatic amine compound including two benzo[b]naphtho[1,2-d]furan skeletons has a high hole-transport property and contributes to an increase in lifetime of a light-emitting element including the organic compound in a hole-transport layer.

A benzonaphthofuran skeleton is preferably a benzo[b]naphtho[1,2-d]furan skeleton, in which case synthesis and purification of benzonaphthofuran can be facilitated and performed at lower cost.

In particular, it is preferable to use an organic compound in which two benzo[b]naphtho[1,2-d]furan skeletons bonded to an arylene group at the 8- or 6-position are included in one molecule and the benzo[b]naphtho[1,2-d]furan skeletons are each bonded to an amine skeleton through the arylene group. It is further preferable to use an organic compound in which two benzo[b]naphtho[1,2-d]furan skeletons bonded to an arylene group at the 8-position are included in one molecule and the benzo[b]naphtho[1,2-d]furan skeletons are each bonded to an amine skeleton through the arylene group.

With such a structure, distribution of π conjugated systems spreads to a benzo[b]naphtho[1,2-d]furan skeleton, which is a bulky substituent; thus, the organic compound has an excellent carrier-transport property and a light-emitting element including the organic compound can be driven at a low voltage.

In general, a HOMO level of an organic compound including a triphenylamine skeleton is approximately −5.3 eV; however, a HOMO level of the organic compound in which two benzo[b]naphtho[1,2-d]furan skeletons bonded to an arylene group at the 8-position are included in one molecule and the benzo[b]naphtho[1,2-d]furan skeletons are each bonded to an amine skeleton through the arylene group is approximately −5.5 eV. This is because distribution of the HOMO in the organic compound having such a structure is wider than that of the HOMO in the general organic compound including a triphenylamine skeleton.

As described above, the HOMO level of the organic compound in which two benzo[b]naphtho[1,2-d]furan skeletons bonded to an arylene group at the 8-position are included in one molecule and the benzo[b]naphtho[1,2-d] furan skeletons are each bonded to an amine skeleton through the arylene group is lower than that of the general organic compound including a triphenylamine skeleton. Thus, the organic compound of one embodiment of the present invention is preferably used in a hole-transport layer of a light-emitting element because a barrier for hole injection between a light-emitting layer and the hole-transport layer can be reduced and the driving voltage of the light-emitting element can be reduced.

An arylene group and a benzo[b]naphtho[1,2-d]furan skeleton are preferably bonded to each other at the 8-position because the organic compound of one embodiment of the present invention can have a high T1 level.

In the case where an arylene group that connects a nitrogen atom and a benzo[b]naphtho[1,2-d]furan skeleton to each other is a phenylene group, the nitrogen atom and the benzo[b]naphtho[1,2-d]furan skeleton are preferably bonded to the phenylene group at the para-position. With such a structure, distribution of π conjugated systems spreads to the benzo[b]naphtho[1,2-d]furan skeleton, which is a bulky substituent; thus, the organic compound of one embodiment of the present invention has an excellent carrier-transport property.

As described above, since the organic compound of one embodiment of the present invention is an aromatic amine compound, the organic compound has a high hole-transport property. In addition, the organic compound of one embodiment of the present invention has a wide band gap; thus, a light-emitting element including the organic compound can have high emission efficiency. A light-emitting element including the organic compound in a hole-transport layer has a high proportion of recombination of holes and electrons (also referred to as a carrier balance) in an EL layer and can suppress diffusion of excitons from a light-emitting layer; thus, a light-emitting element with high emission efficiency and long lifetime can be provided.

Therefore, the organic compound of one embodiment of the present invention is suitable as a material used for a hole-transport layer of a light-emitting element. In addition, the organic compound can be used as a host material in a light-emitting layer.

One of the important properties required for an organic compound used for a light-emitting element is heat resistance. When the glass transition point (Tg) of a material is used as an index, a material with higher Tg can be regarded as having higher heat resistance. In general, a material with higher molecular mass tends to have higher Tg. Thus, the molecular mass needs to be increased to improve heat resistance of a material.

The molecular mass of an organic compound can be increased by introducing an aromatic hydrocarbon group such as a phenyl group or a naphthyl group or increasing the number of condensed aromatic rings, for example. However, in some cases, these methods cause problems such as a decrease in T1 level of an organic compound and a decrease in carrier-transport property, which depends on a bonding position of a substituent.

Although the organic compound of one embodiment of the present invention includes a plurality of aromatic hydrocarbon groups and a benzo[b]naphtho[1,2-d]furan skeleton that has a fused structure in a molecule and high molecular mass, the organic compound has a high carrier-transport property and a high T1 level.

In order to obtain such properties, a structure in which two benzo[b]naphtho[1,2-d]furan skeletons bonded to an arylene group at the 8- or 6-position are included in one molecule and the benzo[b]naphtho[1,2-d]furan skeletons are each bonded to an amine skeleton through the arylene group is preferable. A structure in which two benzo[b]naphtho[1,2-d]furan skeletons bonded to an arylene group at the 8-position are included in one molecule and the benzo[b]naphtho[1,2-d]furan skeletons are each bonded to an amine skeleton through the arylene group is further preferable.

Note that when a benzo[b]naphtho[1,2-d]furan skeleton bonded to an arylene group at the 8-position includes a substituent, the substituent is preferably bonded at the 6-position. When the substituent is bonded to the benzo[b]naphtho[1,2-d]furan skeleton at the 6-position, the molecular mass can be increased without a decrease in carrier-transport property and a decrease in T1 level.

Note that an organic compound with a high molecular mass generally tends to have a high glass transition point (Tg). However, because of the improved heat resistance, the sublimation temperature or boiling point in sublimation purification or distillation performed in a purification step also tends to be high. Simply increasing molecular mass increases the sublimation temperature or boiling point. Accordingly, higher temperatures are needed in a film formation step such as deposition by evaporation, or a purification step such as sublimation purification or distillation, and decomposition might be caused.

That is, simply increasing the molecular mass of an organic compound to improve its thermophysical properties increases the possibility of decomposition in a purification step or a film formation step, which sometimes makes it difficult to use a highly purified organic compound for an element.

In contrast, the organic compound of one embodiment of the present invention has a structure in which two benzo[b]naphtho[1,2-d]furan skeletons bonded to an arylene group at the 8- or 6-position are included in one molecule and the benzo[b]naphtho[1,2-d]furan skeletons are each bonded to an amine skeleton through the arylene group; thus, the decomposition temperature of the organic compound is high even though the molecular mass is high. Therefore, decomposition does not easily occur in a purification step or an evaporation step and the material maintaining high purity can be used for an element. That is, an element having both high heat resistance and excellent properties can be provided.

A film of the organic compound of this embodiment can be formed by an evaporation method (including a vacuum evaporation method), an inkjet method, a coating method, gravure printing, or the like.

This embodiment can be combined with any of the other embodiments as appropriate.

Embodiment 2

In this embodiment, a method for synthesizing the organic compound of one embodiment of the present invention represented by General Formula (G0) is described.

(G0)

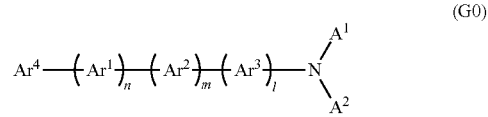

In General Formula (G0), $Ar^1$, $Ar^2$, and $Ar^3$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, and n, 171, and 1 independently represent an integer of 0 or 1. In addition, $A^1$ and $A^2$ independently represent a group represented by General Formula (g0) or (g1).

(g0)

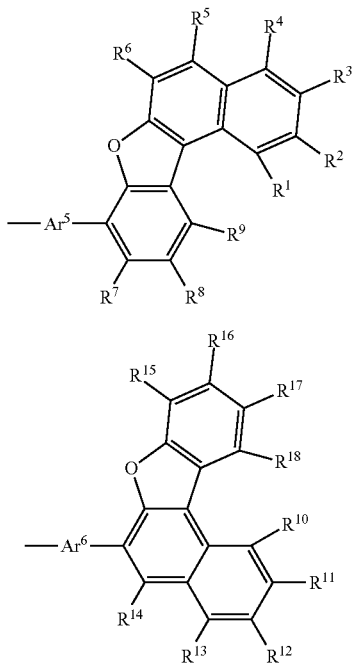

(g1)

In General Formulae (g0) and (g1), $Ar^5$ and $Ar^6$ independently represent a substituted or unsubstituted divalent aromatic hydrocarbon group having 6 to 13 carbon atoms. In addition, $R^1$ to $R^{18}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 25 carbon atoms. The organic compound is useful in terms of simplicity of the synthesis and synthesis cost.

The organic compound of one embodiment of the present invention represented by General Formula (G0) can be synthesized by Synthesis Scheme (a-1) when $A^1$ and $A^2$ have the same structure. That is, an aromatic amine compound (compound 1) is coupled with a compound including a benzo[b]naphtho[1,2-d]furanyl group (compound 2), whereby an objective substance (G0-a) can be obtained. Synthesis Scheme (a-1) is shown below.

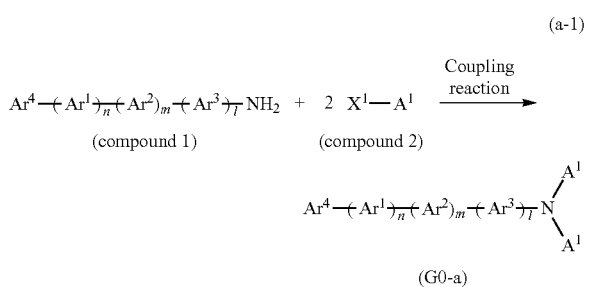

(a-1)

In Synthesis Scheme (a-1), $Ar^1$ to $Ar^3$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, n, m, and l independently represent an integer of 0 or 1, and $X^1$ represents chlorine, bromine, iodine, or a triflate group. In addition, $A^1$ represents a group represented by General Formula (g0) or (g1).

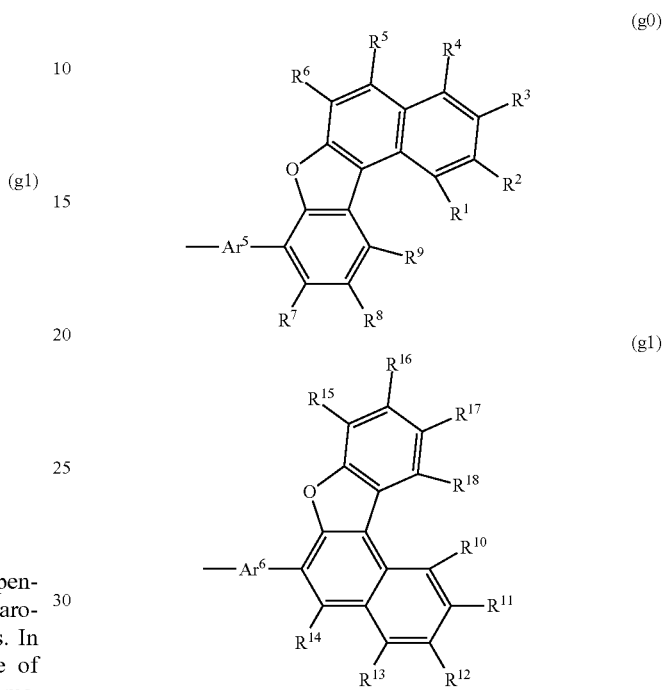

(g0)

(g1)

In General Formulae (g0) and (g1), $Ar^5$ and $Ar^6$ independently represent a substituted or unsubstituted divalent aromatic hydrocarbon group having 6 to 13 carbon atoms. In addition, $R^1$ to $R^{18}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 25 carbon atoms.

In Synthesis Scheme (a-1), the Buchwald-Hartwig reaction using a palladium catalyst can be performed. In the case where the reaction is performed, a palladium compound such as bis(dibenzylideneacetone)palladium(0), palladium (II) acetate, [1,1-bis(diphenylphosphino)ferrocene]palladium(II) dichloride, tetrakis(triphenylphosphine)palladium (0), or allylpalladium(II) chloride (dimer) and a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, tri(ortho-tolyl) phosphine, or (S)-(6,6'-dimethoxybiphenyl-2,2'-diyl)bis (diisopropylphosphine) (abbreviation: cBRIDP (registered trademark)) can be used, for example. In the reaction, an organic base such as sodium tert-butoxide, an inorganic base such as potassium carbonate, cesium carbonate, or sodium carbonate, or the like can be used. Furthermore, in the reaction, toluene, xylene, benzene, tetrahydrofuran, dioxane, or the like can be used as a solvent. The reagents that can be used in the reaction are not limited to the above reagents.

In the case where the Ullmann reaction is performed in Synthesis Scheme (a-1), examples of a reagent that can be used in the reaction include copper and a copper compound, and examples of a base include an inorganic base such as potassium carbonate. Examples of the solvent that can be used in the reaction include 1,3-dimethyl-3,4,5,6-tetrahydro-2(1H)pyrimidinone (DMPU), toluene, xylene, and benzene. In the Ullmann reaction, since the objective substance can be obtained in a shorter time and in a higher yield when the reaction temperature is 100° C. or higher; therefore, it is preferable to use DMPU or xylene that has a high boiling point. A reaction temperature of 150° C. or higher is further preferred and accordingly DMPU is more preferably used. The reagents that can be used in the reaction are not limited to the above reagents.

In the case where $A^1$ and $A^2$ in the organic compound of one embodiment of the present invention represented by General Formula (G0) have different structures from each other, the organic compound can be synthesized by performing reaction in two steps with a compound including $A^1$ or $A^2$ skeleton (compound 2 or compound 4) as shown in Synthesis Schemes (b-1) and (b-2). The reaction performed in two steps makes it possible to obtain a compound in which the structures of $A^1$ and $A^2$ are different from each other.

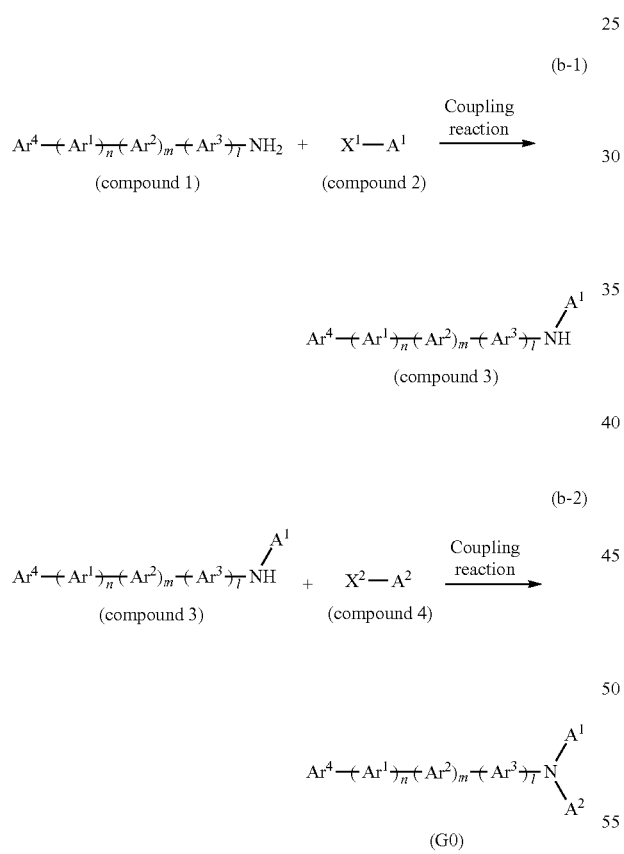

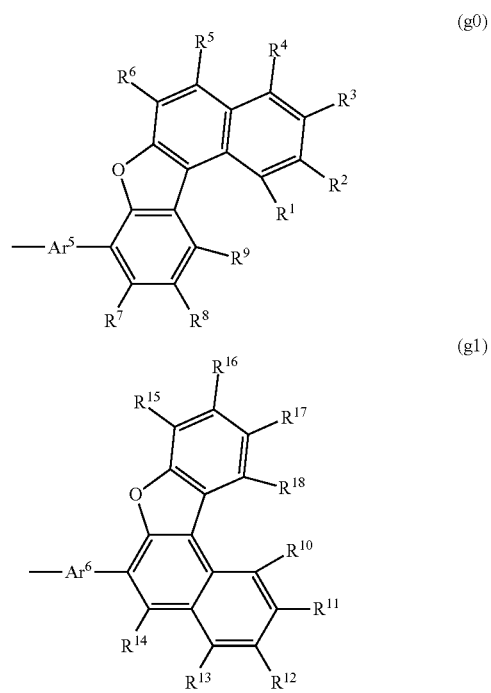

In General Formulae (g0) and (g1), $Ar^5$ and $Ar^6$ independently represent a substituted or unsubstituted divalent aromatic hydrocarbon group having 6 to 13 carbon atoms. In addition, $R^1$ to $R^{18}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 25 carbon atoms.

In Synthesis Schemes (b-1) and (b-2), the Buchwald-Hartwig reaction or the Ullmann reaction can be performed. Reagents that can be used in each reaction are similar to those in Synthesis Scheme (a-1).

A method for synthesizing the organic compound of one embodiment of the present invention represented by General Formula (G0), which is different from the above, is described. A synthesis method for performing amination is described above, and here, a synthesis method using a triarylamine compound as a source material is described. A triaryl compound (compound 5) is coupled with two equivalents of a benzo[b]naphtho[1,2-d]furan compound (compound 6), whereby an objective compound (G0-b) can be obtained.

In Synthesis Schemes (b-1) and (b-2), $Ar^1$ to $Ar^3$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, n, m, and l independently represent an integer of 0 or 1, and $X^1$ and $X^2$ independently represent chlorine, bromine, iodine, or a triflate group. In addition, $A^1$ and $A^2$ each represent a group represented by General Formula (g0) or (g1).

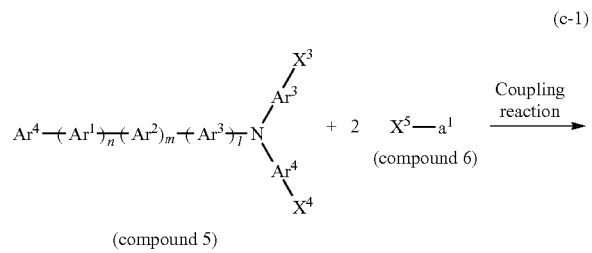

-continued

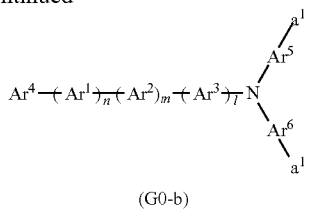

(G0-b)

In Synthesis Scheme (c-1), $Ar^1$ to $Ar^3$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, n, m, and l independently represent an integer of 0 or 1, and $X^3$ to $X^5$ represent a halogen group, a boronic acid group, an organoboron group, or a triflate group. In addition, $a^1$ represents a group represented by General Formula (g0-1) or (g1-1).

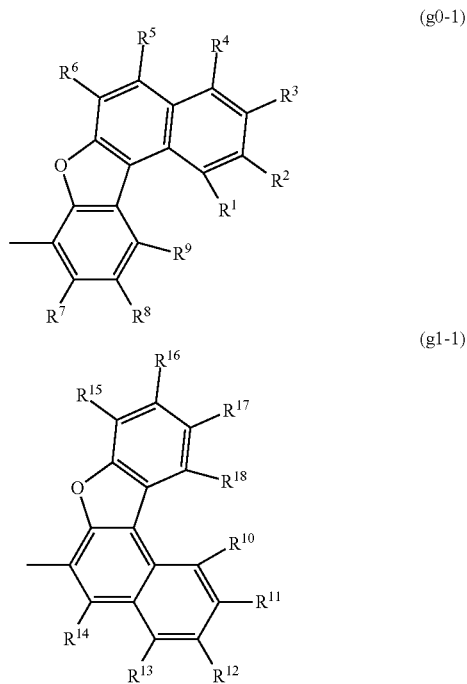

In General Formulae (g0-1) and (g1-1), $R^1$ to $R^{18}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 25 carbon atoms.

When a Suzuki-Miyaura coupling reaction using a palladium catalyst is performed in Synthesis Scheme (c-1), $X^3$ to $X^5$ independently represent a halogen group, a boronic acid group, an organoboron group, or a triflate group, and halogen is preferably iodine, bromine, or chlorine. In the reaction, a palladium compound such as bis(dibenzylideneacetone)palladium(0), palladium(II) acetate, [1,1-bis(diphenylphosphino)ferrocene]palladium(II) dichloride, or tetrakis(triphenylphosphine)palladium(0) and a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, or tri(ortho-tolyl)phosphine can be used. In the reaction, an organic base such as sodium tert-butoxide, an inorganic base such as potassium carbonate, cesium carbonate, or sodium carbonate, or the like can be used. Furthermore, in the reaction, toluene, xylene, benzene, tetrahydrofuran, dioxane, ethanol, methanol, water, or the like can be used as a solvent. The reagents that can be used in the reaction are not limited to the above reagents.

The reaction performed in Synthesis Scheme (c-1) is not limited to a Suzuki-Miyaura coupling reaction, and a Migita-Kosugi-Stille coupling reaction using an organotin compound, a Kumada-Tamao-Corriu coupling reaction using a Grignard reagent, a Negishi coupling reaction using an organozinc compound, a reaction using copper or a copper compound, or the like can also be employed. In the case of using the Migita-Kosugi-Stille coupling reaction, when $X^3$ and $X^4$ each represent an organotin group, $X^5$ represents a halogen group and vice versa. That is, one of the compounds 5 and 6 represents an organotin compound and the other represents halide. In the case of using the Kumada-Tamao-Corriu coupling reaction, when $X^3$ and $X^4$ each represent a magnesium halide group, $X^5$ represents a halogen group and vice versa. That is, one of the compounds 5 and 6 represents a Grignard reagent and the other represents halide. In the case of using the Negishi coupling reaction, when $X^3$ and $X^4$ each represent an organozinc group, $X^5$ represents a halogen group and vice versa. That is, one of the compounds 5 and 6 represents an organozinc compound and the other represents halide.

In the case where $A^1$ and $A^2$ in the organic compound of one embodiment of the present invention represented by General Formula (G0) have different structures from each other, the organic compound can be synthesized by performing reaction in two steps with a compound including $a^1$ or $a^2$ (compound 6 or compound 8) as shown in Synthesis Schemes (d-1) and (d-2). The reaction performed in two steps makes it possible to obtain a compound in which the structures of $A^1$ and $A^2$ are different from each other.

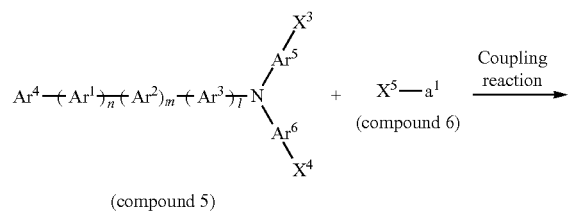

(compound 5)   (compound 6)

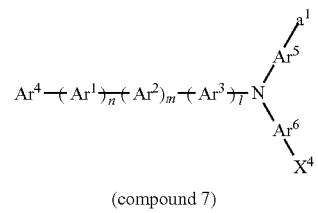

(compound 7)

-continued

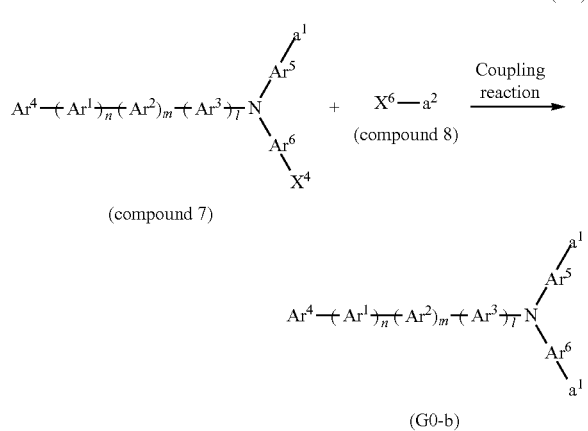

(d-2)

(compound 7)

(G0-b)

In Synthesis Schemes (d-1) and (d-2), $Ar^1$ to $Ar^3$ independently represent a substituted or unsubstituted divalent aromatic hydrocarbon group having 6 to 25 carbon atoms, $Ar^4$ represents a substituted or unsubstituted aromatic hydrocarbon group having 6 to 25 carbon atoms, n, in, and l independently represent an integer of 0 or 1, and $X^3$ to $X^6$ represent a halogen group, a boronic acid group, an organoboron group, or a triflate group. In addition, $a^1$ and $a^2$ each represent a group represented by General Formula (g0-1) or (g1-1).

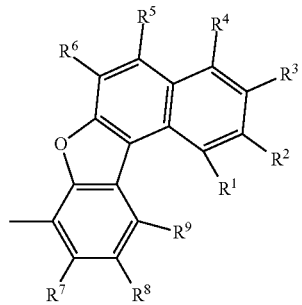

(g0-1)

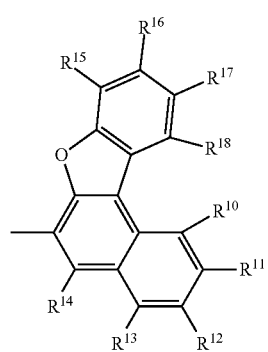

(g1-1)

In General Formulae (g0-1) and (g1-1), $R^1$ to $R^{18}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 25 carbon atoms.

In Synthesis Schemes (d-1) and (d-2), as in Synthesis Scheme (c-1), reaction such as the Suzuki-Miyaura coupling reaction, the Migita-Kosugi-Stille coupling reaction, the Kumada-Tamao-Corriu coupling reaction using a Grignard reagent, the Negishi coupling reaction using an organozinc compound, or a reaction using copper or a copper compound can be employed. In the case of using the Migita-Kosugi-Stille coupling reaction, when $X^3$ and $X^4$ each represent an organotin group, $X^5$ and $X^6$ each represent a halogen group and vice versa. That is, one of the compounds 5 and 6 represents an organotin compound and the other represents halide. In addition, one of the compounds 7 and 8 represents an organotin compound and the other represents halide. In the case of using the Kumada-Tamao-Corriu coupling reaction, when $X^3$ and $X^4$ each represent a magnesium halide group, $X^5$ and $X^6$ each represent a halogen group and vice versa. That is, one of the compounds 5 and 6 represents a Grignard reagent and the other represents halide. In addition, one of the compounds 7 and 8 represents a Grignard reagent and the other represents halide. In the case of using the Negishi coupling reaction, when $X^3$ and $X^4$ each represent an organozinc group, $X^5$ and $X^6$ each represent a halogen group and vice versa. That is, one of the compounds 5 and 6 represents an organozinc compound and the other represents halide. In addition, one of the compounds 7 and 8 represents an organozinc compound and the other represents halide.

Note that in the synthesis of the organic compound of one embodiment of the present invention represented by General Formula (G0), the synthesis method is not limited to Synthesis Schemes (a-1) to (d-2).

Embodiment 3

In this embodiment, structure examples of light-emitting elements including an organic compound of one embodiment of the present invention are described below with reference to FIGS. 1A to 1D and FIGS. 2A to 2C.

FIG. 1A is a cross-sectional view of a light-emitting element 100 of one embodiment of the present invention. The light-emitting element 100 includes at least a pair of electrodes (an electrode 101 and an electrode 102) and an EL layer 103 provided between the pair of electrodes.

The EL layer 103 includes at least a light-emitting layer 113 and a hole-transport layer 112. In addition, the EL layer 103 includes functional layers such as a hole-injection layer 111, an electron-transport layer 114, and an electron-injection layer 115.

Although description is given assuming that the electrode 101 serves as an anode and the electrode 102 serves as a cathode in this embodiment, the structure of the light-emitting element is not limited thereto. That is, it is possible that the electrode 101 serves as a cathode and the electrode 102 serves as an anode. In that case, the stacking order of layers is reversed. In other words, the hole-injection layer, the hole-transport layer, the light-emitting layer, the electron-transport layer, and the electron-injection layer may be stacked in this order from the anode side.

The structure of the EL layer 103 is not limited to the above, and the EL layer 103 may include a functional layer that is capable of improving or inhibiting a hole- or electron-transport property, or suppressing diffusion of excitons, for example. The functional layers may each be a single layer or stacked layers.

In the light-emitting element 100, at least one of the layers in the EL layer 103 contains the organic compound of one embodiment of the present invention. Note that the organic compound is contained preferably in the light-emitting layer 113, further preferably in the hole-transport layer 112.

In the case where the organic compound of one embodiment of the present invention is contained in the light-emitting layer 113, the organic compound can be used as a host material because the organic compound has a high hole-transport property and a wide band gap.

In the case where the organic compound of one embodiment of the present invention is contained in the hole-transport layer 112, a light-emitting element with high emission efficiency and long lifetime can be provided because the organic compound has a high hole-transport property and a wide band gap. In particular, the organic compound is preferably used in the case where the hole-injection layer 111 is provided between the hole-transport layer 112 and the electrode 101 and includes an organic compound having an acceptor property, which facilitates the injection of holes from the electrode.

Structure Example 1 of Light-Emitting Element

In the case where the injection of holes is performed using the organic compound having an acceptor property, a compound contained in the hole-transport layer 112 in contact with the hole-injection layer 111 is preferably a hole-transport material with a relatively high HOMO level in order to facilitate the extraction of electrons by the organic compound having an acceptor property. However, holes cannot be easily injected into the light-emitting layer 113 from the hole-transport material with a high HOMO level. When the light-emitting layer 113 is formed in contact with the hole-transport layer 112 made of the hole-transport material with a high HOMO level, carriers are accumulated at their interface, which might cause a decrease in lifetime and efficiency of the light-emitting element. Thus, a layer containing the organic compound of one embodiment of the present invention is provided between the light-emitting layer 113 and the hole-transport material with a high HOMO level, in which case holes can be easily injected into the light-emitting layer and the lifetime and efficiency of the light-emitting element can be improved.

A structure of a light-emitting element in this case is described with reference to FIGS. 1B to 1D. Here, the case where an organic compound having an acceptor property is used as a hole-injection material 131 and a LUMO level of the hole-injection material 131 is lower than the HOMO level of a first hole-transport material 132 is described. The correlation of HOMO levels and a LUMO level of the materials in this case is schematically shown in FIG. 1D. What terms and numerals in FIGS. 1C and 1D represent are listed below.

HIM (131): the hole-injection material 131;
HTM (132): the first hole-transport material 132;
HTM (133): a second hole-transport material 133;
HTM (134): a third hole-transport material 134;
Host (135): a host material 135; and a guest material 136.

Figure 1B:
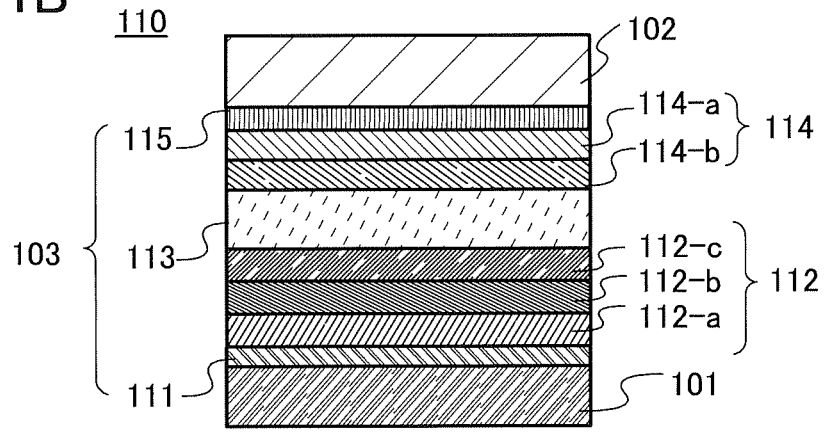
Figure 1C:
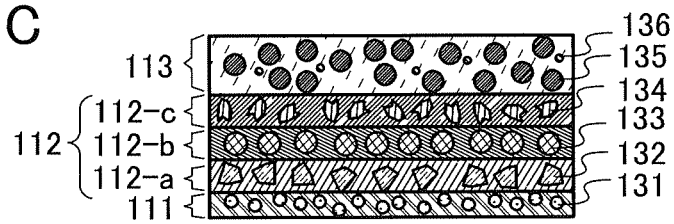
Figure 1D:
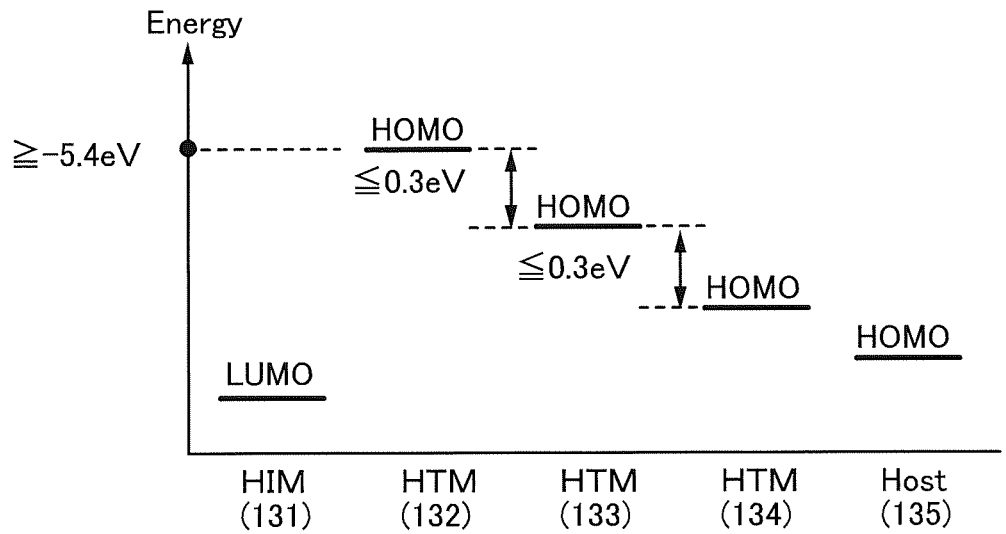
FIG. 1D shows a correlation between a highest occupied molecular orbital (also referred to as HOMO) level and a lowest unoccupied molecular orbital (also referred to as LUMO) level of an EL layer.

As illustrated in FIG. 1B, the hole-transport layer 112 may have a stacked-layer structure of a plurality of layers. Specifically, a structure in which the hole-transport layer 112 includes a first hole-transport layer 112-*a* containing the first hole-transport material 132 and a second hole-transport layer 112-*b* containing the second hole-transport material 133 from the hole-injection layer 111 side may be employed. The organic compound of one embodiment of the present invention may be used as the second hole-transport material 133. In the case of such a structure, the HOMO level of the second hole-transport material 133 is lower than that of the first hole-transport material 132, achieving a light-emitting element with a long lifetime and a high efficiency. Note that the HOMO level of the first hole-transport material 132 is preferably greater than or equal to −5.4 eV, in which case electrons can be easily extracted from the hole-injection material 131 (see FIG. 1D).

As shown in FIG. 1D, the difference between the HOMO level of the first hole-transport material 132 and the HOMO level of the second hole-transport material 133 is preferably less than or equal to 0.3 eV, further preferably less than or equal to 0.2 eV, in which case holes can be easily injected from the first hole-transport layer 112-*a* to the second hole-transport layer 112-*b*. The HOMO level of the organic compound of one embodiment of the present invention is approximately −5.5 eV; thus, the organic compound can be suitably used as the second hole-transport material 133.

The hole-transport layer 112 may further include a third hole-transport layer 112-*c* between the second hole-transport layer 112-*b* and the light-emitting layer 113, and the third hole-transport layer 112-*c* may contain a third hole-transport material 134 (see FIGS. 1B and 1C). In that case, as shown in FIG. 1D, the HOMO level of the third hole-transport material 134 is preferably lower than the HOMO level of the hole-transport material of one embodiment of the present invention contained in the second hole-transport layer 112-*b*, and the difference in the HOMO level is preferably less than or equal to 0.3 eV, further preferably less than or equal to 0.2 eV. The HOMO level of the organic compound of one embodiment of the present invention is approximately −5.5 eV; thus, the organic compound can be suitably used as the third hole-transport material 134.

The HOMO level of the third hole-transport material 134 is preferably lower than or equal to the HOMO level of the host material 135, in which case holes are suitably transported to the light-emitting layer to increase the lifetime and efficiency.

Note that in FIG. 1D, the LUMO level of the hole-injection material 131 is lower than the HOMO level of the host material 135; however, there is no limitation on the relationship therebetween. That is, the LUMO level of the hole-injection material 131 may be higher than or equal to the HOMO level of the host material 135. Furthermore, it is possible that the HOMO level of the host material 135 is higher than the HOMO level of the first hole-transport material 132, the HOMO level of the host material 135 is higher than the HOMO level of the second hole-transport material 133, and the HOMO level of the host material 135 is higher than the HOMO level of the third hole-transport material 134. In addition, the HOMO level of the first hole-transport material 132 may be lower than the HOMO level of the second hole-transport material 133. In addition, the HOMO level of the second hole-transport material 133 may be lower than the HOMO level of the third hole-transport material 134. In addition, the HOMO level of the first hole-transport material 132 may be lower than the HOMO level of the third hole-transport material 134.

Note that in the case where the HOMO level of the guest material 136 is higher than the HOMO level of the host material 135, the proportion of holes injected into the guest material 136 increases according to the position of the HOMO level of the hole-transport layer, and furthermore, the holes are trapped in the guest material 136, which might cause a decreased lifetime due to the light-emitting region unevenly placed. The structure of the light-emitting element of the present invention is preferably applied to such a case, for example, to a blue fluorescent element. In particular, the structure of the present invention is preferably used for an aromatic diamine compound that emits excellent blue fluorescence, more particularly a pyrenediamine compound and the like, achieving a light-emitting element with excellent lifetime, efficiency, and chromaticity.

The electron-transport layer 114 is not necessarily a single layer as illustrated in FIG. 1A, and may have a stacked-layer structure of a plurality of layers. The electron-transport layer 114 may be a mixed film formed of a plurality of materials. Specifically, as illustrated in FIG. 1B, the electron-transport layer 114 may include a first electron-transport layer 114-*b* and a second electron-transport layer 114-*a* from the light-emitting layer 113 side. Such a structure is preferable because the electron-injection property of the electron-injection layer 115 to the electron-transport layer 114-*a* and the electron-transport properties of the electron-transport layer 114-*b* and the electron-transport layer 114-*a* can be adjusted.

Structure Example 2 of Light-Emitting Element

Next, a structure example of the blue fluorescent element is described with reference to FIGS. 2A to 2C.

Figure 2A:
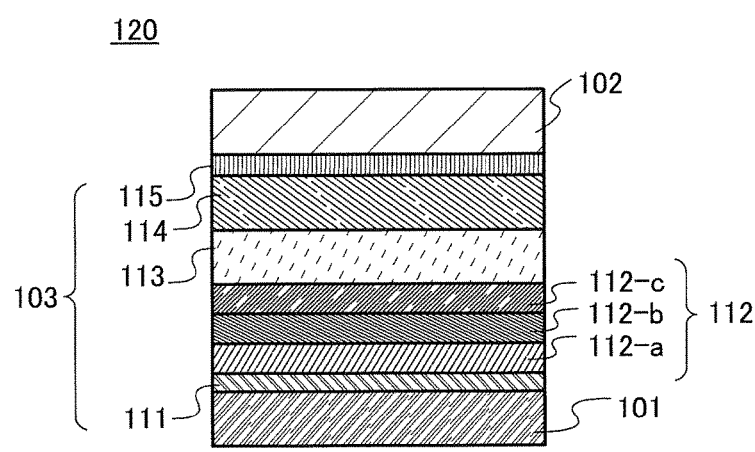
FIGS. 2A and 2B are schematic views of a light-emitting element of one embodiment of the present invention.
Figure 2B:
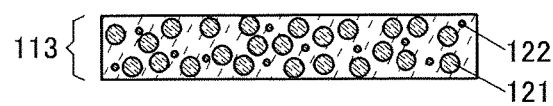

A light-emitting element 120 illustrated in FIG. 2A contains the organic compound of one embodiment of the present invention in at least the hole-transport layer 112. FIG. 2B illustrates a structure example of materials in the light-emitting layer 113. FIG. 2C schematically shows the correlation of energy levels of the materials in the light-emitting layer 113.

Here, the case where a T1 level of a host material 121 is lower than a T1 level of a guest material 122 is described. What terms and numerals in FIG. 2C represent are listed below. Note that the T1 level of the host material 121 may be higher than the T1 level of the guest material 122.

Host (121): the host material 121;
Guest (122): the guest material 122 (the fluorescent material);
$S_{FH}$: the S1 level of the host material 121;
$T_{FH}$: the T1 level of the host material 121;
$S_{FG}$: the S1 level of the guest material 122 (the fluorescent material); and
$T_{FG}$: the T1 level of the guest material 122 (the fluorescent material).

The host material 121 preferably has a function of converting triplet excitation energy into singlet excitation energy by causing triplet-triplet annihilation (TTA), so that the triplet excitation energy which normally does not contribute to fluorescence and is generated in the light-emitting layer 113 can be partly converted into singlet excitation energy in the host material 121. The singlet excitation energy can be transferred to the guest material 122 (see Route $E_1$ in FIG. 2C) and extracted as fluorescence. Accordingly, the emission efficiency of the fluorescent element can be improved. Note that the fluorescence caused by TTA is obtained through a triplet excited state having a long lifetime; thus, delayed fluorescence is observed.

Figure 2C:
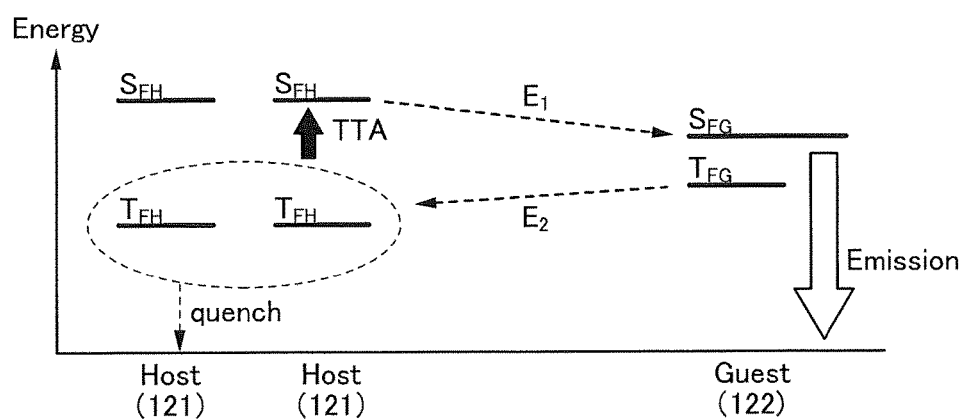
FIG. 2C shows a correlation between energy levels in a light-emitting layer.

In order to transfer the singlet excitation energy to the guest material 122 efficiently in the light-emitting layer 113, the lowest level of the singlet excitation energy (S1 level) of the host material 121 is preferably higher than the S1 level of the guest material 122 as illustrated in FIG. 2C. In addition, the lowest level of the triplet excitation energy (T1 level) of the host material 121 is preferably lower than the T1 level of the guest material 122 (see Route $E_2$ in FIG. 2C). With such a structure, TTA can be efficiently caused in the light-emitting layer 113.

Furthermore, the T1 level of the host material 121 is preferably lower than the T1 level of a material used for the hole-transport layer 112 (the hole-transport layer 112-*c* in FIG. 2A) that is in contact with the light-emitting layer 113. That is, the hole-transport layer 112 preferably has a function of suppressing diffusion of excitons. Such a structure can suppress diffusion of triplet excitons generated in the light-emitting layer 113 to the hole-transport layer 112, so that an element with high emission efficiency can be provided.

The organic compound of one embodiment of the present invention has a high T1 level and a high hole-transport property and thus can be suitably used as a hole-transport material utilizing the TTA in a light-emitting element. Note that the organic compound of one embodiment of the present invention can also be used as the host material 121.

The lowest singlet excitation energy level of an organic compound can be observed from an absorption spectrum at a transition from the singlet ground state to the lowest singlet excited state in the organic compound. Alternatively, the lowest singlet excitation energy level may be estimated from a peak wavelength of a fluorescence spectrum of the organic compound. Furthermore, the lowest triplet excitation energy level can be observed from an absorption spectrum at a transition from the singlet ground state to the lowest triplet excited state in the organic compound, but is difficult to observe in some cases because this transition is a forbidden transition. In such cases, the lowest triplet excitation energy level may be estimated from a peak wavelength of a phosphorescence spectrum of the organic compound.

<Materials>

Next, components of a light-emitting element of one embodiment of the present invention are described in detail below.

<<Light-Emitting Layer>>

In the light-emitting layer 113, the weight percentage of the host material 121 is higher than that of at least the guest material 122, and the guest material 122 (fluorescent material) is dispersed in the host material 121. Note that in the light-emitting layer 113, the host material 121 may be composed of one kind of compound or a plurality of compounds.

In the light-emitting layer 113, the guest material 122 is preferably, but not particularly limited to, an anthracene derivative, a tetracene derivative, a chrysene derivative, a phenanthrene derivative, a pyrene derivative, a perylene derivative, a stilbene derivative, an acridone derivative, a coumarin derivative, a phenoxazine derivative, a phenothiazine derivative, or the like, and for example, any of the following materials can be used.

The examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9-phenyl-9H-fluoren-9-yl)phenyl]-N,N'-bis(4-tert-butylphenyl)pyrene-1,6-diamine (abbreviation: 1,6tBu-FLPAPrn), N,N'-bis[4-(9-phenyl-9H-fluoren-9-yl)phenyl]-N,N'-diphenyl-3,8-dicyclohexylpyrene-1,6-diamine (abbreviation: ch-1,6FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis [N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 6, coumarin 545T, N,N'-diphenylquinacridone (abbreviation: DPQd), rubrene, 2,8-di-tert-butyl-5,11-bis(4-tert-butylphenyl)-6,12-diphenyltetracene (abbreviation: TBRb), Nile red, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis {2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl) ethenyl]-4H-pyran-4-ylidene}propanedinitrile (abbreviation: BisDCJ™), and 5,10,15,20-tetraphenylbisbenzo[5,6]indeno[1,2,3-cd:1',2',3'-lm]perylene.

Note that the light-emitting layer 113 may include a material other than the host material 121 and the guest material 122.

Although there is no particular limitation on a material that can be used in the light-emitting layer 113, any of the following materials can be used, for example: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato) beryllium(II) (abbreviation: BeBq$_2$), bis(2-methyl-8-quinolinolato) (4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)-tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spiro-9,9'-bifluoren-2-yl)-N-phenylamino]biphenyl (abbreviation: BSPB). In addition, condensed polycyclic aromatic compounds such as anthracene derivatives, phenanthrene derivatives, pyrene derivatives, chrysene derivatives, and dibenzo[g,p]chrysene derivatives can be used. Specific examples thereof include 9,10-diphenylanthracene (abbreviation: DPAnth), N,N'-diphenyl-9-[4-(10-phenyl-9-anthryl) phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N'',N'',N''',N'''-octaphenyldibenzo[g,p]chrysene-2,7,10,15-tetraamine (abbreviation: DBC1), 9-phenyl-3-[4-(10-phenyl-9-anthryl)phenyl]-9H-carbazol (abbreviation: PCzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl) anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), and 1,3,5-tri(1-pyrenyl)benzene (abbreviation: TPB3). One or more substances having a wider energy gap than the guest material 122 is preferably selected from these substances and known substances.

Note that the light-emitting layer 113 can have a structure in which two or more layers are stacked. For example, in the case where the light-emitting layer 113 is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material.

Next, details of other components of the light-emitting element 100 in FIG. 1A and the light-emitting element 120 in FIG. 2A are described below.

<<Hole-Injection Layer>>

The hole-injection layer 111 has a function of reducing a barrier for hole injection from one of the pair of electrodes (the electrode 101 or the electrode 102) to promote hole injection and is formed using, for example, a transition metal oxide, a phthalocyanine derivative, or an aromatic amine. Examples of the transition metal oxide include molybdenum oxide, vanadium oxide, ruthenium oxide, tungsten oxide, and manganese oxide. Examples of the phthalocyanine derivative include phthalocyanine and metal phthalocyanine. Examples of the aromatic amine include a benzidine derivative and a phenylenediamine derivative. It is also possible to use a high molecular compound such as polythiophene or polyaniline; a typical example thereof is poly (ethylenedioxythiophene)/poly(styrenesulfonic acid), which is self-doped polythiophene.

As the hole-injection layer 111, a layer containing a composite material of a hole-transport material and a material having a property of accepting electrons from the hole-transport material can also be used. Alternatively, a stack of a layer containing a material having an electron accepting property and a layer containing a hole-transport material may also be used. In a steady state or in the presence of an electric field, electric charge can be transferred between these materials. Examples of the material having an electron accepting property include organic compounds such as a quinodimethane derivative, a chloranil derivative, and a hexaazatriphenylene derivative. A specific example is a compound having an electron-withdrawing group (a halogen group or a cyano group), such as 7,7,8,8-tetracyano-2,3,5,6-tetrafluoroquinodimethane (abbreviation: $F_4$-TCNQ), chloranil, or 2,3,6,7,10,11-hexacyano-1,4,5,8,9,12-hexaazatriphenylene (abbreviation: HAT-CN). Alternatively, a transition metal oxide such as an oxide of a metal from Group 4 to Group 8 can also be used. Specifically, vanadium oxide, niobium oxide, tantalum oxide, chromium oxide, molybdenum oxide, tungsten oxide, manganese oxide, rhenium oxide, or the like can be used. In particular, molybdenum oxide is preferable because it is stable in the air, has a low hygroscopic property, and is easily handled.

A material having a property of transporting more holes than electrons can be used as the hole-transport material, and a material having a hole mobility of $1 \times 10^{-6}$ cm$^2$/Vs or higher is preferable. Specifically, an aromatic amine compound, a carbazole derivative, an aromatic hydrocarbon, a stilbene derivative, or the like can be used. Furthermore, the hole-transport material may be a high molecular compound.

Examples of the aromatic amine compound, which has a high hole-transport property, include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

Specific examples of the carbazole derivative are 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Other examples of the carbazole derivative are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene.

Examples of the aromatic hydrocarbon are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples are pentacene and coronene. The aromatic hydrocarbon having a hole mobility of $1 \times 10^{-6}$ cm$^2$/Vs or higher and having 14 to 42 carbon atoms is particularly preferable.

The aromatic hydrocarbon may have a vinyl skeleton. Examples of the aromatic hydrocarbon having a vinyl group are 4,4'-bis(2,2-diphenylvinyl)biphenyl (abbreviation: DPVBi) and 9,10-bis[4-(2,2-diphenylvinyl)phenyl]anthracene (abbreviation: DPVPA).

Other examples are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl)methacrylamide] (abbreviation: PTPDMA), and poly[N,N'-bis(4-butylphenyl)-N,N'-bis(phenyl)benzidine] (abbreviation: poly-TPD).

Examples of the material having a high hole-transport property are aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris[N-(1-naphthyl)-N-phenylamino]triphenylamine (abbreviation: 1'-TNATA), 4,4',4"-tris(N,N'-diphenylamino)triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N-phenyl-N-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N"-triphenyl-N,N',N"-tris(9-phenylcarbazol-3-yl)benzene-1,3,5-triamine (abbreviation: PCA3B), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation:

PCASF), 2,7-bis[N-(4-diphenylaminophenyl)-N-phenylamino]-spiro-9,9'-bifluorene (abbreviation: DPA2SF), N-[4-(9H-carbazol-9-yl)phenyl]-N-(4-phenyl)phenylaniline (abbreviation: YGA1BP), and N,N'-bis[4-(carbazol-9-yl)phenyl]-N,N'-diphenyl-9,9-dimethylfluorene-2,7-diamine (abbreviation: YGA2F). Other examples are amine compounds, carbazole compounds, thiophene compounds, furan compounds, fluorene compounds, triphenylene compounds, phenanthrene compounds, and the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 3,6-di(9H-carbazol-9-yl)-9-phenyl-9H-carbazole (abbreviation: PhCzGI), 2,8-di(9H-carbazol-9-yl)-dibenzothiophene (abbreviation: Cz2DBT), 4-{3-[3-(9-phenyl-9H-fluoren-9-yl)phenyl]phenyl}dibenzofuran (abbreviation: mmDBFFLBi-II), 4,4',4''-(benzene-1,3,5-triyl)tri(dibenzofuran) (abbreviation: DBF3P-II), 1,3,5-tri(dibenzothiophen-4-yl)-benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II). Among the above compounds, compounds including at least one of a pyrrole skeleton, a furan skeleton, a thiophene skeleton, and an aromatic amine skeleton are preferred because of their high stability and reliability. In addition, the compounds having such skeletons have a high hole-transport property to contribute to a reduction in driving voltage.

<<Hole-Transport Layer>>

The hole-transport layer 112 is a layer containing a hole-transport material and can be formed using any of the hole-transport materials given as examples of the material of the hole-injection layer 111. In order that the hole-transport layer 112 has a function of transporting holes injected into the hole-injection layer 111 to the light-emitting layer 113, the HOMO level of the hole-transport layer 112 is preferably equal or close to the HOMO level of the hole-injection layer 111.

As the hole-transport material, a substance having a hole mobility of $1\times10^{-6}$ cm$^2$/Vs or higher is preferably used. Note that any substance other than the above substances may be used as long as the hole-transport property is higher than the electron-transport property. The layer containing a substance having a high hole-transport property is not limited to a single layer, and two or more layers containing the aforementioned substances may be stacked.

In addition, the organic compound of one embodiment of the present invention can be suitably used.

<<Electron-Transport Layer>>

The electron-transport layer 114 has a function of transporting, to the light-emitting layer 113, electrons injected from the other of the pair of electrodes (the electrode 101 or the electrode 102) through the electron-injection layer 115. A material having a property of transporting more electrons than holes can be used as an electron-transport material, and a material having an electron mobility of $1\times10^{-6}$ cm$^2$/Vs or higher is preferable. As the compound which easily accepts electrons (the material having an electron-transport property), a n-electron deficient heteroaromatic compound such as a nitrogen-containing heteroaromatic compound, a metal complex, or the like can be used. Specific examples include a metal complex having a quinoline ligand, a benzoquinoline ligand, an oxazole ligand, or a thiazole ligand; an oxadiazole derivative; a triazole derivative; a benzimidazole derivative; a quinoxaline derivative; a dibenzoquinoxaline derivative; a phenanthroline derivative; a pyridine derivative; a bipyridine derivative; a pyrimidine derivative; and a triazine derivative. Note that a substance other than the above substances may be used as long as it has a higher electron-transport property than a hole-transport property. The electron-transport layer 114 is not limited to a single layer, and two or more layers containing the aforementioned substances may be stacked.

Specific examples include metal complexes having a quinoline or benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), and bis(8-quinolinolato)zinc(II) (abbreviation: Znq). Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ) can be used. Other than such metal complexes, any of the following can be used: heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-tert-butylphenyl)-1,2,4-triazole (abbreviation: TAZ), 9-[4-(4,5-diphenyl-4H-1,2,4-triazol-3-yl)phenyl]-9H-carbazole (abbreviation: CzTAZ1), 2,2',2''-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), bathophenanthroline (abbreviation: BPhen), 2,9-bis(naphthalen-2-yl)-4,7-diphenyl-1,10-phenanthroline (abbreviation: NBPhen), and bathocuproine (abbreviation: BCP); heterocyclic compounds having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 2-[3-(3,9'-bi-9H-carbazol-9-yl)phenyl]dibenzo[f,h]quinoxaline (abbreviation: 2mCzCzPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); heterocyclic compounds having a triazine skeleton such as 2-{4-[3-(N-phenyl-9H-carbazol-3-yl)-9H-carbazol-9-yl]phenyl}-4,6-diphenyl-1,3,5-triazine (abbreviation: PCCzPTzn); heterocyclic compounds having a pyridine skeleton such as 3,5-bis[3-(9H-carbazol-9-yl)phenyl]pyridine (abbreviation: 35DCzPPy) and 1,3,5-tri[3-(3-pyridyl)-phenyl]benzene (abbreviation: TmPyPB); and heteroaromatic compounds such as 4,4'-bis(5-methylbenzoxazol-2-yl)stilbene (abbreviation: BzOs). Among the heterocyclic compounds, the heterocyclic compounds having at least one of a triazine skeleton, a diazine skeleton (pyrimidine, pyrazine, pyridazine), and a pyridine skeleton are preferred because of their high reliability and stability. In addition, the heterocyclic compounds having the skeletons have a high electron-transport property to contribute to a reduction in driving voltage. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can be used. The substances described here are mainly substances having an electron mobility of $1\times10^{-6}$ cm$^2$/Vs or higher.

Note that a substance other than the above substances may be used as long as it has a higher electron-transport property than a hole-transport property. The electron-transport layer 114 is not limited to a single layer, and two or more layers containing the aforementioned substances may be stacked.

Between the electron-transport layer 114 and the light-emitting layer 113, a layer that controls transport of carriers may be provided. This is a layer formed by addition of a small amount of a substance having a high electron-trapping property to a material having a high electron-transport property as described above, and the layer is capable of adjusting carrier balance by suppressing transport of carriers. Such a structure is very effective in preventing a problem (such as a reduction in element lifetime) caused when electrons pass through the light-emitting layer.

An n-type compound semiconductor may also be used, and an oxide such as titanium oxide, zinc oxide, silicon oxide, tin oxide, tungsten oxide, tantalum oxide, barium titanate, barium zirconate, zirconium oxide, hafnium oxide, aluminum oxide, yttrium oxide, or zirconium silicate; a nitride such as silicon nitride; cadmium sulfide; zinc selenide; or zinc sulfide can be used, for example.

<<Electron-Injection Layer>>

The electron-injection layer 115 has a function of reducing a barrier for electron injection from the electrode 102 to promote electron injection and can be formed using a Group 1 metal or a Group 2 metal, or an oxide, a halide, or a carbonate of any of the metals, for example. Alternatively, a composite material containing an electron-transport material (described above) and a material having a property of donating electrons to the electron-transport material can also be used. Examples of the material having an electron-donating property include a Group 1 metal, a Group 2 metal, and an oxide of any of the metals. Specifically, an alkali metal, an alkaline earth metal, or a compound thereof, such as lithium fluoride, sodium fluoride, cesium fluoride, calcium fluoride, or lithium oxide, can be used. A rare earth metal compound such as erbium fluoride can also be used. An electride may also be used for the electron-injection layer 115. Examples of the electride include a substance in which electrons are added at high concentration to calcium oxide-aluminum oxide. The electron-injection layer 115 can be formed using the substance that can be used for the electron-transport layer 114.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material that is excellent in transporting the generated electrons. Specifically, the above-described substances for forming the electron-transport layer 114 (e.g., a metal complex and a heteroaromatic compound) can be used, for example. As the electron donor, a substance showing an electron-donating property with respect to the organic compound may be used. Specifically, an alkali metal, an alkaline earth metal, and a rare earth metal are preferable, and lithium, sodium, cesium, magnesium, calcium, erbium, ytterbium, or the like can be used. Furthermore, an alkali metal oxide or an alkaline earth metal oxide is preferable, and lithium oxide, calcium oxide, barium oxide, or the like can be used. A Lewis base such as magnesium oxide can also be used. An organic compound such as tetrathiafulvalene (abbreviation: TTF) can also be used.

Note that the light-emitting layer, the hole-injection layer, the hole-transport layer, the electron-transport layer, and the electron-injection layer described above can each be formed by an evaporation method (including a vacuum evaporation method), an inkjet method, a coating method, a gravure printing method, or the like. Besides the above-mentioned materials, an inorganic compound such as a quantum dot or a high molecular compound (e.g., an oligomer, a dendrimer, and a polymer) may be used in the light-emitting layer, the hole-injection layer, the hole-transport layer, the electron-transport layer, and the electron-injection layer.

<<Quantum Dot>>

A quantum dot is a semiconductor nanocrystal with a size of several nanometers to several tens of nanometers and contains approximately $1\times10^3$ to $1\times10^6$ atoms. Since energy shift of quantum dots depends on their size, quantum dots made of the same substance emit light with different wavelengths depending on their size. Thus, emission wavelengths can be easily adjusted by changing the size of quantum dots.

Since a quantum dot has an emission spectrum with a narrow peak, emission with high color purity can be obtained. In addition, a quantum dot is said to have a theoretical internal quantum efficiency of approximately 100%, which far exceeds that of a fluorescent organic compound, i.e., 25%, and is comparable to that of a phosphorescent organic compound. Therefore, a quantum dot can be used as a light-emitting material to obtain a light-emitting element having high light-emitting efficiency. Furthermore, since a quantum dot which is an inorganic material has high inherent stability, a light-emitting element which is favorable also in terms of lifetime can be obtained.

Examples of a material of a quantum dot include a Group 14 element, a Group 15 element, a Group 16 element, a compound of a plurality of Group 14 elements, a compound of an element belonging to any of Groups 4 to 14 and a Group 16 element, a compound of a Group 2 element and a Group 16 element, a compound of a Group 13 element and a Group 15 element, a compound of a Group 13 element and a Group 17 element, a compound of a Group 14 element and a Group 15 element, a compound of a Group 11 element and a Group 17 element, iron oxides, titanium oxides, spinel chalcogenides, and semiconductor clusters.

Specific examples include, but are not limited to, cadmium selenide; cadmium sulfide; cadmium telluride; zinc selenide; zinc oxide; zinc sulfide; zinc telluride; mercury sulfide; mercury selenide; mercury telluride; indium arsenide; indium phosphide; gallium arsenide; gallium phosphide; indium nitride; gallium nitride; indium antimonide; gallium antimonide; aluminum phosphide; aluminum arsenide; aluminum antimonide; lead selenide; lead telluride; lead sulfide; indium selenide; indium telluride; indium sulfide; gallium selenide; arsenic sulfide; arsenic selenide; arsenic telluride; antimony sulfide; antimony selenide; antimony telluride; bismuth sulfide; bismuth selenide; bismuth telluride; silicon; silicon carbide; germanium; tin; selenium; tellurium; boron; carbon; phosphorus; boron nitride; boron phosphide; boron arsenide; aluminum nitride; aluminum sulfide; barium sulfide; barium selenide; barium telluride;

calcium sulfide; calcium selenide; calcium telluride; beryllium sulfide; beryllium selenide; beryllium telluride; magnesium sulfide; magnesium selenide; germanium sulfide; germanium selenide; germanium telluride; tin sulfide; tin selenide; tin telluride; lead oxide; copper fluoride; copper chloride; copper bromide; copper iodide; copper oxide; copper selenide; nickel oxide; cobalt oxide; cobalt sulfide; triiron tetraoxide; iron sulfide; manganese oxide; molybdenum sulfide; vanadium oxide; tungsten oxide; tantalum oxide; titanium oxide; zirconium oxide; silicon nitride; germanium nitride; aluminum oxide; barium titanate; a compound of selenium, zinc, and cadmium; a compound of indium, arsenic, and phosphorus; a compound of cadmium, selenium, and sulfur; a compound of cadmium, selenium, and tellurium; a compound of indium, gallium, and arsenic; a compound of indium, gallium, and selenium; a compound of indium, selenium, and sulfur; a compound of copper, indium, and sulfur; and combinations thereof. What is called an alloyed quantum dot, whose composition is represented by a given ratio, may be used. For example, an alloyed quantum dot of cadmium, selenium, and sulfur is an effective material to obtain blue light because the emission wavelength can be changed by changing the content ratio of elements.

As the quantum dot, any of a core-type quantum dot, a core-shell quantum dot, a core-multishell quantum dot, and the like can be used. Note that when a core is covered with a shell formed of another inorganic material having a wider band gap, the influence of defects and dangling bonds existing at the surface of a nanocrystal can be reduced. Since such a structure can significantly improve the quantum efficiency of light emission, it is preferable to use a core-shell or core-multishell quantum dot. Examples of the material of a shell include zinc sulfide and zinc oxide.

Quantum dots have a high proportion of surface atoms and thus have high reactivity and easily cohere together. For this reason, it is preferable that a protective agent be attached to, or a protective group be provided at the surfaces of quantum dots. The attachment of the protective agent or the provision of the protective group can prevent cohesion and increase solubility in a solvent. It can also reduce reactivity and improve electrical stability. Examples of the protective agent (or the protective group) include polyoxyethylene alkyl ethers such as polyoxyethylene lauryl ether, polyoxyethylene stearyl ether, and polyoxyethylene oleyl ether; trialkylphosphines such as tripropylphosphine, tributylphosphine, trihexylphosphine, and trioctylphoshine; polyoxyethylene alkylphenyl ethers such as polyoxyethylene n-octylphenyl ether and polyoxyethylene n-nonylphenyl ether; tertiary amines such as tri(n-hexyl)amine, tri(n-octyl)amine, and tri(n-decyl)amine; organophosphorus compounds such as tripropylphosphine oxide, tributylphosphine oxide, trihexylphosphine oxide, trioctylphosphine oxide, and tridecylphosphine oxide; polyethylene glycol diesters such as polyethylene glycol dilaurate and polyethylene glycol distearate; organic nitrogen compounds such as nitrogen-containing aromatic compounds, e.g., pyridines, lutidines, collidines, and quinolines; aminoalkanes such as hexylamine, octylamine, decylamine, dodecylamine, tetradecylamine, hexadecylamine, and octadecylamine; dialkylsulfides such as dibutylsulfide; dialkylsulfoxides such as dimethylsulfoxide and dibutylsulfoxide; organic sulfur compounds such as sulfur-containing aromatic compounds, e.g., thiophene; higher fatty acids such as a palmitin acid, a stearic acid, and an oleic acid; alcohols; sorbitan fatty acid esters; fatty acid modified polyesters; tertiary amine modified polyurethanes; and polyethyleneimines.

Since band gaps of quantum dots are increased as their size is decreased, the size is adjusted as appropriate so that light with a desired wavelength can be obtained. Light emission from the quantum dots is shifted to a blue color side, i.e., a high energy side, as the crystal size is decreased; thus, emission wavelengths of the quantum dots can be adjusted over a wavelength region of a spectrum of an ultraviolet region, a visible light region, and an infrared region by changing the size of quantum dots. The range of size (diameter) of quantum dots which is usually used is greater than or equal to 0.5 nm and less than or equal to 20 nm, preferably greater than or equal to 1 nm and less than or equal to 10 nm. The emission spectra are narrowed as the size distribution of the quantum dots gets smaller, and thus light can be obtained with high color purity. The shape of the quantum dots is not particularly limited and may be a spherical shape, a rod shape, a circular shape, or the like. Quantum rods which are rod-like shape quantum dots have a function of emitting directional light; thus, quantum rods can be used as a light-emitting material to obtain a light-emitting element with higher external quantum efficiency.

In most organic EL elements, light-emitting materials are dispersed in host materials so that the concentration quenching of the light-emitting materials is suppressed to improve emission efficiency. The host materials need to be materials having singlet excitation energy levels or triplet excitation energy levels higher than or equal to those of the light-emitting materials. In the case of using blue phosphorescent materials as light-emitting materials, it is particularly difficult to develop host materials which have triplet excitation energy levels higher than or equal to those of the blue phosphorescent materials and which are excellent in terms of a lifetime. Even when a light-emitting layer is composed of quantum dots and made without a host material, the quantum dots enable emission efficiency to be ensured; thus, a light-emitting element which is favorable in terms of a lifetime can be obtained. In the case where the light-emitting layer is composed of quantum dots, the quantum dots preferably have core-shell structures (including core-multishell structures).

In the case of using quantum dots as the light-emitting material in the light-emitting layer, the thickness of the light-emitting layer is set to greater than or equal to 3 nm and less than or equal to 100 nm, preferably greater than or equal to 10 nm and less than or equal to 100 nm, and the light-emitting layer is made to contain greater than or equal to 1 volume % and less than or equal to 100 volume % of the quantum dots. Note that it is preferable that the light-emitting layer be composed of the quantum dots. To form a light-emitting layer in which the quantum dots are dispersed as light-emitting materials in host materials, the quantum dots may be dispersed in the host materials, or the host materials and the quantum dots may be dissolved or dispersed in an appropriate liquid medium, and then a wet process (e.g., a spin coating method, a casting method, a die coating method, a blade coating method, a roll coating method, an inkjet method, a printing method, a spray coating method, a curtain coating method, or a Langmuir-Blodgett method) may be employed. For a light-emitting layer containing a phosphorescent material, a vacuum evaporation method, as well as the wet process, can be suitably employed.

An example of the liquid medium used for the wet process is an organic solvent of ketones such as methyl ethyl ketone and cyclohexanone; fatty acid esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; dimethylformamide (DMF); dimethyl sulfoxide (DMSO); or the like.

<<Pair of Electrodes>>

The electrodes 101 and 102 function as an anode and a cathode of each light-emitting element. The electrodes 101 and 102 can be formed using a metal, an alloy, or a conductive compound, or a mixture or a stack thereof, for example.

One of the electrodes 101 and 102 is preferably formed using a conductive material having a function of reflecting light. Examples of the conductive material include aluminum (Al) and an alloy containing Al. Examples of the alloy containing Al include an alloy containing Al and L (L represents one or more of titanium (Ti), neodymium (Nd), nickel (Ni), and lanthanum (La)), such as an alloy containing Al and Ti and an alloy containing Al, Ni, and La. Aluminum has low resistance and high light reflectivity. Aluminum is included in earth's crust in large amount and is inexpensive; therefore, a light-emitting element with aluminum can be manufactured at low costs. Alternatively, silver (Ag), an alloy of Ag and N (N represents one or more of yttrium (Y), Nd, magnesium (Mg), ytterbium (Yb), Al, Ti, gallium (Ga), zinc (Zn), indium (In), tungsten (W), manganese (Mn), tin (Sn), iron (Fe), Ni, copper (Cu), palladium (Pd), iridium (Ir), and gold (Au)), or the like can be used. Examples of the alloy containing silver include an alloy containing silver, palladium, and copper, an alloy containing silver and copper, an alloy containing silver and magnesium, an alloy containing silver and nickel, an alloy containing silver and gold, and an alloy containing silver and ytterbium. Besides, a transition metal such as tungsten, chromium (Cr), molybdenum (Mo), copper, or titanium can be used.

Light emitted from the light-emitting layer is extracted through the electrode 101 and/or the electrode 102. Thus, at least one of the electrodes 101 and 102 is preferably formed using a conductive material having a function of transmitting light. Examples of the conductive material include a conductive material having a visible light transmittance higher than or equal to 40% and lower than or equal to 100%, preferably higher than or equal to 60% and lower than or equal to 100%, and a resistivity lower than or equal to $1\times10^{-2}$ Ω·cm.

The electrodes 101 and 102 may each be formed using a conductive material having functions of transmitting light and reflecting light. Examples of the conductive material include a conductive material having a visible light reflectivity higher than or equal to 20% and lower than or equal to 80%, preferably higher than or equal to 40% and lower than or equal to 70%, and a resistivity lower than or equal to $1\times10^{-2}$ Ω·cm. For example, one or more kinds of conductive metals and alloys, conductive compounds, and the like can be used. Specifically, a metal oxide such as indium tin oxide (hereinafter, referred to as ITO), indium tin oxide containing silicon or silicon oxide (ITSO), indium oxide-zinc oxide (indium zinc oxide), indium oxide-tin oxide containing titanium, indium titanium oxide, or indium oxide containing tungsten oxide and zinc oxide can be used. A metal thin film having a thickness that allows transmission of light (preferably, a thickness greater than or equal to 1 nm and less than or equal to 30 nm) can also be used. As the metal, Ag, an alloy of Ag and Al, an alloy of Ag and Mg, an alloy of Ag and Au, an alloy of Ag and Yb, or the like can be used.

In this specification and the like, the material transmitting light may be a material that transmits visible light and has conductivity. Examples of the material include, in addition to the above-described oxide conductor typified by ITO, an oxide semiconductor and an organic conductor containing an organic substance. Examples of the organic conductor containing an organic substance include a composite material in which an organic compound and an electron donor (donor) are mixed and a composite material in which an organic compound and an electron acceptor (acceptor material) are mixed. Alternatively, an inorganic carbon-based material such as graphene may be used. The resistivity of the material is preferably lower than or equal to $1\times10^5$ Ω·cm, further preferably lower than or equal to $1\times10^4$ Ω·cm.

Alternatively, the electrode 101 and/or the electrode 102 may be formed by stacking two or more of these materials.

In order to improve the light extraction efficiency, a material whose refractive index is higher than that of an electrode having a function of transmitting light may be formed in contact with the electrode. Such a material may be a conductive material or a non-conductive material as long as having a function of transmitting visible light. In addition to the above-described oxide conductor, an oxide semiconductor and an organic material are given as examples. Examples of the organic material include the materials for the light-emitting layer, the hole-injection layer, the hole-transport layer, the electron-transport layer, and the electron-injection layer. Alternatively, an inorganic carbon-based material or a metal film thin enough to transmit light can be used. Further alternatively, stacked layers with a thickness of several nanometers to several tens of nanometers may be used.

In the case where the electrode 101 or the electrode 102 functions as the cathode, the electrode preferably contains a material having a low work function (lower than or equal to 3.8 eV). The examples include an element belonging to Group 1 or 2 of the periodic table (e.g., an alkali metal such as lithium, sodium, or cesium, an alkaline earth metal such as calcium or strontium, or magnesium), an alloy containing any of these elements (e.g., Ag—Mg or Al—Li), a rare earth metal such as europium (Eu) or Yb, an alloy containing any of these rare earth metals, and an alloy containing aluminum and silver.

In the case where the electrode 101 or the electrode 102 is used as an anode, a material having a high work function (4.0 eV or higher) is preferably used.

Alternatively, the electrodes 101 and 102 may each be a stacked layer of a conductive material having a function of reflecting light and a conductive material having a function of transmitting light. In that case, the electrodes 101 and 102 can each have a function of adjusting the optical path length so that desired light emitted from each light-emitting layer resonates and is intensified; thus, such a structure is preferable.

As the method for forming the electrodes 101 and 102, a sputtering method, an evaporation method, a printing method, a coating method, a molecular beam epitaxy (MBE) method, a CVD method, a pulsed laser deposition method, an atomic layer deposition (ALD) method, or the like can be used as appropriate.

<<Substrate>>

A light-emitting element of one embodiment of the present invention may be formed over a substrate of glass, plastic, or the like. As the way of stacking layers over the substrate, layers may be sequentially stacked from the electrode 101 side or sequentially stacked from the electrode 102 side.

For the substrate over which the light-emitting element of one embodiment of the present invention can be formed, glass, quartz, plastic, or the like can be used. Alternatively, a flexible substrate can be used. The flexible substrate means a substrate that can be bent, such as a plastic substrate made of polycarbonate or polyarylate, for example. Alternatively, a film, an inorganic vapor deposition film, or the like can be used. Another material may be used as long as the substrate functions as a support in a manufacturing process of the light-emitting element or the optical element. Another material having a function of protecting the light-emitting element or the optical element may be used.

In this specification and the like, a light-emitting element can be formed using any of a variety of substrates, for example. The type of substrate is not limited to a certain type. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film. Examples of a glass substrate include a barium borosilicate glass substrate, an aluminoborosilicate glass substrate, and a soda lime glass substrate. Examples of the flexible substrate, the attachment film, the base material film, and the like are substrates of plastics typified by polyethylene terephthalate (PET), polyethylene naphthalate (PEN), polyether sulfone (PES), and polytetrafluoroethylene (PTFE). Another example is a resin such as acrylic. Alternatively, polypropylene, polyester, polyvinyl fluoride, polyvinyl chloride, or the like can be used. Further alternatively, polyamide, polyimide, aramid, epoxy, an inorganic vapor deposition film, paper, or the like can be used.

Alternatively, a flexible substrate may be used as the substrate, and the light-emitting element may be provided directly on the flexible substrate. Further alternatively, a separation layer may be provided between the substrate and the light-emitting element. The separation layer can be used when part or the whole of the light-emitting element formed over the separation layer is separated from the substrate and transferred to another substrate. In such a case, the light-emitting element can be transferred to a substrate having low heat resistance or a flexible substrate as well. Note that the above separation layer may have a structure in which inorganic films of a tungsten film and a silicon oxide film are stacked, a structure in which a resin film of polyimide or the like is formed over a substrate, or the like.

In other words, after the light-emitting element is formed using a substrate, the light-emitting element may be transferred to another substrate. Examples of a substrate to which the light-emitting element is transferred include, in addition to the above-described substrates, a cellophane substrate, a stone substrate, a wood substrate, a cloth substrate (including a natural fiber (e.g., silk, cotton, and hemp), a synthetic fiber (e.g., nylon, polyurethane, and polyester), a regenerated fiber (e.g., acetate, cupra, rayon, and regenerated polyester), and the like), a leather substrate, and a rubber substrate. When such a substrate is used, a light-emitting element with high durability, high heat resistance, reduced weight, or reduced thickness can be formed.

The light-emitting element 110 may be formed over an electrode electrically connected to a field-effect transistor (FET), for example, which is formed over any of the above-described substrates. Accordingly, an active matrix display device in which the FET controls the driving of the light-emitting element 110 can be manufactured.

In this embodiment, one embodiment of the present invention has been described. Other embodiments of the present invention are described in the other embodiments. Note that one embodiment of the present invention is not limited to the above examples. In other words, various embodiments of the invention are described in this embodiment and the other embodiments, and one embodiment of the present invention is not limited to a particular embodiment. An example in which one embodiment of the present invention is used in a light-emitting element is described; however, one embodiment of the present invention is not limited thereto. For example, depending on circumstances or conditions, one embodiment of the present invention is not necessarily used in a light-emitting element.

The structure described above in this embodiment can be combined with any of the other embodiments as appropriate.

Embodiment 4

In this embodiment, one embodiment of a light-emitting element having a structure in which a plurality of light-emitting units are stacked (hereinafter, also referred to as stacked-type element) is described with reference to FIG. 3. This light-emitting element includes a plurality of light-emitting units between a first electrode and a second electrode. Each light-emitting unit can have the same structure as the EL layer 103 which is described in Embodiment 3. In other words, the light-emitting element described in Embodiment 3 includes one light-emitting unit while the light-emitting element described in this embodiment includes a plurality of light-emitting units.

Structure Example 1 of Light-Emitting Device

Figure 3:
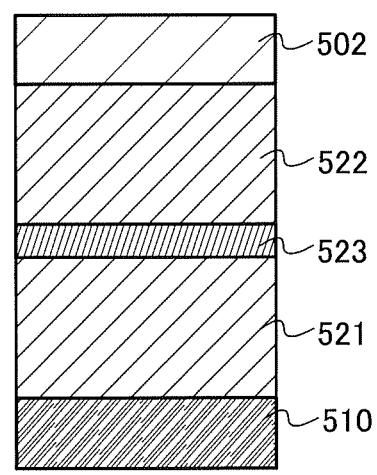
FIG. 3 is a schematic view of a light-emitting element of one embodiment of the present invention.

In FIG. 3, a first light-emitting unit 521 and a second light-emitting unit 522 are stacked between a first electrode 510 and a second electrode 502, and a charge-generation layer 523 is provided between the first light-emitting unit 521 and the second light-emitting unit 522. The first electrode 510 and the second electrode 502 respectively correspond to the electrode 101 and the electrode 102 in Embodiment 3, and materials described in Embodiment 3 can be used. Furthermore, the first light-emitting unit 521 and the second light-emitting unit 522 may have the same structure or different structures. For example, it is preferable that the EL layer 103 described in Embodiment 3 be used in the first light-emitting unit 521.

The charge-generation layer 523 may have either a structure in which an acceptor substance that is an electron acceptor is added to a hole-transport material or a structure in which a donor substance that is an electron donor is added to an electron-transport material. Alternatively, both of these structures may be stacked.

In the case where the charge-generation layer 523 contains a composite material of an organic compound and an acceptor substance, the composite material that can be used for the hole-injection layer 111 described in Embodiment 3 can be used for the composite material. As the organic compound, a variety of compounds such as an aromatic amine compound, a carbazole compound, an aromatic hydrocarbon, and a high molecular compound (such as an oligomer, a dendrimer, or a polymer) can be used. A substance having a hole mobility of $1 \times 10^{-6}$ cm$^2$/Vs or higher is preferably used as the organic compound. Note that any other substance may be used as long as it has a property of transporting more holes than electrons. Since the composite material of an organic compound and an acceptor substance has excellent carrier-injection and carrier-transport properties, low-voltage driving or low-current driving can be achieved. Note that when a surface of a light-emitting unit on the anode side is in contact with the charge-generation layer 523, the charge-generation layer 523 can also serve as a hole-injection layer or a hole-transport layer of the light-emitting unit; thus, a hole-injection layer or a hole-transport layer is not necessarily included in the light-emitting unit. When a surface of a light-emitting unit on the cathode side is in contact with the charge-generation layer 523, the charge-generation layer 523 can also serve as an electron-injection layer or an electron-transport layer of the light-emitting unit; thus, an electron-injection layer or an electron-transport layer is not necessarily included in the light-emitting unit.

The charge-generation layer 523 may have a stacked-layer structure of a layer containing the composite material of an organic compound and an acceptor substance and a layer containing another material. For example, the charge-generation layer 523 may be formed using a combination of a layer containing the composite material of an organic compound and an acceptor substance with a layer containing one compound selected from among electron-donating materials and a compound having a high electron-transport property. Furthermore, the charge-generation layer 523 may be formed using a combination of a layer containing the composite material of an organic compound and an acceptor substance with a layer containing a transparent conductive film.

The charge-generation layer 523 provided between the first light-emitting unit 521 and the second light-emitting unit 522 may have any structure as long as electrons can be injected into the light-emitting unit on one side and holes can be injected into the light-emitting unit on the other side when a voltage is applied between the first electrode 510 and the second electrode 502. For example, in FIG. 3, the charge-generation layer 523 injects electrons into the first light-emitting unit 521 and holes into the second light-emitting unit 522 when a voltage is applied such that the potential of the first electrode 510 is higher than that of the second electrode 502.

Note that in terms of light extraction efficiency, the charge-generation layer 523 preferably has a visible light transmittance (specifically, a visible light transmittance of higher than or equal to 40%). The charge-generation layer 523 functions even when it has lower conductivity than the pair of electrodes (the electrodes 510 and 502).

The charge-generation layer 523 formed by using any of the above materials can suppress an increase in driving voltage caused by the stack of the light-emitting layers.

The charge-generation layer 523 may have a stacked-layer structure of a layer containing a composite material of an organic compound and a metal oxide and a layer containing another material. For example, a layer containing the composite material of an organic compound and a metal oxide may be combined with a layer containing a compound of a substance selected from electron-donating substances and a compound having a high electron-transport property. Moreover, the charge-generation layer 523 may be formed using a combination of a layer containing the composite material of an organic compound and a metal oxide with a transparent conductive film.

The charge-generation layer 523 provided between the first light-emitting unit 521 and the second light-emitting unit 522 may have any structure as long as electrons can be injected into the light-emitting unit on one side and holes can be injected into the light-emitting unit on the other side when a voltage is applied between the first electrode 510 and the second electrode 502. For example, in FIG. 3, the charge-generation layer 523 injects electrons into the first light-emitting unit 521 and holes into the second light-emitting unit 522 when a voltage is applied such that the potential of the first electrode 510 is higher than that of the second electrode 502.

Although the light-emitting element having two light-emitting units is described in this embodiment, the present invention can be similarly applied to a light-emitting element in which three or more light-emitting units are stacked. With a plurality of light-emitting units partitioned by the charge-generation layer between a pair of electrodes, as in the light-emitting element of this embodiment, light with high luminance can be obtained while current density is kept low; thus, a light-emitting element having a long lifetime can be obtained. Moreover, a light-emitting device that can be driven at a low voltage and has low power consumption can be achieved.

When light-emitting units have different emission colors, light emission of desired color can be obtained as a whole light-emitting element. For example, by forming a light-emitting element having two light-emitting units such that the emission color of the first light-emitting unit and the emission color of the second light-emitting unit are complementary colors, the light-emitting element can provide white light emission as a whole. Note that the word "complementary" means color relationship in which an achromatic color is obtained when colors are mixed. In other words, when light components obtained from substances that emit light of complementary colors are mixed, white light emission can be obtained. Furthermore, the same can be applied to a light-emitting element having three light-emitting units. For example, the light-emitting element as a whole can provide white light emission when the emission color of the first light-emitting unit is red, the emission color of the second light-emitting unit is green, and the emission color of the third light-emitting unit is blue. Alternatively, in the case of employing a light-emitting element in which a phosphorescent emission center substance is used for a light-emitting layer of one light-emitting unit and a fluorescent emission center substance is used for a light-emitting layer of the other light-emitting unit, both fluorescence and phosphorescence can be efficiently emitted from the light-emitting element. For example, when red phosphorescence and green phosphorescence are obtained from one light-emitting unit and blue fluorescence is obtained from the other light-emitting unit, white light with high emission efficiency can be obtained.

When the organic compound of one embodiment of the present invention is used in a light-emitting element, a blue fluorescent element with low driving voltage, high efficiency, and long lifetime can be provided. Thus, lower driving voltage, higher efficiency, longer lifetime, and color adjustment of the light-emitting element as a whole can be easily achieved.

This embodiment can be combined with any of the other embodiments as appropriate.

Embodiment 5

In this embodiment, a light-emitting device including the light-emitting element described in Embodiment 3 and Embodiment 4 is described with reference to FIGS. 4A and 4B.

FIG. 4A is a top view of the light-emitting device and FIG. 4B is a cross-sectional view taken along the lines A-B and C-D in FIG. 4A. The light-emitting device includes a driver circuit portion (source side driver circuit) 601, a pixel portion 602, and a driver circuit portion (gate side driver circuit) 603, which control light emission of a light-emitting element and are illustrated with dotted lines. Moreover, a reference numeral 604 denotes a sealing substrate, a reference numeral 625 denotes a desiccant, and a reference numeral 605 denotes a sealant. A portion surrounded by the sealant 605 is a space 607.

Note that a lead wiring 608 is a wiring for transmitting signals to be input to the source side driver circuit 601 and the gate side driver circuit 603 and for receiving a video signal, a clock signal, a start signal, a reset signal, and the like from a flexible printed circuit (FPC) 609 functioning as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, a cross-sectional structure of the light-emitting device is described with reference to FIG. 4B. The driver circuit portion and the pixel portion are formed over an element substrate 610. Here, the source side driver circuit 601, which is the driver circuit portion, and one pixel of the pixel portion 602 are illustrated.

In the source side driver circuit 601, a CMOS circuit is formed in which an n-channel TFT 623 and a p-channel TFT 624 are combined. The driver circuit may be formed using various circuits such as a CMOS circuit, a PMOS circuit, or an NMOS circuit. Although a driver-integrated type in which the driver circuit is formed over the substrate is described in this embodiment, the driver circuit is not necessarily formed over the substrate, and may be formed outside the substrate.

The pixel portion 602 includes a plurality of pixels including a switching TFT 611, a current controlling TFT 612, and a first electrode 613 electrically connected to a drain of the current controlling TFT 612. Note that an insulator 614 is formed to cover an end portion of the first electrode 613. The insulator 614 can be formed using a positive photosensitive resin film.

In order to improve coverage with a film that is formed over the insulator 614, the insulator 614 is formed to have a curved surface with curvature at its upper or lower end portion. For example, in the case where photosensitive acrylic is used as a material of the insulator 614, only the upper end portion of the insulator 614 preferably has a curved surface. The radius of curvature of the curved surface is preferably greater than or equal to 0.2 μm and less than or equal to 0.3 μm. As the insulator 614, either a negative photosensitive material or a positive photosensitive material can be used.

An EL layer 616 and a second electrode 617 are formed over the first electrode 613. As a material used for the first electrode 613 which functions as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack including a titanium nitride film and a film containing aluminum as its main component, a stack including three layers of a titanium nitride film, a film containing aluminum as its main component, and a titanium nitride film, or the like can be used. The stacked structure achieves low wiring resistance, a favorable ohmic contact, and a function as an anode.

The EL layer 616 is formed by any of a variety of methods such as an evaporation method using an evaporation mask, an inkjet method, and a spin coating method. As another material included in the EL layer 616, a low molecular compound or a high molecular compound (including an oligomer or a dendrimer) may be used.

As a material used for the second electrode 617, which is formed over the EL layer 616 and functions as a cathode, a material having a low work function (e.g., Al, Mg, Li, Ca, or an alloy or a compound thereof, such as MgAg, MgIn, or AlLi) is preferably used. In the case where light generated in the EL layer 616 passes through the second electrode 617, a stack including a thin metal film and a transparent conductive film (e.g., ITO, indium oxide containing zinc oxide at 2 wt % or higher and 20 wt % or lower, indium tin oxide containing silicon, or zinc oxide (ZnO)) is preferably used for the second electrode 617.

Note that a light-emitting element 618 is formed with the first electrode 613, the EL layer 616, and the second electrode 617. The light-emitting element 618 preferably has the structure described in Embodiment 3 and Embodiment 4. In the light-emitting device of this embodiment, the pixel portion, which includes a plurality of light-emitting elements, may include both the light-emitting element with the structure described in Embodiment 3 and Embodiment 4 and a light-emitting element with a different structure.

The sealing substrate 604 is attached to the element substrate 610 with the sealant 605, so that the light-emitting element 618 is provided in the space 607 surrounded by the element substrate 610, the sealing substrate 604, and the sealant 605. The space 607 is filled with a filler. The filler may be an inert gas (such as nitrogen or argon), or a resin and/or a desiccant.

An epoxy-based resin or glass frit is preferably used for the sealant 605. It is preferable that such a material do not transmit moisture or oxygen as much as possible. As the sealing substrate 604, a glass substrate, a quartz substrate, or a plastic substrate formed of fiber reinforced plastic (FRP), polyvinyl fluoride (PVF), polyester, acrylic, or the like can be used.

As described above, the light-emitting device including the light-emitting element described in Embodiment 3 and Embodiment 4 can be obtained.

Structure Example 2 of Light-Emitting Device

FIGS. 5A and 5B each illustrate an example of a light-emitting device including a light-emitting element exhibiting white light emission and a coloring layer (a color filter).

FIG. 5A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1026, an EL layer 1028, a second electrode 1029 of the light-emitting elements, a sealing substrate 1031, a sealant 1032, and the like.

In FIGS. 5A and 5B, coloring layers (a red coloring layer 1034R, a green coloring layer 1034G, and a blue coloring layer 1034B) are provided on a transparent base material 1033. A black layer (a black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 5A, light emitted from some of the light-emitting layers does not pass through the coloring layers, while light emitted from the others of the light-emitting layers passes through the coloring layers. Since light that does not pass through the coloring layers is white and light that passes through any one of the coloring layers is red, blue, or green, an image can be displayed using pixels of the four colors.

FIG. 5B illustrates an example in which the red coloring layer 1034R, the green coloring layer 1034G, and the blue coloring layer 1034B are formed between the gate insulating film 1003 and the first interlayer insulating film 1020. As illustrated in FIG. 5B, the coloring layers may be provided between the substrate 1001 and the sealing substrate 1031.

The above-described light-emitting device has a structure in which light is extracted from the substrate 1001 side where the TFTs are formed (a bottom emission structure), but may have a structure in which light is extracted from the sealing substrate 1031 side (a top emission structure).

Structure Example 3 of Light-Emitting Device

Figure 6:
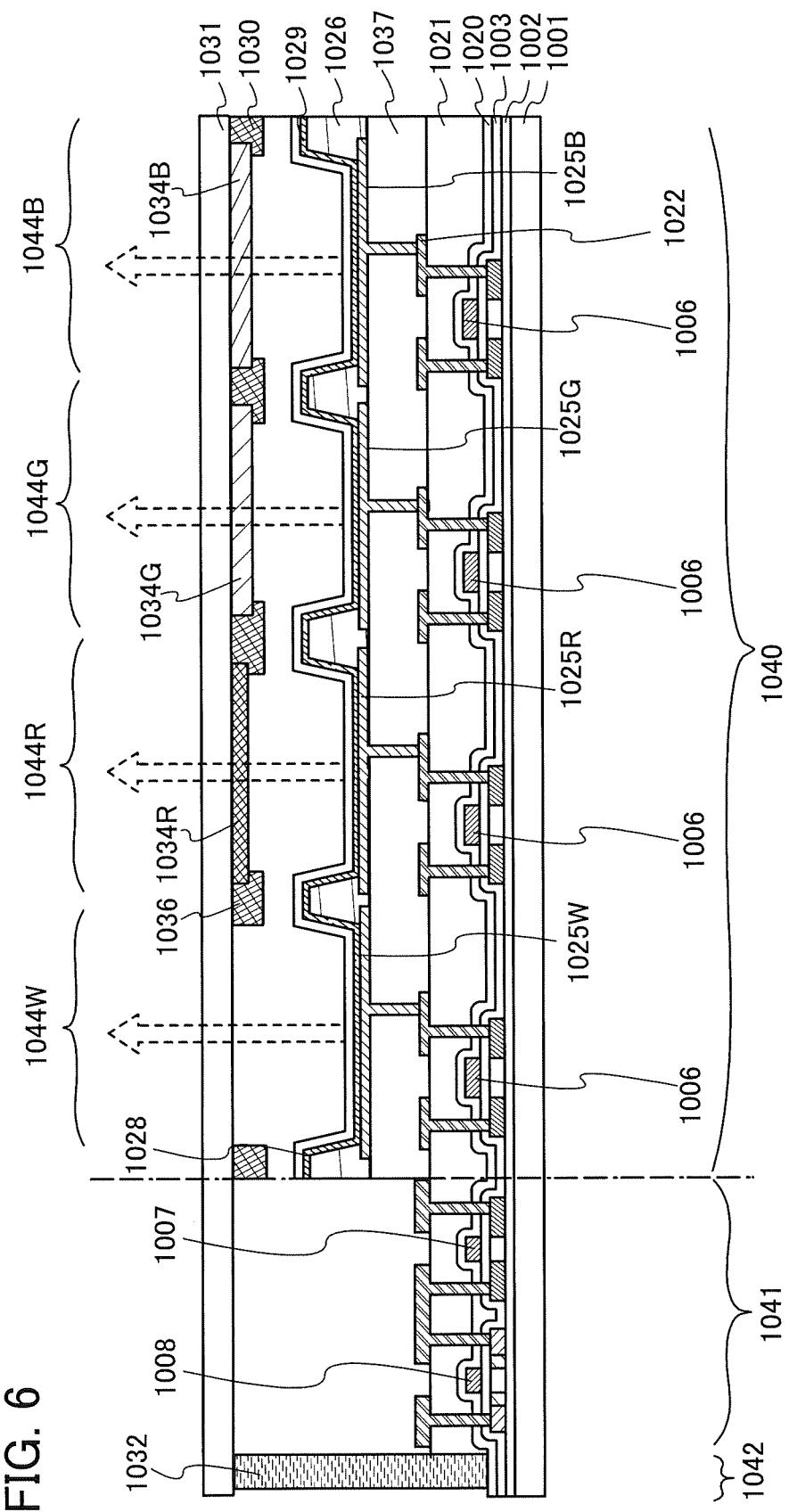
FIG. 6 is a conceptual diagram of an active matrix light-emitting device of one embodiment of the present invention.

FIG. 6 is a cross-sectional view of a light-emitting device having a top emission structure. In this case, a substrate that does not transmit light can be used as the substrate 1001. The process up to the step of forming of a connection electrode which connects the TFT and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film 1021, or can be formed using any other various materials.

Lower electrodes 1025W, 1025R, 1025G, and 1025B of the light-emitting elements each function as an anode here, but may function as a cathode. Furthermore, in the case of the light-emitting device having a top emission structure as illustrated in FIG. 6, the lower electrodes 1025W, 1025R, 1025G, and 1025B are preferably reflective electrodes. Note that the second electrode 1029 preferably has a function of reflecting light and a function of transmitting light. It is preferable that a microcavity structure be used between the second electrode 1029 and the lower electrodes 1025W, 1025R, 1025G, and 1025B, in which case light having a specific wavelength is amplified. The EL layer 1028 is formed to have a structure similar to the structure described in Embodiment 2 and Embodiment 3, with which white light emission can be obtained.

In FIGS. 5A and 5B and FIG. 6, the structure of the EL layer for providing white light emission can be achieved by, for example, using a plurality of light-emitting layers or using a plurality of light-emitting units. Note that the structure to provide white light emission is not limited to the above.

In the case of a top emission structure as illustrated in FIG. 6, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (the black matrix) 1035 which is positioned between pixels. The coloring layers (the red coloring layer 1034R, the green coloring layer 1034G, and the blue coloring layer 1034B) and the black layer (the black matrix) may be covered with the overcoat layer. Note that a light-transmitting substrate is used as the sealing substrate 1031.

Although an example in which full color display is performed using four colors of red, green, blue, and white is shown here, there is no particular limitation and full color display using three colors of red, green, and blue or four colors of red, green, blue, and yellow may be performed.

As described above, the light-emitting device including the light-emitting element described in Embodiment 3 and Embodiment 4 can be obtained.

This embodiment can be combined with any of the other embodiments as appropriate.

Embodiment 6

In this embodiment, a specific example of a display device including the light-emitting element described in Embodiment 3 and Embodiment 4 is described. A display device described below includes both a reflective liquid crystal element and a light-emitting element. The display device can perform display in a transmissive mode and in a reflective mode. The light-emitting element described in Embodiment 3 and Embodiment 4 is preferably used.

[Structure Example of Display Device 1]

FIG. 7A is a block diagram illustrating an example of the structure of a display device 400. The display device 400 includes a plurality of pixels 410 that are arranged in a matrix in a display portion 362. The display device 400 also includes a circuit GD and a circuit SD. In addition, the display device 400 includes a plurality of wirings G1, a plurality of wirings G2, a plurality of wirings ANO, and a plurality of wirings CSCOM, which are electrically connected to the circuit GD and the plurality of pixels 410 arranged in a direction R. Moreover, the display device 400 includes a plurality of wirings S1 and a plurality of wirings S2 which are electrically connected to the circuit SD and the plurality of pixels 410 arranged in a direction C.

The pixel 410 includes a reflective liquid crystal element and a light-emitting element. In the pixel 410, the liquid crystal element and the light-emitting element partly overlap with each other.

FIG. 7B1 illustrates a structure example of an electrode 311b included in the pixel 410. The electrode 311b serves as a reflective electrode of the liquid crystal element in the pixel 410. The electrode 311b has an opening 451.

In FIG. 7B1, a light-emitting element 360 in a region overlapping with the electrode 311b is denoted by a dashed line. The light-emitting element 360 overlaps with the opening 451 included in the electrode 311b. Thus, light from the light-emitting element 360 is emitted to the display surface side through the opening 451.

In FIG. 7B1, the pixels 410 adjacent in the direction R correspond to different emission colors. As illustrated in FIG. 7B1, the openings 451 are preferably provided in different positions in the electrodes 311b so as not to be aligned in the two pixels adjacent to each other in the direction R. This allows the two light-emitting elements 360 to be apart from each other, thereby preventing light emitted from the light-emitting element 360 from entering a coloring layer in the adjacent pixel 410 (such a phenomenon is also referred to as crosstalk). Furthermore, since the two adjacent light-emitting elements 360 can be arranged apart from each other, a high-resolution display device is achieved even when EL layers of the light-emitting elements 360 are separately formed with a shadow mask or the like.

Alternatively, arrangement illustrated in FIG. 7B2 may be employed.

If the ratio of the total area of the opening 451 to the total area except for the opening is too large, display performed using the liquid crystal element is dark. If the ratio of the total area of the opening 451 to the total area except for the opening is too small, display performed using the light-emitting element 360 is dark.

If the area of the opening 451 in the electrode 311*b* serving as a reflective electrode is too small, light emitted from the light-emitting element 360 is not efficiently extracted.

The opening 451 may have a polygonal shape, a quadrangular shape, an elliptical shape, a circular shape, a cross-like shape, a stripe shape, a slit-like shape, or a checkered pattern, for example. The opening 451 may be close to the adjacent pixel. Preferably, the opening 451 is provided close to another pixel emitting light of the same color, in which case crosstalk can be suppressed.

[Circuit Configuration Example]

Figure 8:
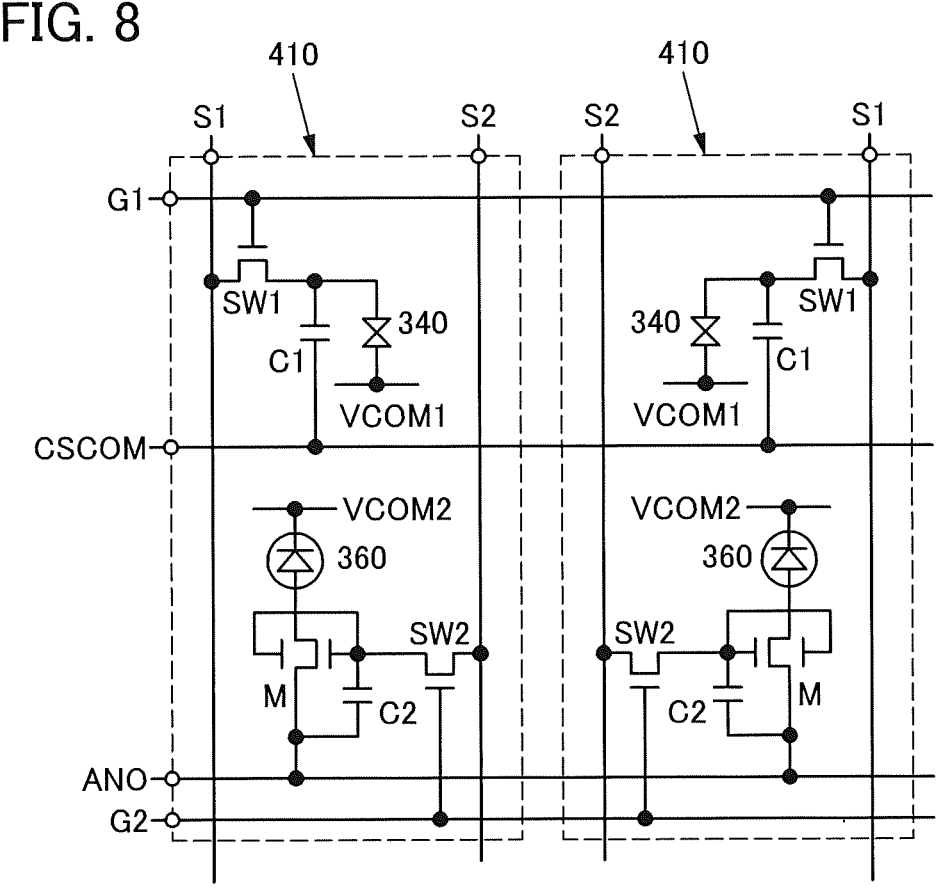
FIG. 8 is a circuit diagram of a display device of one embodiment of the present invention.

FIG. 8 is a circuit diagram illustrating a configuration example of the pixel 410. FIG. 8 illustrates two adjacent pixels 410.

The pixel 410 includes a switch SW1, a capacitor C1, a liquid crystal element 340, a switch SW2, a transistor M, a capacitor C2, the light-emitting element 360, and the like. The pixel 410 is electrically connected to the wiring G1, the wiring G2, the wiring ANO, the wiring CSCOM, the wiring S1, and the wiring S2. FIG. 8 also illustrates a wiring VCOM1 electrically connected to the liquid crystal element 340 and a wiring VCOM2 electrically connected to the light-emitting element 360.

FIG. 8 illustrates an example in which a transistor is used as each of the switches SW1 and SW2.

A gate of the switch SW1 is connected to the wiring G1. One of a source and a drain of the switch SW1 is connected to the wiring S1, and the other of the source and the drain is connected to one electrode of the capacitor C1 and one electrode of the liquid crystal element 340. The other electrode of the capacitor C1 is connected to the wiring CSCOM. The other electrode of the liquid crystal element 340 is connected to the wiring VCOM1.

A gate of the switch SW2 is connected to the wiring G2. One of a source and a drain of the switch SW2 is connected to the wiring S2, and the other of the source and the drain is connected to one electrode of the capacitor C2 and a gate of the transistor M. The other electrode of the capacitor C2 is connected to one of a source and a drain of the transistor M and the wiring ANO. The other of the source and the drain of the transistor M is connected to one electrode of the light-emitting element 360. The other electrode of the light-emitting element 360 is connected to the wiring VCOM2.

FIG. 8 illustrates an example in which the transistor M includes two gates between which a semiconductor is provided and which are connected to each other. This structure can increase the amount of current flowing through the transistor M.

The wiring G1 can be supplied with a signal for changing the on/off state of the switch SW1. A predetermined potential can be supplied to the wiring VCOM1. The wiring S1 can be supplied with a signal for changing the orientation of liquid crystals of the liquid crystal element 340. A predetermined potential can be supplied to the wiring CSCOM.

The wiring G2 can be supplied with a signal for changing the on/off state of the switch SW2. The wiring VCOM2 and the wiring ANO can be supplied with potentials having a difference large enough to make the light-emitting element 360 emit light. The wiring S2 can be supplied with a signal for changing the conduction state of the transistor M.

In the pixel 410 of FIG. 8, for example, an image can be displayed in the reflective mode by driving the pixel with the signals supplied to the wiring G1 and the wiring S1 and utilizing the optical modulation of the liquid crystal element 340. In the case where an image is displayed in the transmissive mode, the pixel is driven with the signals supplied to the wiring G2 and the wiring S2 and the light-emitting element 360 emits light. In the case where both modes are performed at the same time, the pixel can be driven with the signals supplied to the wiring G1, the wiring G2, the wiring S1, and the wiring S2.

Figure 9A:
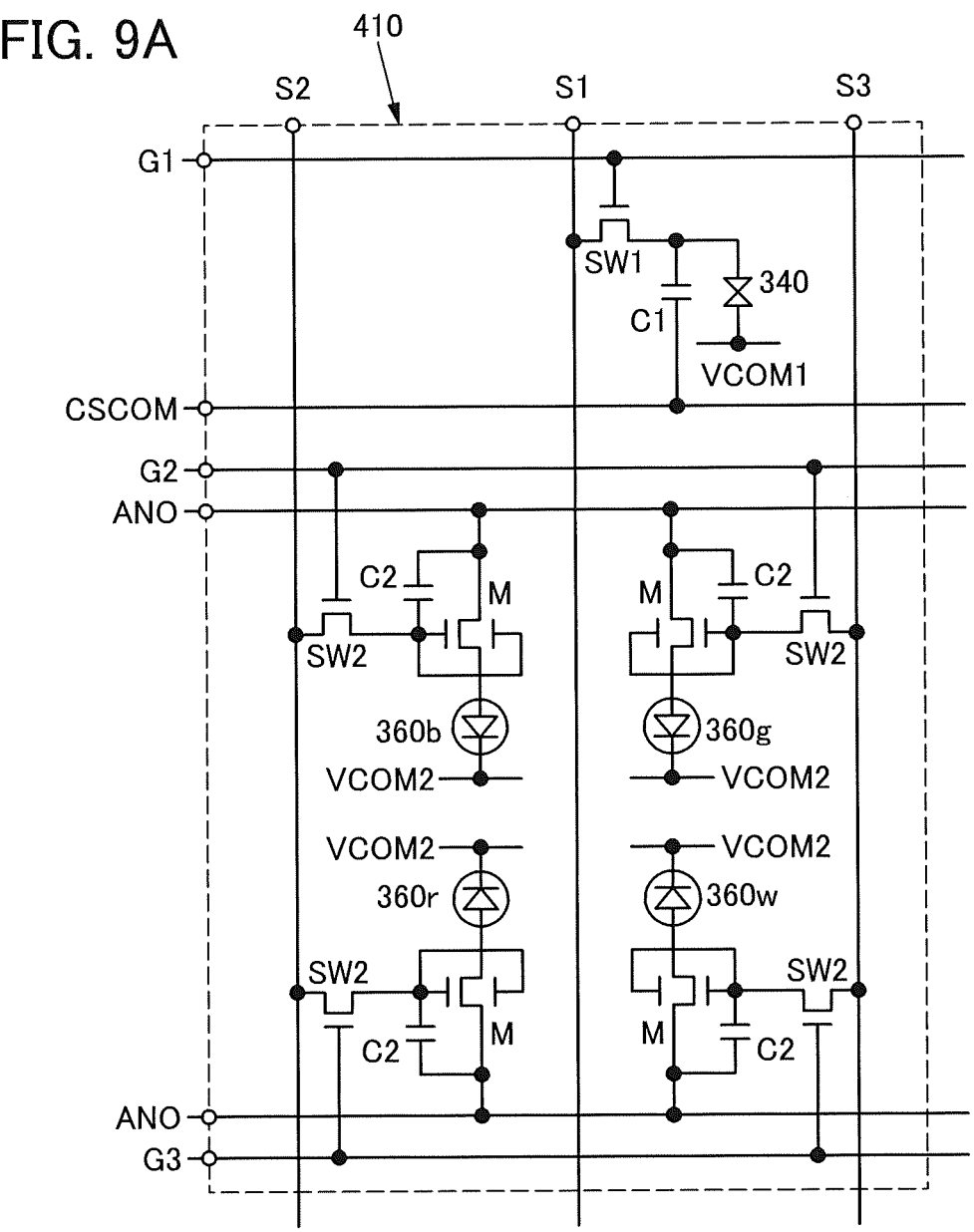
FIGS. 9A and 9B are a circuit diagram and a schematic diagram of a pixel in a display device of one embodiment of the present invention.

Although FIG. 8 illustrates an example in which one liquid crystal element 340 and one light-emitting element 360 are provided in one pixel 410, one embodiment of the present invention is not limited to this example. FIG. 9A illustrates an example in which one liquid crystal element 340 and four light-emitting elements 360 (light-emitting elements 360*r*, 360*g*, 360*b*, and 360*w*) are provided in one pixel 410. The pixel 410 illustrated in FIG. 9A differs from that in FIG. 8 in being capable of performing full-color display by one pixel.

In addition to the example in FIG. 8, the pixel 410 in FIG. 9A is connected to a wiring G3 and a wiring S3.

In the example illustrated in FIG. 9A, for example, light-emitting elements which exhibit red (R), green (G), blue (B), and white (W) can be used as the four light-emitting elements 360. Furthermore, as the liquid crystal element 340, a reflective liquid crystal element emitting white light can be used. Thus, in the case of performing display in the reflective mode, white display with high reflectivity can be performed. In the case of performing display in the transmissive mode, an image can be displayed with a higher color rendering property at low power consumption.

Figure 9B:
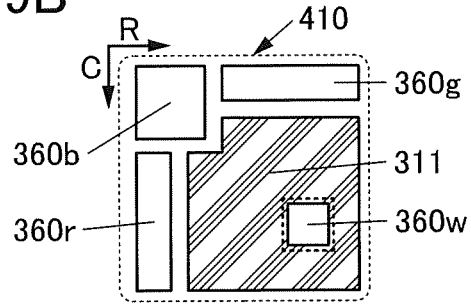

FIG. 9B illustrates a configuration example of the pixel 410. The pixel 410 includes the light-emitting element 360*w* which overlaps with the opening in the electrode 311 and the light-emitting elements 360*r*, 360*g*, and 360*b* which are located near the electrode 311. It is preferable that the light-emitting elements 360*r*, 360*g*, and 360*b* have substantially the same light-emitting area.

[Structure Example of Display Device 2]

FIG. 10 is a schematic perspective view of a display device 300 of one embodiment of the present invention. In the display device 300, a substrate 351 and a substrate 361 are bonded to each other. In FIG. 10, the substrate 361 is denoted by a dashed line.

The display device 300 includes the display portion 362, a circuit portion 364, a wiring 365, a circuit portion 366, a wiring 367, and the like. The substrate 351 is provided with the circuit portion 364, the wiring 365, the circuit portion 366, the wiring 367, the electrode 311*b* functioning as a pixel electrode, and the like. In FIG. 10, an IC 373, an FPC 372, an IC 375, and an FPC 374 are mounted on the substrate 351. Thus, the structure illustrated in FIG. 10 can be referred to as a display module including the display device 300, the IC 373, the FPC 372, the IC 375, and the FPC 374.

For the circuit portion 364, a circuit functioning as a scan line driver circuit can be used, for example.

The wiring 365 has a function of supplying a signal and electric power to the display portion and the circuit portion 364. The signal and electric power are input to the wiring 365 from the outside through the FPC 372 or from the IC 373.

FIG. 10 illustrates an example in which the IC 373 is provided on the substrate 351 by a chip on glass (COG) method or the like. As the IC 373, an IC functioning as a scan line driver circuit, a signal line driver circuit, or the like can be used. Note that it is possible that the IC 373 is not provided, for example, when the display device 300 includes circuits functioning as a scan line driver circuit and a signal line driver circuit and when the circuits functioning as a scan line driver circuit and a signal line driver circuit are provided outside and signals for driving the display device 300 are input through the FPC 372. Alternatively, the IC 373 may be mounted on the FPC 372 by a chip on film (COF) method or the like.

FIG. 10 illustrates an enlarged view of a part of the display portion 362. Electrodes 311b included in a plurality of display elements are arranged in a matrix in the display portion 362. The electrode 311b has a function of reflecting visible light and serves as a reflective electrode of the liquid crystal element 340 described later.

As illustrated in FIG. 10, the electrode 311b has an opening. The light-emitting element 360 is positioned closer to the substrate 351 than the electrode 311b is. Light is emitted from the light-emitting element 360 to the substrate 361 side through the opening in the electrode 311b.

Figure 11:
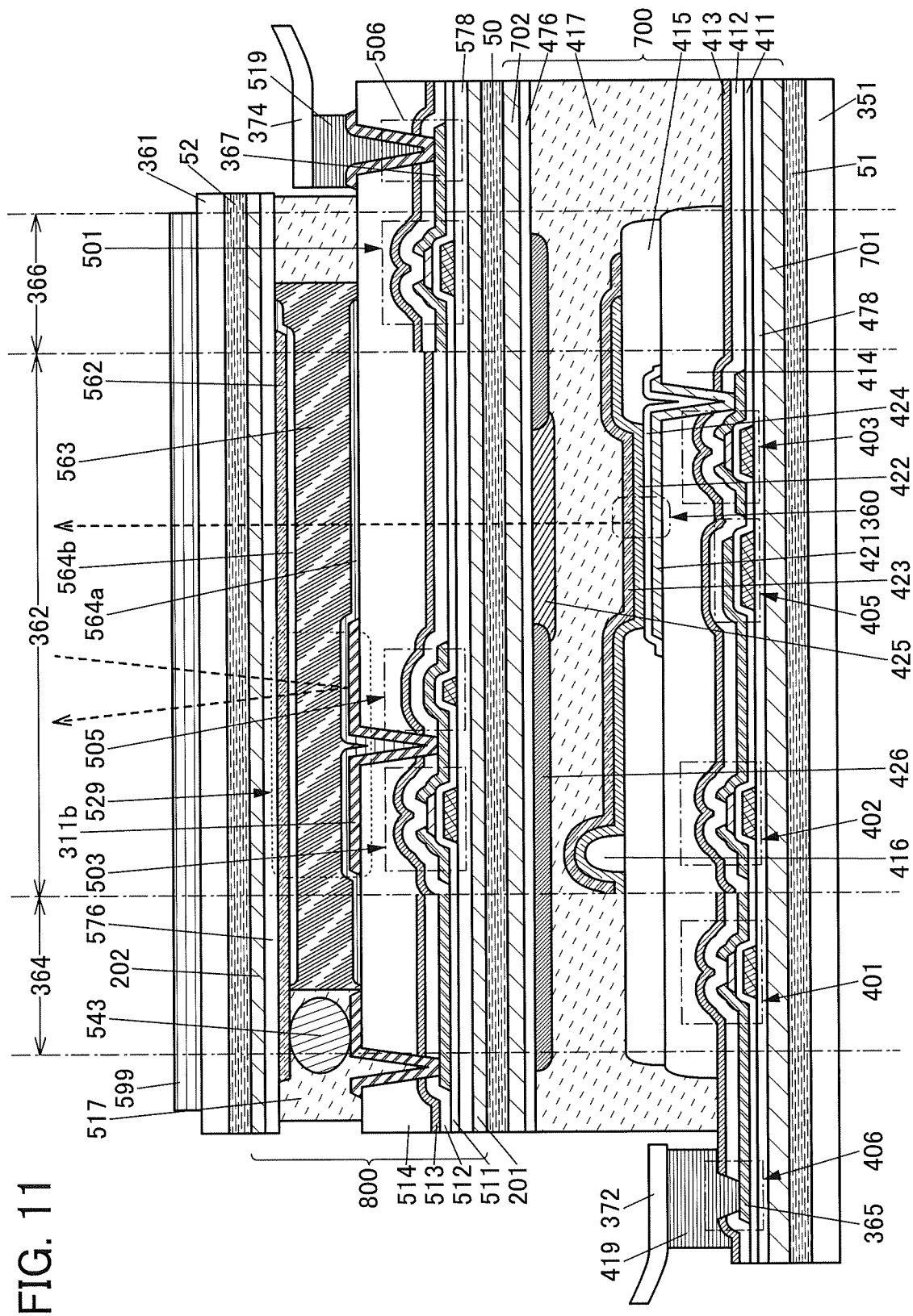
FIG. 11 is a schematic view of a display device of one embodiment of the present invention.

FIG. 11 illustrates an example of cross sections of part of a region including the FPC 372, part of a region including the circuit portion 364, part of a region including the display portion 362, part of a region including the circuit portion 366, and part of a region including the FPC 374 of the display device illustrated in FIG. 10.

The display device illustrated in FIG. 11 has a structure in which a display panel 700 and a display panel 800 are stacked. The display panel 700 includes a resin layer 701 and a resin layer 702. The display panel 800 includes a resin layer 201 and a resin layer 202. The resin layers 702 and 201 are bonded to each other with an adhesive layer 50. The resin layer 701 is bonded to the substrate 351 with an adhesive layer 51. The resin layer 202 is bonded to the substrate 361 with an adhesive layer 52.

[Display Panel 700]

The display panel 700 includes the resin layer 701, an insulating layer 478, a plurality of transistors, a capacitor 405, an insulating layer 411, an insulating layer 412, an insulating layer 413, an insulating layer 414, an insulating layer 415, the light-emitting element 360, a spacer 416, an adhesive layer 417, a coloring layer 425, a light-blocking layer 426, an insulating layer 476, and the resin layer 702.

The circuit portion 364 includes a transistor 401. The display portion 362 includes a transistor 402 and a transistor 403.

Each of the transistors includes a gate, the insulating layer 411, a semiconductor layer, a source, and a drain. The gate and the semiconductor layer overlap with each other with the insulating layer 411 provided therebetween. Part of the insulating layer 411 functions as a gate insulating layer, and another part of the insulating layer 411 functions as a dielectric of the capacitor 405. A conductive layer that functions as the source or the drain of the transistor 402 also functions as one electrode of the capacitor 405.

The transistors illustrated in FIG. 11 have bottom-gate structures. The transistor structures may be different between the circuit portion 364 and the display portion 362. The circuit portion 364 and the display portion 362 may each include a plurality of kinds of transistors.

The capacitor 405 includes a pair of electrodes and the dielectric therebetween. The capacitor 405 includes a conductive layer that is formed using the same material and the same process as the gates of the transistors, and a conductive layer that is formed using the same material and the same process as the sources and the drains of the transistors.

The insulating layer 412, the insulating layer 413, and the insulating layer 414 are each provided to cover the transistors and the like. The number of the insulating layers covering the transistors and the like is not particularly limited. The insulating layer 414 functions as a planarization layer. It is preferable that at least one of the insulating layer 412, the insulating layer 413, and the insulating layer 414 be formed using a material inhibiting diffusion of impurities such as water and hydrogen. Diffusion of impurities from the outside into the transistors can be effectively inhibited, leading to improved reliability of the display device.

In the case of using an organic compound for the insulating layer 414, impurities such as moisture might enter the light-emitting element 360 or the like from the outside of the display device through the insulating layer 414 exposed at an end portion of the display device. Deterioration of the light-emitting element 360 due to the entry of impurities can lead to deterioration of the display device. For this reason, the insulating layer 414 is preferably not positioned at the end portion of the display device, as illustrated in FIG. 11. Since an insulating layer formed using an organic compound is not positioned at the end portion of the display device in the structure of FIG. 11, entry of impurities into the light-emitting element 360 can be inhibited.

The light-emitting element 360 includes an electrode 421, an EL layer 422, and an electrode 423. The light-emitting element 360 may include an optical adjustment layer 424. The light-emitting element 360 has a top emission structure with which light is emitted to the coloring layer 425 side.

The transistors, the capacitor, the wiring, and the like are positioned so as to overlap with a light-emitting region of the light-emitting element 360; accordingly, the aperture ratio of the display portion 362 can be increased.

One of the electrode 421 and the electrode 423 functions as an anode and the other functions as a cathode. When a voltage higher than the threshold voltage of the light-emitting element 360 is applied between the electrode 421 and the electrode 423, holes are injected to the EL layer 422 from the anode side and electrons are injected to the EL layer 422 from the cathode side. The injected electrons and holes are recombined in the EL layer 422 and a light-emitting substance contained in the EL layer 422 emits light.

The electrode 421 is electrically connected to the source or the drain of the transistor 403 directly or through a conductive layer. The electrode 421 functioning as a pixel electrode is provided for each light-emitting element 360. Two adjacent electrodes 421 are electrically insulated from each other by the insulating layer 415.

The electrode 423 functioning as a common electrode is shared by a plurality of light-emitting elements 360. A fixed potential is supplied to the electrode 423.

The light-emitting element 360 overlaps with the coloring layer 425 with the adhesive layer 417 provided therebetween. The spacer 416 overlaps with the light-blocking layer 426 with the adhesive layer 417 provided therebetween. Although FIG. 11 illustrates the case where a space is provided between the electrode 423 and the light-blocking layer 426, the electrode 423 and the light-blocking layer 426 may be in contact with each other. Although the spacer 416 is provided on the substrate 351 side in the structure illustrated in FIG. 11, the spacer 416 may be provided on the substrate 361 side (e.g., in a position closer to the substrate 361 than that of the light-blocking layer 426).

Owing to the combination of a color filter (the coloring layer 425) and a microcavity structure (the optical adjustment layer 424), light with high color purity can be extracted from the display device. The thickness of the optical adjustment layer 424 is varied depending on the color of the pixel.

The coloring layer 425 is a coloring layer that transmits light in a specific wavelength range. For example, a color filter for transmitting light in a red, green, blue, or yellow wavelength range can be used.

Note that one embodiment of the present invention is not limited to a color filter method, and a separate coloring method, a color conversion method, a quantum dot method, and the like may be employed.

The light-blocking layer 426 is provided between the adjacent coloring layers 425. The light-blocking layer 426 blocks light emitted from the adjacent light-emitting element 360 to inhibit color mixture between the adjacent light-emitting elements 360. Here, the coloring layer 425 is provided such that its end portion overlaps with the light-blocking layer 426, whereby light leakage can be reduced. For the light-blocking layer 426, a material that blocks light emitted from the light-emitting element 360 can be used. Note that it is preferable to provide the light-blocking layer 426 in a region other than the display portion 362, such as the circuit portion 364, in which case undesired leakage of guided light or the like can be inhibited.

The insulating layer 478 is formed on a surface of the resin layer 701. The insulating layer 476 is formed on a surface of the resin layer 702. The insulating layer 476 and the insulating layer 478 are preferably highly resistant to moisture. The light-emitting element 360, the transistors, and the like are preferably provided between a pair of insulating layers with high resistance to moisture, in which case impurities such as water can be prevented from entering these elements, leading to an increase in the reliability of the display device.

Examples of the insulating film highly resistant to moisture include a film containing nitrogen and silicon (e.g., a silicon nitride film and a silicon nitride oxide film) and a film containing nitrogen and aluminum (e.g., an aluminum nitride film). Alternatively, a silicon oxide film, a silicon oxynitride film, an aluminum oxide film, or the like may be used.

For example, the moisture vapor transmittance of the insulating film with high resistance to moisture is lower than or equal to $1 \times 10^{-5}$ [g/(m²·day)], preferably lower than or equal to $1 \times 10^{-6}$ [g/(m²·day)], further preferably lower than or equal to $1 \times 10^{-7}$ [g/(m²·day)], and still further preferably lower than or equal to $1 \times 10^{-8}$ [g/(m²·day)].

A connection portion 406 includes the wiring 365. The wiring 365 can be formed using the same material and the same process as those of the sources and the drains of the transistors. The connection portion 406 is electrically connected to an external input terminal through which a signal and a potential from the outside are transmitted to the circuit portion 364. Here, an example in which the FPC 372 is provided as the external input terminal is described. The FPC 372 is electrically connected to the connection portion 406 through a connection layer 419.

The connection layer 419 can be formed using any of various kinds of anisotropic conductive films (ACF), anisotropic conductive pastes (ACP), and the like.

The above is the description of the display panel 700.

[Display Panel 800]

The display panel 800 is a reflective liquid crystal display device employing a vertical electric field mode.

The display panel 800 includes the resin layer 201, an insulating layer 578, a plurality of transistors, a capacitor 505, the wiring 367, an insulating layer 511, an insulating layer 512, an insulating layer 513, an insulating layer 514, a liquid crystal element 529, an alignment film 564a, an alignment film 564b, an adhesive layer 517, an insulating layer 576, and the resin layer 202.

The resin layers 201 and 202 are bonded to each other with the adhesive layer 517. Liquid crystal 563 is sealed in a region surrounded by the resin layer 201, the resin layer 202, and the adhesive layer 517. A polarizing plate 599 is positioned on an outer surface of the substrate 361.

The liquid crystal element 529 includes the electrode 311b, an electrode 562, and the liquid crystal 563. The electrode 311b functions as a pixel electrode. The electrode 562 functions as a common electrode. Alignment of the liquid crystal 563 can be controlled with an electric field generated between the electrode 311b and the electrode 562. The alignment film 564a is provided between the liquid crystal 563 and the electrode 311b. The alignment film 564b is provided between the liquid crystal 563 and the electrode 562.

The resin layer 202 is provided with the insulating layer 576, the electrode 562, the alignment film 564b, and the like.

The resin layer 201 is provided with the electrode 311b, the alignment film 564a, a transistor 501, a transistor 503, the capacitor 505, a connection portion 506, the wiring 367, and the like.

Insulating layers such as the insulating layer 511, the insulating layer 512, the insulating layer 513, and the insulating layer 514 are provided over the resin layer 201.

Note that a portion of the conductive layer functioning as the source or the drain of the transistor 503 which is not electrically connected to the electrode 311b may function as part of a signal line. The conductive layer functioning as a gate of the transistor 503 may function as part of a scan line.

FIG. 11 illustrates a structure without a coloring layer as an example of the display portion 362. Thus, the liquid crystal element 529 is an element that performs monochrome display.

FIG. 11 illustrates an example of the circuit portion 366 in which the transistor 501 is provided.

A material inhibiting diffusion of impurities such as water and hydrogen is preferably used for at least one of the insulating layers 512 and 513 which cover the transistors.

The electrode 311b is provided over the insulating layer 514. The electrode 311b is electrically connected to one of the source and the drain of the transistor 503 through an opening formed in the insulating layer 514, the insulating layer 513, the insulating layer 512, and the like. The electrode 311b is electrically connected to one electrode of the capacitor 505.

Since the display panel 800 is a reflective liquid crystal display device, a conductive material that reflects visible light is used for the electrode 311b and a conductive material that transmits visible light is used for the electrode 562.

For example, a material containing one of indium (In), zinc (Zn), and tin (Sn) is preferably used for the conductive material that transmits visible light. Specific examples include indium oxide, indium tin oxide (ITO), indium zinc oxide, indium oxide containing tungsten oxide, indium zinc oxide containing tungsten oxide, indium oxide containing titanium oxide, indium tin oxide containing titanium oxide, indium tin oxide containing silicon oxide (ITSO), zinc oxide, and zinc oxide containing gallium. Note that a film containing graphene can be used as well. The film containing graphene can be formed, for example, by reducing a film containing graphene oxide.

Examples of the conductive material that reflects visible light include aluminum, silver, and an alloy containing any of these metal materials. A metal material such as gold, platinum, nickel, tungsten, chromium, molybdenum, iron, cobalt, copper, or palladium, or an alloy containing any of these metal materials can also be used. Furthermore, lanthanum, neodymium, germanium, or the like may be added to the metal material or the alloy. Furthermore, an alloy containing aluminum (an aluminum alloy) such as an alloy of aluminum and titanium, an alloy of aluminum and nickel, an alloy of aluminum and neodymium, or an alloy of aluminum, nickel, and lanthanum (Al—Ni—La); or an alloy containing silver such as an alloy of silver and copper, an alloy of silver, palladium, and copper (also referred to as Ag—Pd—Cu or APC), or an alloy of silver and magnesium may be used.

As the polarizing plate 599, a linear polarizing plate or a circularly polarizing plate can be used. An example of a circularly polarizing plate is a stack including a linear polarizing plate and a quarter-wave retardation plate. Such a structure can reduce reflection of external light. The cell gap, alignment, driving voltage, and the like of the liquid crystal element used as the liquid crystal element 529 are controlled depending on the kind of the polarizing plate 599 so that desirable contrast is obtained.

The electrode 562 is electrically connected to a conductive layer on the resin layer 201 side through a connector 543 in a portion close to an end portion of the resin layer 202. Thus, a potential or a signal can be supplied from the FPC 374, an IC, or the like placed on the resin layer 201 side to the electrode 562.

As the connector 543, a conductive particle can be used, for example. As the conductive particle, a particle of an organic resin, silica, or the like coated with a metal material can be used. It is preferable to use nickel or gold as the metal material because contact resistance can be decreased. It is also preferable to use a particle coated with layers of two or more kinds of metal materials, such as a particle coated with nickel and further with gold. As the connector 543, a material capable of elastic deformation or plastic deformation is preferably used. As illustrated in FIG. 11, the connector 543, which is the conductive particle, has a shape that is vertically crushed in some cases. With the crushed shape, the contact area between the connector 543 and a conductive layer electrically connected to the connector 543 can be increased, thereby reducing contact resistance and suppressing the generation of problems such as disconnection.

The connector 543 is preferably provided so as to be covered with the adhesive layer 517. For example, the connectors 543 are dispersed in the adhesive layer 517 before curing of the adhesive layer 517.

The connection portion 506 is provided in a region near an end portion of the resin layer 201. The connection portion 506 is electrically connected to the FPC 374 through a connection layer 519. In the example of the structure illustrated in FIG. 11, the connection portion 506 is formed by stacking part of the wiring 367 and a conductive layer that is obtained by processing the same conductive film as the electrode 311b.

The above is the description of the display panel 800.

[Display Element]

As a display element included in a first pixel located on the display surface side, an element which performs display by reflecting external light can be used. Such an element does not include a light source and thus power consumption in display can be significantly reduced. As the display element included in the first pixel, a reflective liquid crystal element can be typically used. Alternatively, as the display element included in the first pixel, an element using a microcapsule method, an electrophoretic method, an electrowetting method, an Electronic Liquid Powder (registered trademark) method, or the like can be used, other than a micro electro mechanical systems (MEMS) shutter element or an optical interference type MEMS element.

As a display element included in a second pixel located on the side opposite to the display surface side, an element which includes a light source and performs display using light from the light source can be used. Since the luminance and the chromaticity of light emitted from such a pixel are not affected by external light, an image with high color reproducibility (a wide color gamut) and a high contrast, i.e., a clear image can be displayed. As the display element included in the second pixel, a self-luminous light-emitting element such as an organic light-emitting diode (OLED), a light-emitting diode (LED), or a quantum-dot light-emitting diode (QLED) can be used. Alternatively, a combination of a backlight that is a light source and a transmissive liquid crystal element that controls the amount of transmitted light emitted from a backlight may be used as the display element included in the second pixel.

[Liquid Crystal Element]

The liquid crystal element can employ, for example, a vertical alignment (VA) mode. Examples of the vertical alignment mode include a multi-domain vertical alignment (MVA) mode, a patterned vertical alignment (PVA) mode, and an advanced super view (ASV) mode.

The liquid crystal element can employ a variety of modes. For example, a liquid crystal element using, instead of a VA mode, a twisted nematic (TN) mode, an in-plane switching (IPS) mode, a fringe field switching (FFS) mode, an axially symmetric aligned micro-cell (ASM) mode, an optically compensated birefringence (OCB) mode, a ferroelectric liquid crystal (FLC) mode, an antiferroelectric liquid crystal (AFLC) mode, or the like can be used.

The liquid crystal element controls transmission or non-transmission of light utilizing an optical modulation action of a liquid crystal. The optical modulation action of the liquid crystal is controlled by an electric field applied to the liquid crystal (including a horizontal electric field, a vertical electric field, and an oblique electric field). As the liquid crystal used for the liquid crystal element, thermotropic liquid crystal, low-molecular liquid crystal, high-molecular liquid crystal, polymer dispersed liquid crystal (PDLC), ferroelectric liquid crystal, anti-ferroelectric liquid crystal, or the like can be used. These liquid crystal materials exhibit a cholesteric phase, a smectic phase, a cubic phase, a chiral nematic phase, an isotropic phase, or the like depending on conditions.

As the liquid crystal material, either a positive liquid crystal or a negative liquid crystal may be used, and an appropriate liquid crystal material can be used depending on the mode or design to be used.

An alignment film can be provided to adjust the alignment of a liquid crystal. In the case where a horizontal electric field mode is employed, a liquid crystal exhibiting a blue phase for which an alignment film is unnecessary may be used. The blue phase is one of liquid crystal phases, which is generated just before a cholesteric phase changes into an isotropic phase while temperature of a cholesteric liquid crystal is increased. Since the blue phase appears only in a narrow temperature range, a liquid crystal composition in which a chiral material is mixed to account for several weight percent or more is used for the liquid crystal layer in order to improve the temperature range. The liquid crystal composition that includes a liquid crystal exhibiting a blue phase and a chiral material has a short response time and has optical isotropy. In addition, the liquid crystal composition that includes a liquid crystal exhibiting a blue phase and a chiral material does not need alignment treatment and has small viewing angle dependence. An alignment film does not need to be provided and rubbing treatment is thus not necessary; accordingly, electrostatic discharge damage caused by the rubbing treatment can be prevented and defects and damage of the liquid crystal display device in the manufacturing process can be reduced.

In the case where a reflective liquid crystal element is used, a polarizing plate is provided on the display surface side. In addition, a light diffusion plate is preferably provided on the display surface side to improve visibility.

[Light-Emitting Element]

As the light-emitting element, a self-luminous element can be used, and an element whose luminance is controlled by current or voltage is included in the category of the light-emitting element. For example, an LED, a QLED, an organic EL element, or an inorganic EL element can be used; however, any of the light-emitting elements described in Embodiment 3 and Embodiment 4 is preferably used.

In this embodiment, in particular, the light-emitting element preferably has a top emission structure. A conductive film that transmits visible light is used as the electrode through which light is extracted. A conductive film that reflects visible light is preferably used as the electrode through which light is not extracted. The light-emitting element may be a single element including one EL layer or a tandem element in which a plurality of EL layers are stacked with a charge-generation layer positioned therebetween.

The EL layer includes at least a light-emitting layer. In addition to the light-emitting layer, the EL layer may further include one or more layers containing any of a substance with a high hole-injection property, a substance with a high hole-transport property, a hole-blocking material, a substance with a high electron-transport property, a substance with a high electron-injection property, a substance with a bipolar property (a substance with a high electron- and hole-transport property), and the like.

For the EL layer, the low-molecular compound, the high-molecular compound, or the inorganic compound described in Embodiment 3 can be used. Each of the layers included in the EL layer can be formed by any of the following methods: an evaporation method (including a vacuum evaporation method), a transfer method, a printing method, an inkjet method, a coating method, and the like.

[Adhesive Layer]

As the adhesive layer, a variety of curable adhesives such as a reactive curable adhesive, a thermosetting adhesive, an anaerobic adhesive, and a photocurable adhesive such as an ultraviolet curable adhesive can be used. Examples of these adhesives include an epoxy resin, an acrylic resin, a silicone resin, a phenol resin, a polyimide resin, an imide resin, a polyvinyl chloride (PVC) resin, a polyvinyl butyral (PVB) resin, and an ethylene vinyl acetate (EVA) resin. In particular, a material with low moisture permeability, such as an epoxy resin, is preferred. Alternatively, a two-component type resin may be used. Further alternatively, an adhesive sheet or the like may be used.

Furthermore, the resin may include a drying agent. For example, a substance that adsorbs moisture by chemical adsorption, such as oxide of an alkaline earth metal (e.g., calcium oxide or barium oxide), can be used. Alternatively, a substance that adsorbs moisture by physical adsorption, such as zeolite or silica gel, may be used. The drying agent is preferably included because it can prevent impurities such as moisture from entering the element, thereby improving the reliability of the display panel.

In addition, it is preferable to mix a filler with a high refractive index or light-scattering member into the resin, in which case light extraction efficiency can be enhanced. For example, titanium oxide, barium oxide, zeolite, or zirconium can be used.

[Connection Layer]

As the connection layer, an anisotropic conductive film (ACF), an anisotropic conductive paste (ACP), or the like can be used.

[Coloring Layer]

Examples of a material that can be used for the coloring layer include a metal material, a resin material, and a resin material containing a pigment or dye.

[Light-Blocking Layer]

Examples of a material that can be used for the light-blocking layer include carbon black, titanium black, a metal, a metal oxide, and a composite oxide containing a solid solution of a plurality of metal oxides. The light-blocking layer may be a film containing a resin material or a thin film of an inorganic material such as a metal. Stacked films containing the material of the coloring layer can also be used for the light-blocking layer. For example, a stacked-layer structure of a film containing a material for a coloring layer that transmits light of a certain color and a film containing a material for a coloring layer that transmits light of another color can be employed. It is preferable that the coloring layer and the light-blocking layer be formed using the same material because the same manufacturing apparatus can be used and the process can be simplified.

The structure described in this embodiment can be combined as appropriate with any of the structures described in the other embodiments.

Embodiment 7

In this embodiment, electronic devices each including the light-emitting element described in Embodiment 3 and Embodiment 4 are described. The light-emitting element described in Embodiment 3 and Embodiment 4 includes the compound of one embodiment of the present invention and thus has reduced power consumption and high reliability; as a result, the electronic devices described in this embodiment can each include a display portion having reduced power consumption and high reliability. In addition, the electronic devices can have low driving voltage since the light-emitting element described in Embodiment 3 and Embodiment 4 has low driving voltage.

Examples of the electronic device including the above light-emitting element include television devices (also referred to as TV or television receivers), monitors for computers and the like, cameras such as digital cameras and digital video cameras, digital photo frames, cellular phones (also referred to as mobile phones or mobile phone devices), portable game machines, portable information terminals, audio playback devices, and large game machines such as pachinko machines. Specific examples of these electronic devices are described below.

Figure 12A:
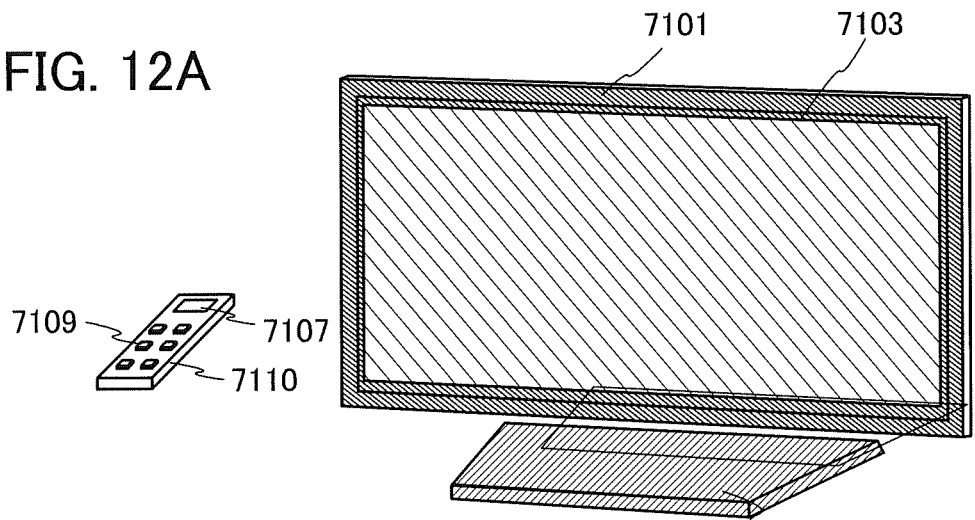
FIGS. 12A to 12D each illustrate an electronic device of one embodiment of the present invention.

FIG. 12A illustrates an example of a television device. In the television device, a display portion 7103 is incorporated in a housing 7101. In addition, here, the housing 7101 is supported by a stand 7105. The display portion 7103 enables display of images and includes light-emitting elements which are the same as the light-emitting element described in Embodiment 3 and Embodiment 4 and arranged in a matrix. The light-emitting elements each include the organic compound of one embodiment of the present invention and thus can have high emission efficiency and low driving voltage. Therefore, the television device including the display portion 7103 which is formed using the light-emitting elements can have reduced power consumption and low driving voltage.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the television set is connected to a communication network with or without wires via the modem, one-way (from a sender to a receiver) or two-way (between a sender and a receiver or between receivers) information communication can be performed.

Figure 12B:
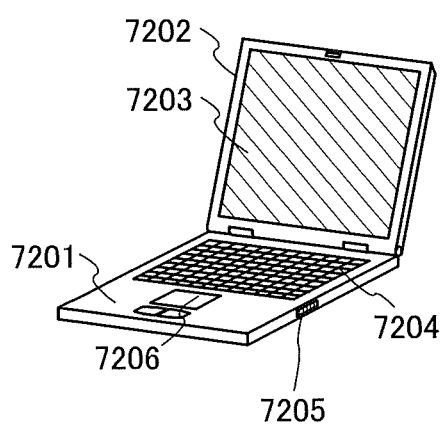

FIG. 12B illustrates a computer including a main body 7201, a housing 7202, a display portion 7203, a keyboard 7204, an external connection port 7205, a pointing device 7206, and the like. Note that this computer is manufactured by using light-emitting elements which are the same as the light-emitting element described in Embodiment 3 or 4 and arranged in a matrix in the display portion 7203. The light-emitting elements each include the compound of one embodiment of the present invention and thus can have high emission efficiency and low driving voltage. Therefore, the computer including the display portion 7203 which is formed using the light-emitting elements can have reduced power consumption and low driving voltage.

Figure 12C:
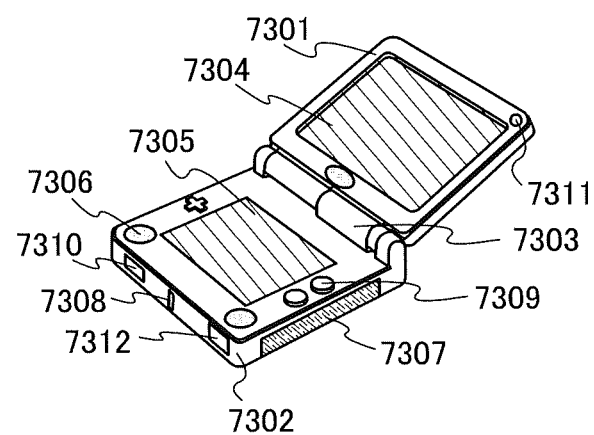

FIG. 12C illustrates a portable game machine having two housings, a housing 7301 and a housing 7302, which are connected with a joint portion 7303 so that the portable game machine can be opened or folded. A display portion 7304 including light-emitting elements which are the same as the light-emitting element described in Embodiment 3 and Embodiment 4 and arranged in a matrix is incorporated in the housing 7301, and a display portion 7305 is incorporated in the housing 7302. In addition, the portable game machine illustrated in FIG. 12C includes a speaker portion 7306, a recording medium insertion portion 7307, an LED lamp 7308, an input unit (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the display portion in which the light-emitting elements described in Embodiment 3 and Embodiment 4 are arranged in a matrix is used as either the display portion 7304 or the display portion 7305, or both, and the structure can include other accessories as appropriate. The portable game machine illustrated in FIG. 12C has a function of reading out a program or data stored in a recoding medium to display it on the display portion, and a function of sharing information with another portable game machine by wireless communication. Note that the portable game machine illustrated in FIG. 12C is not limited to the above, and the portable game machine can have a variety of functions. Since the light-emitting elements used in the display portion 7304 have high emission efficiency by including the compound of one embodiment of the present invention, the portable game machine including the above-described display portion 7304 can have reduced power consumption. Since the light-emitting elements used in the display portion 7304 each have low driving voltage by including the compound of one embodiment of the present invention, the portable game machine can also have low driving voltage.

Figure 12D:
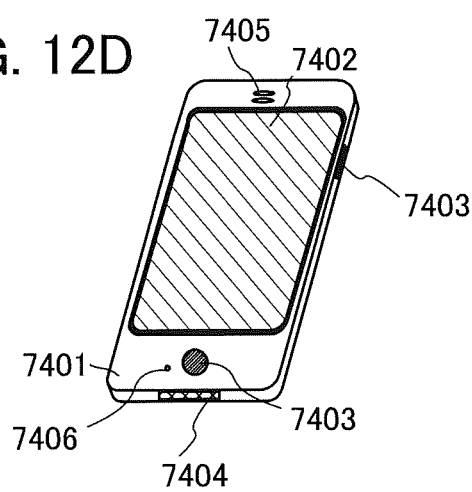

FIG. 12D illustrates an example of a cellular phone. The cellular phone is provided with a display portion 7402 incorporated in a housing 7401, operation buttons 7403, an external connection port 7404, a speaker 7405, a microphone 7406, and the like. Note that the cellular phone includes the display portion 7402 including light-emitting elements which are the same as the light-emitting element described in Embodiment 3 and Embodiment 4 and arranged in a matrix. The light-emitting elements each include the compound of one embodiment of the present invention and thus can have high emission efficiency and low driving voltage. Therefore, the cellular phone including the display portion 7402 which is formed using the light-emitting elements can have reduced power consumption and low driving voltage.

When the display portion 7402 of the cellular phone illustrated in FIG. 12D is touched with a finger or the like, data can be input into the cellular phone. In this case, operations such as making a call and creating e-mail can be performed by touching the display portion 7402 with a finger or the like.

There are mainly three screen modes of the display portion 7402. The first mode is a display mode mainly for displaying an image. The second mode is an input mode mainly for inputting data such as text. The third mode is a display-and-input mode in which two modes of the display mode and the input mode are combined.

For example, in the case of making a call or creating e-mail, a text input mode mainly for inputting text is selected for the display portion 7402 so that text displayed on a screen can be input. In this case, it is preferable to display a keyboard or number buttons on almost the entire screen of the display portion 7402.

When a sensing device which includes a sensor for sensing inclination, such as a gyroscope sensor or an acceleration sensor, is provided inside the cellular phone, display on the screen of the display portion 7402 can be automatically changed by determining the orientation of the cellular phone (whether the cellular phone is placed horizontally or vertically).

The screen modes are switched by touching the display portion 7402 or operation with the operation buttons 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal sensed by an optical sensor in the display portion 7402 is sensed, the screen mode may be controlled so as to be switched from the input mode to the display mode.

The display portion 7402 may also function as an image sensor. For example, an image of a palm print, a fingerprint, or the like is taken by touch on the display portion 7402 with the palm or the finger, whereby personal authentication can be performed. Furthermore, by providing a backlight or a sensing light source which emits near-infrared light in the display portion, an image of a finger vein, a palm vein, or the like can be taken.

Note that the structure described in this embodiment can be combined with any of the structures described in Embodiments 1 to 4 as appropriate.

As described above, the application range of the light-emitting device including the light-emitting element described in Embodiment 3 and Embodiment 4 which includes the compound of one embodiment of the present invention is wide so that this light-emitting device can be used in electronic devices in a variety of fields. By using the compound, an electronic device having reduced power consumption and low driving voltage can be obtained.

The light-emitting element including the compound of one embodiment of the present invention can also be used for a light source device. One mode is described with reference to FIG. 13. Note that the light source device includes a light-emitting element including the compound of one embodiment of the present invention as a light irradiation unit and at least includes an input-output terminal portion which supplies current to the light-emitting element. Furthermore, the light-emitting element is preferably shielded from the outside atmosphere by sealing.

FIG. 13 illustrates an example of a liquid crystal display device using the light-emitting elements including the compound of one embodiment of the present invention for a backlight. The liquid crystal display device illustrated in FIG. 13 includes a housing 901, a liquid crystal layer 902, a backlight 903, and a housing 904. The liquid crystal layer 902 is connected to a driver IC 905. The light-emitting element including the above compound is used for the backlight 903, to which current is supplied through a terminal 906.

The light-emitting element including the above compound is used for the backlight of the liquid crystal display device; thus, the backlight can have reduced power consumption. In addition, the use of the light-emitting element including the above compound enables fabrication of a planar-emission lighting device and further a larger-area planar-emission lighting device; thus, the backlight can be a larger-area backlight, and the liquid crystal display device can also be a larger-area device. Furthermore, with the backlight using the light-emitting element including the above compound, the light-emitting device can be thinner than a conventional one; accordingly, the display device can also be thinner.

Figure 14:
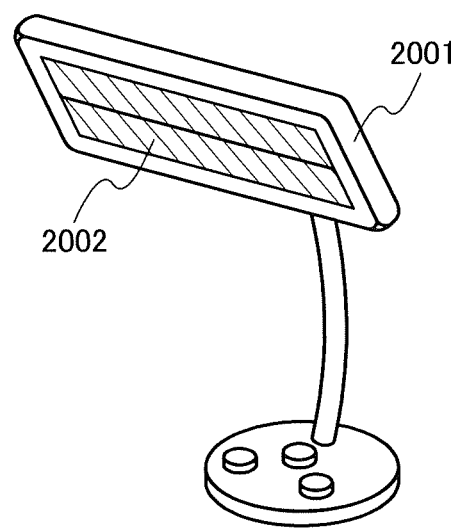
FIG. 14 illustrates a lighting device of one embodiment of the present invention.

FIG. 14 illustrates an example in which the light-emitting element including the compound of one embodiment of the present invention is used for a table lamp which is a lighting device. The table lamp illustrated in FIG. 14 includes a housing 2001 and a light source 2002, and the light-emitting element including the above compound is used for the light source 2002.

Figure 15:
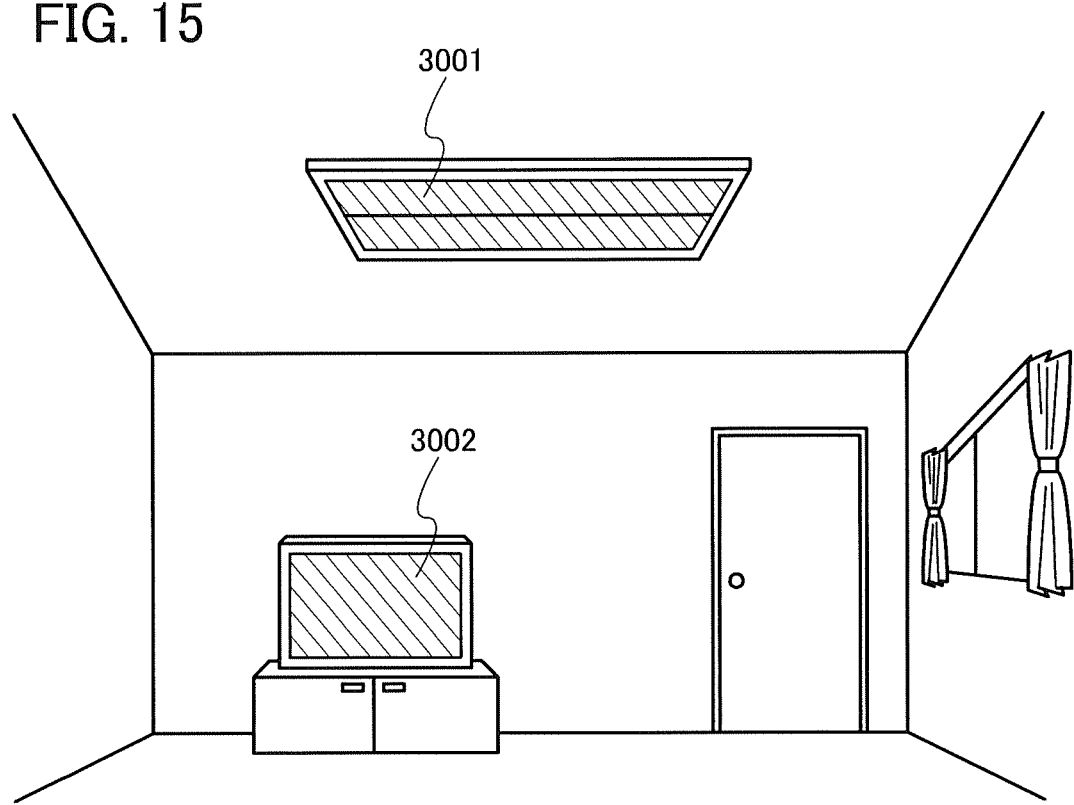
FIG. 15 illustrates a lighting device of one embodiment of the present invention.

FIG. 15 illustrates an example in which the light-emitting element including the compound of one embodiment of the present invention is used for an indoor lighting device 3001. Since the light-emitting element including the above compound has reduced power consumption, a lighting device that has reduced power consumption can be obtained. Furthermore, since the light-emitting element including the above compound can have a large area, the light-emitting element can be used for a large-area lighting device. Furthermore, since the light-emitting element including the above compound is thin, a lighting device having a reduced thickness can be fabricated. FIG. 15 also illustrates an example in which the light-emitting element including the compound of one embodiment of the present invention is used for a display device 3002.

Figure 16:
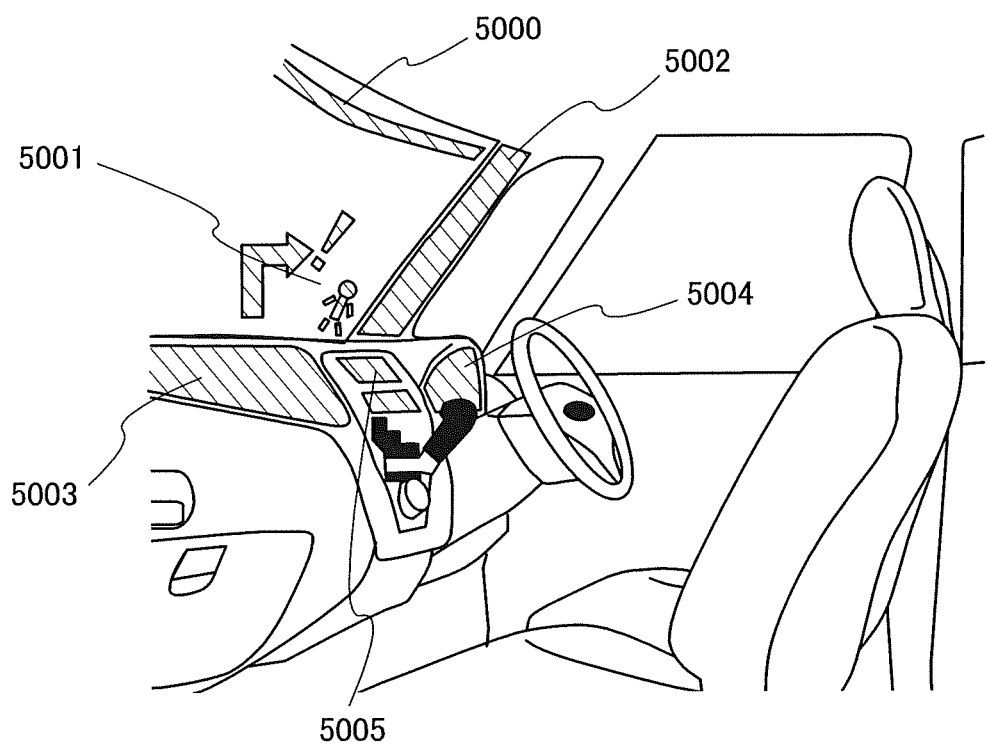
FIG. 16 illustrates in-vehicle display devices and lighting devices of one embodiment of the present invention.

The light-emitting element including the compound of one embodiment of the present invention can also be used for an automobile windshield or an automobile dashboard. FIG. 16 illustrates one mode in which the light-emitting elements including the above compound are used for an automobile windshield and an automobile dashboard. Display regions 5000 to 5005 each include the light-emitting element including the above compound.

The display regions 5000 and 5001 are display devices which are provided in the automobile windshield and in which light-emitting elements including the above compound are incorporated. The light-emitting element including the above compound can be formed into what is called a see-through display device, through which the opposite side can be seen, by including a first electrode and a second electrode formed of electrodes having light-transmitting properties. Such see-through display devices can be provided even in the automobile windshield, without hindering the vision. Note that in the case where a driving transistor or the like is provided, a transistor having a light-transmitting property, such as an organic transistor using an organic semiconductor material or a transistor using an oxide semiconductor, is preferably used.

The display region 5002 is a display device which is provided in a pillar portion and in which the light-emitting element including the above compound is incorporated. The display region 5002 can compensate for the view hindered by the pillar portion by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation data, a speedometer, a tachometer, a mileage, a fuel meter, a gearshift indicator, and air-condition setting. The content or layout of the display can be changed freely by a user as appropriate. Note that such information can also be shown by the display regions 5000 to 5003. The display regions 5000 to 5005 can also be used as lighting devices.

The compound of one embodiment of the present invention can be used for an electronic device such as an organic thin film solar cell. Specifically, the compound can be used in a carrier-transport layer or a carrier-injection layer since the compound has a carrier-transport property. The compound can be photoexcited and hence can be used in a power generation layer.

Example 1

In this example, a method for synthesizing N,N'-bis[4-(6-phenylbenzo[b]naphtho[1,2-d]furan-8-yl)phenyl]-4-amino-p-terphenyl (abbreviation: BnfBB1TP), which is the organic compound of one embodiment of the present invention represented by Structural Formula (103), and the physical properties of the compound are described.

Synthesis Example 1

Step 1: Synthesis of 4-(4-biphenylyl)triphenylamine

Into a 1000-mL three-neck flask were put 28 g (85 mmol) of 4-bromotriphenylamine, 17 g (85 mmol) of 4-biphenylboronic acid, 0.92 g (3.0 mmol) of tri(ortho-tolyl)phosphine, 340 mL of toluene, 85 mL of ethanol, and 100 mL of an aqueous solution of potassium carbonate (2.0 mol/L). The mixture was degassed under reduced pressure and then, a nitrogen gas was made to flow continuously in the system. The mixture was heated to 60° C. Then, 0.22 g (1.0 mmol) of palladium(II) acetate was added and the mixture was stirred at 80° C. for 5.5 hours. After the stirring, the mixture was cooled to room temperature, and the precipitated solid was collected by suction filtration and washed with water, ethanol, and toluene to give 29 g of a target pale brown solid in a yield of 86%. Synthesis Scheme of Step 1 is shown in (A-1) below.

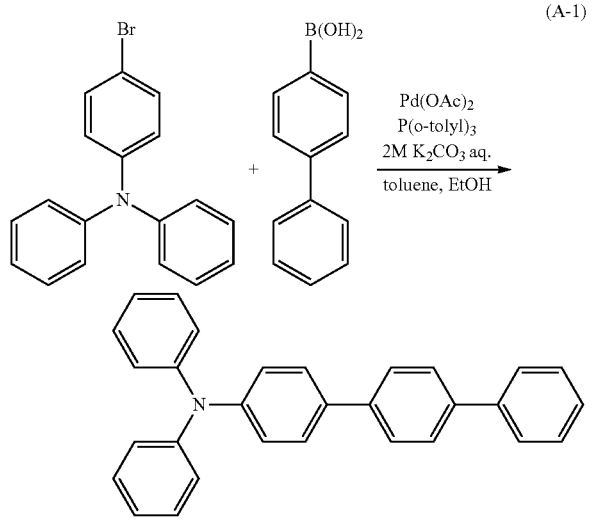

(A-1)

Step 2: Synthesis of N,N'-bis(4-bromophenyl)-4-amino-p-terphenyl

Into a 2-L conical flask were put 12 g (30 mmol) of 4-(4-biphenylyl)triphenylamine and 1.5 L of ethyl acetate. The mixture was heated and stirred to well dissolve 4-(4-biphenylyl)triphenylamine. After dissolution was visually checked, 11 g (60 mmol) of N-bromosuccinimide (NBS) was added and then this solution was stirred at room temperature for two days. After the stirring, the obtained solution was washed with water and saturated saline and then magnesium sulfate was added to perform drying. This mixture was gravity-filtered, and the obtained filtrate was concentrated to give 12 g of a target white solid in a yield of 73%. Synthesis Scheme of Step 2 is shown in (A-2) below.

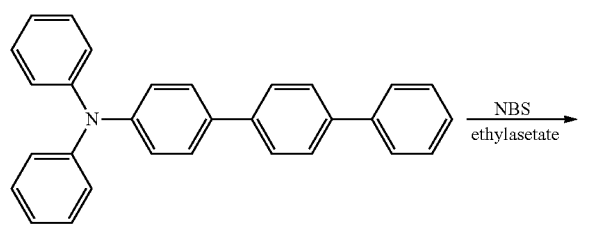

(A-2)

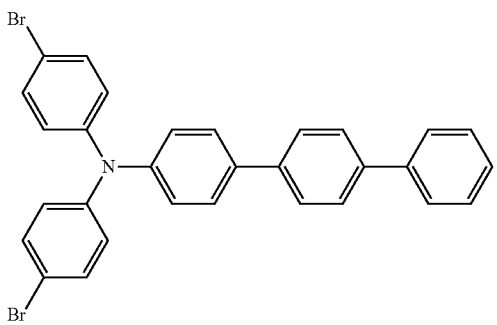

The obtained solid was subjected to nuclear magnetic resonance spectrometry ($^1$H NMR), and the results are shown below.

$^1$H NMR (chloroform-d, 500 MHz): δ=7.0 (d, J=9.0 Hz, 4H), 7.13 (d, J=8.5 Hz, 2H), 7.37 (d, J=8.5 Hz, 5H), 7.46 (t, J=8.0 Hz, 2H), 7.54 (d, J=8.0 Hz, 2H), 7.63-7.68 (m, 6H).

Figure 17A:
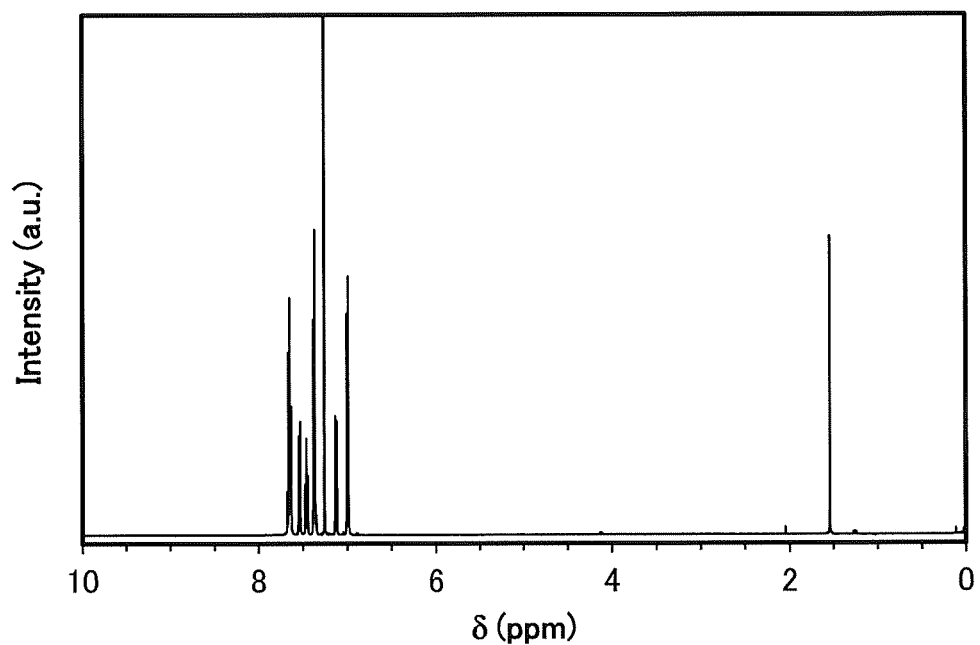
FIGS. 17A and 17B show NMR charts of a compound in Example.
Figure 17B:
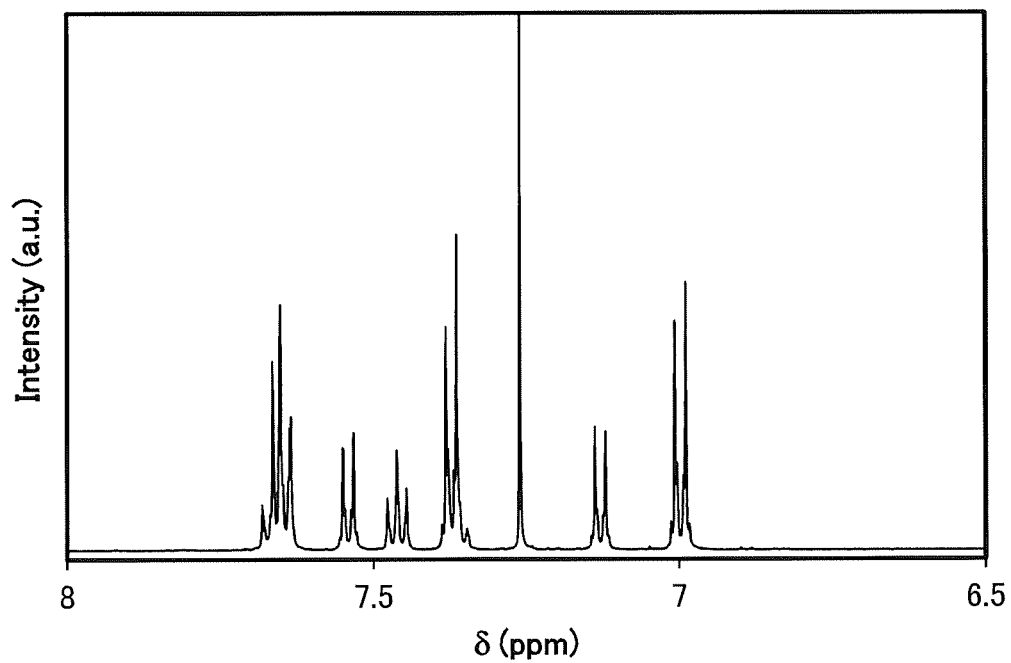

FIGS. 17A and 17B are $^1$H NMR charts of the obtained solid. Note that FIG. 17B is a chart showing an enlarged part in the range of 6.5 ppm to 8.0 ppm of FIG. 17A. The results revealed that N,N'-bis(4-bromophenyl)-4-amino-p-terphenyl, which was the target substance, was obtained.

Step 3: Synthesis of N,N'-bis[4-(6-phenylbenzo[b]naphtho[1,2-d]furan-8-yl)phenyl]-4-amino-p-terphenyl (abbreviation: BnfBB1TP)

Into a 200-mL three-neck flask were put 1.4 g (2.5 mmol) of N,N'-bis(4-bromophenyl)-4-amino-p-terphenyl, 1.7 g (5.0 mmol) of 6-phenylbenzo[b]naphtho[1,2-d]furan-8-boronic acid, 0.11 g (0.40 mmol) of tri(ortho-tolyl)phosphine, 20 mL of toluene, 5 mL of ethanol, and 5 mL of an aqueous solution of potassium carbonate (2.0 mol/L). The mixture was degassed under reduced pressure and then, a nitrogen gas was made to flow continuously in the system. The mixture was heated to 60° C. Then, 50 mg (0.20 mmol) of palladium(II) acetate was added and the mixture was stirred at 80° C. for 1.5 hours. After the stirring, the precipitated solid was collected by suction filtration and washed with toluene, water, and ethanol to give 1.0 g of a brown powder in a yield of 41%. Synthesis Scheme of Step 3 is shown in (A-3) below.

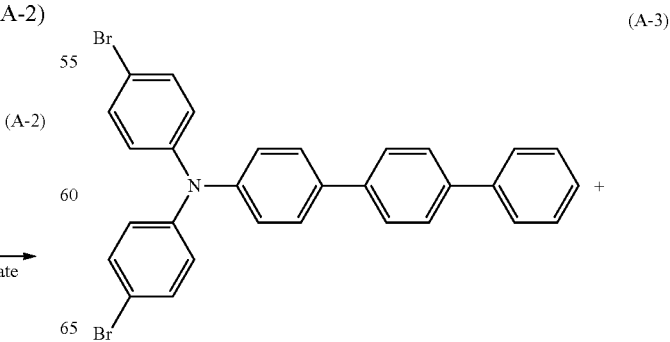

(A-3)

-continued

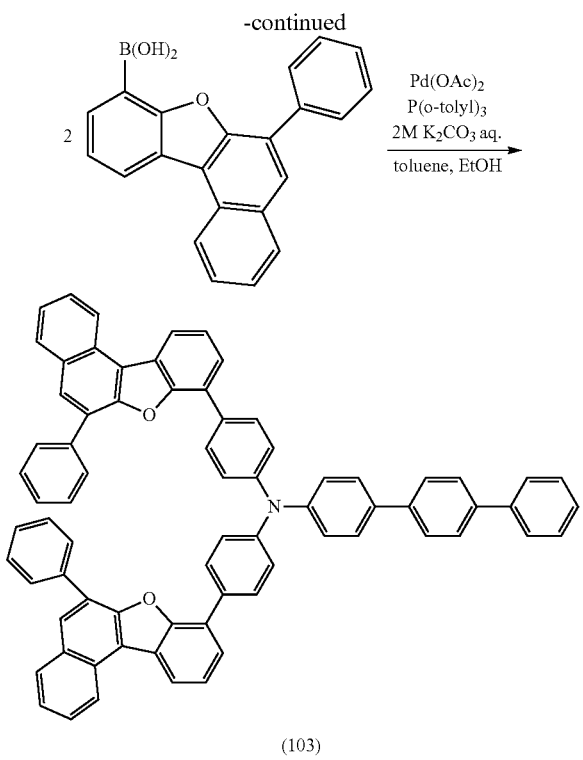

(103)

By a train sublimation method, 1.0 g of the obtained brown powder was purified. In the sublimation purification, the brown powder was heated at 430° C. for 15 hours under a pressure of $3.2 \times 10^{-2}$ Pa. After the sublimation purification, 0.65 g of a target pale yellow solid was obtained at a collection rate of 63%.

The obtained solid was subjected to nuclear magnetic resonance spectrometry ($^1$H NMR), and the results are shown below.

$^1$H NMR (dichloromethane-$d_2$, 500 MHz): δ=7.34-7.39 (m, 7H), 7.41 (t, J=7.5 Hz, 2H), 7.46 (t, J=7.5 Hz, 2H), 7.53 (t, J=7.5 Hz, 4H), 7.58-7.63 (m, 4H), 7.65-7.68 (m, 4H), 7.72-7.78 (m, 8H), 7.97 (d, J=9.0 Hz, 4H), 8.06 (d, J=7.5 Hz, 4H), 8.11 (t, J=4.0 Hz, 4H), 8.43 (d, J=8.0 Hz, 2H), 8.71 (d, J=8.0 Hz, 2H).

Figure 18A:
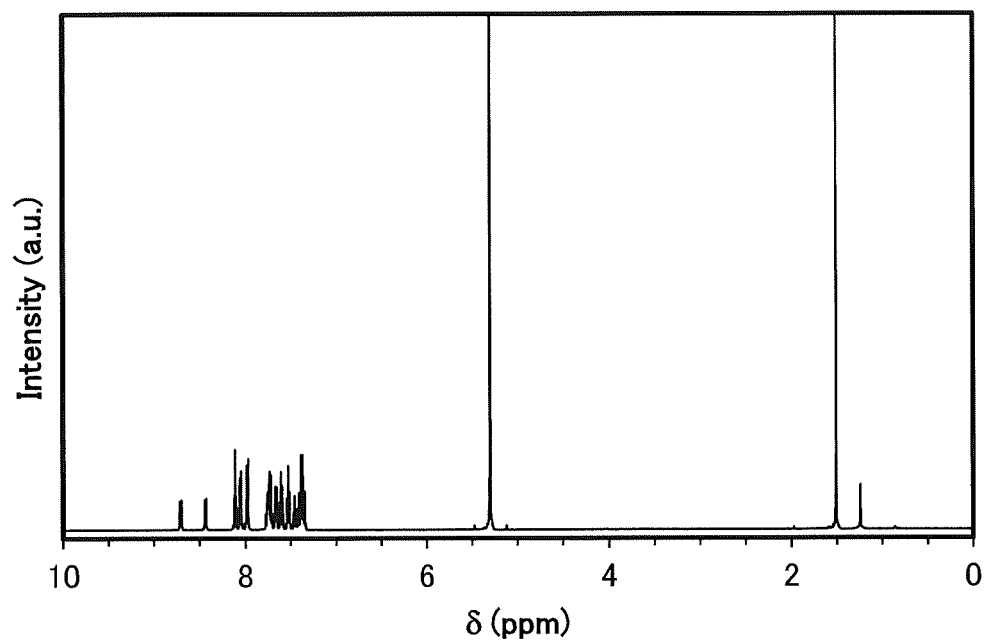
FIGS. 18A and 18B show NMR charts of a compound in Example.
Figure 18B:
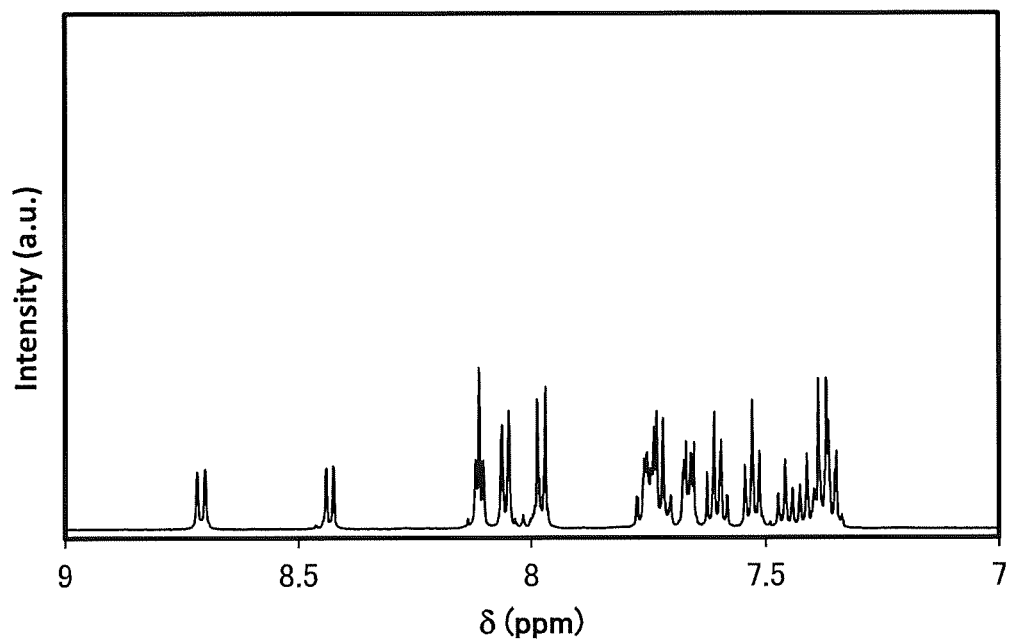

FIGS. 18A and 18B are $^1$H NMR charts of the obtained solid. Note that FIG. 18B is a chart showing an enlarged part in the range of 7.0 ppm to 9.0 ppm of FIG. 18A. The results revealed that BnfBB1TP, which was the target substance, was obtained.

<Properties of BnfBB1TP>

Figure 19:
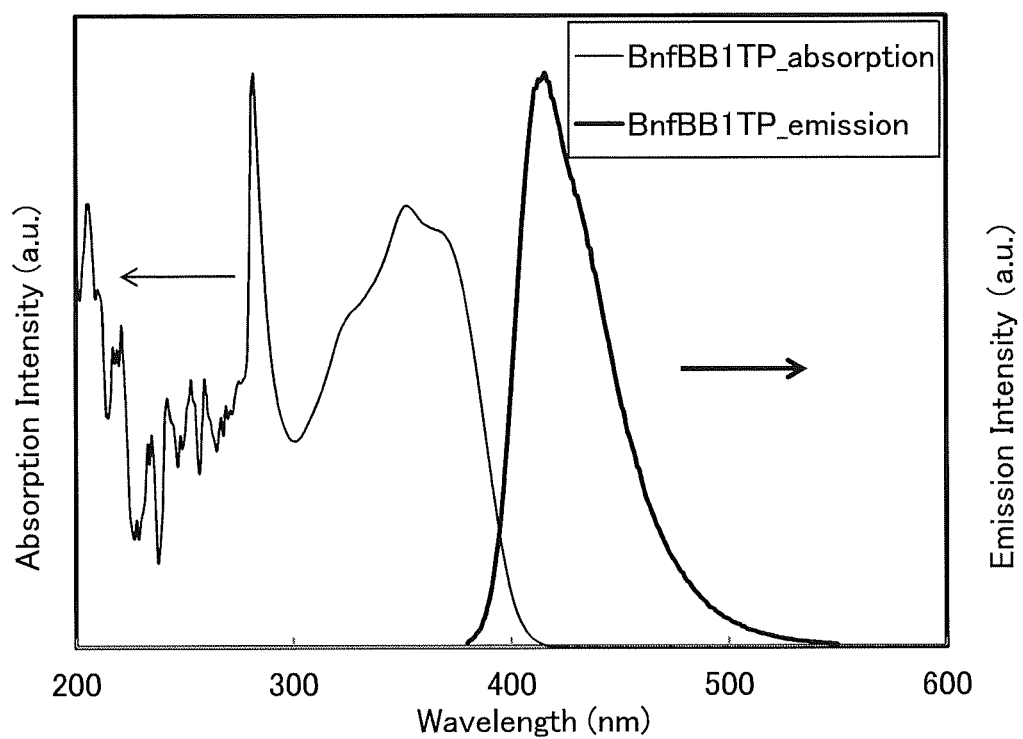
FIG. 19 shows absorption and emission spectra of a compound in Example.
Figure 20:
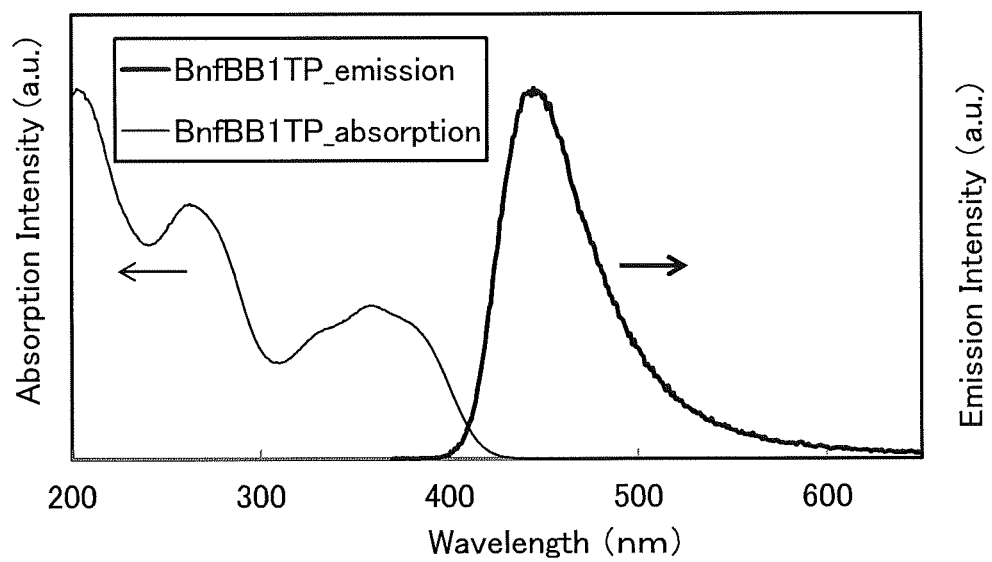
FIG. 20 shows absorption and emission spectra of a compound in Example.

FIG. 19 shows an absorption spectrum and an emission spectrum of BnfBB1TP in a toluene solution. FIG. 20 shows an absorption spectrum and an emission spectrum of a thin film of BnfBB1TP. The solid thin film was formed over a quartz substrate by a vacuum evaporation method. The absorption spectrum of the toluene solution was measured using an ultraviolet-visible light spectrophotometer (V550 type manufactured by JASCO Corporation). The absorption spectrum of BnfBB1TP in the toluene solution shown in FIG. 19 was obtained by subtracting an absorption spectrum of toluene only put in a quartz cell from the absorption spectrum of BnfBB1TP in the toluene solution. The absorption spectrum of the thin film was measured using a spectrophotometer (U-4100 Spectrophotometer, manufactured by Hitachi High-Technologies Corporation). The emission spectrum was measured using a fluorescence spectrophotometer (FS920 manufactured by Hamamatsu Photonics K.K.).

As shown in FIG. 19, BnfBB1TP in the toluene solution has absorption peaks at around 370 nm, 352 nm, and 324 nm, and an emission wavelength peak at 416 nm (excitation wavelength: 370 nm). As shown in FIG. 20, the thin film of BnfBB1TP has absorption peaks at around 383 nm, 360 nm, 332 nm, and 266 nm, and an emission wavelength peak at around 446 nm (excitation wavelength: 365 nm). It was found that BnfBB1TP emitted blue light. The compound of one embodiment of the present invention can be used as a host material for a light-emitting substance or a host material for a substance emitting fluorescence in the visible region.

It was found that aggregation of the thin film of BnfBB1TP is not easily caused even under the air and the thin film suffers only a small change in shape and has high film quality.

The HOMO level and the LUMO level of BnfBB1TP were obtained through a cyclic voltammetry (CV) measurement. A calculation method is described below.

An electrochemical analyzer (ALS model 600A or 600C, manufactured by BAS Inc.) was used as a measurement apparatus. As for a solution used for the CV measurement, dehydrated dimethylformamide (DMF, manufactured by Sigma-Aldrich Inc., 99.8%, catalog No. 22705-6) was used as a solvent, and tetra-n-butylammonium perchlorate (n-Bu$_4$NClO$_4$, manufactured by Tokyo Chemical Industry Co., Ltd., catalog No. T0836), which was a supporting electrolyte, was dissolved in the solvent such that the concentration of tetra-n-butylammonium perchlorate was 100 mmol/L. Furthermore, the object to be measured was also dissolved in the solvent such that the concentration thereof was 2 mmol/L. A platinum electrode (PTE platinum electrode, manufactured by BAS Inc.) was used as a working electrode, another platinum electrode (Pt counter electrode for VC-3, (5 cm), manufactured by BAS Inc.) was used as an auxiliary electrode, and an Ag/Ag$^+$ electrode (RE7 reference electrode for nonaqueous solvent, manufactured by BAS Inc.) was used as a reference electrode. Note that the measurement was performed at a room temperature (20° C. to 25° C.). In addition, the scan speed at the CV measurement was set to 0.1 V/sec, and an oxidation potential Ea [V] and a reduction potential Ec [V] with respect to the reference electrode were measured. Note that Ea represents an intermediate potential of an oxidation-reduction wave, and Ec represents an intermediate potential of a reduction-oxidation wave. Here, the potential energy of the reference electrode used in this example with respect to the vacuum level is found to be -4.94 [eV], and thus, the HOMO level and the LUMO level can be obtained from the following formula: HOMO level [eV]=-4.94-Ea and LUMO level [eV]=-4.94-Ec.

Furthermore, the CV measurement was repeated 100 times, and the oxidation-reduction wave at the hundredth cycle and the oxidation-reduction wave at the first cycle were compared with each other to examine the electric stability of the compound.

As a result, in the measurement of an oxidation potential Ea [V] of BnfBB1TP, the HOMO level was -5.50 eV. In contrast, the LUMO level was -2.52 eV. When the oxidation-reduction wave was repeatedly measured, in the Ea measurement, the peak intensity of the oxidation-reduction wave after the hundredth cycle was maintained to be 79% of that of the oxidation-reduction wave at the first cycle, and in the Ec measurement, the peak intensity of the oxidation-reduction wave after the hundredth cycle was maintained to be 69% of that of the oxidation-reduction wave at the first cycle; thus, resistance to oxidation and reduction of BnfBB1TP was found to be extremely high.

Furthermore, differential scanning calorimetry (DSC measurement) of BnfBB1TP was performed by Pyris1DSC manufactured by PerkinElmer, Inc. In the differential scanning calorimetry, after the temperature was raised from −10° C. to 320° C. at a temperature rising rate of 40° C./min, the temperature was held for a minute and then lowered to −10° C. at a temperature reduction rate of 50° C./min. This operation was repeated twice successively.

It was found from the DSC measurement result of the second cycle that the glass transition point, the crystallization temperature, and the melting point of BnfBB1TP are 163° C., 215° C., and 307° C., respectively, that is, BnfBB1TP has extremely high heat resistance.

The thermogravimetry-differential thermal analysis (TG-DTA) was performed on BnfBB1TP. The measurement was performed using a high vacuum differential type differential thermal balance (TG-DTA2410SA, manufactured by Bruker AXS K.K.). The measurement was performed under atmospheric pressure at a temperature rising rate of 10° C./min under a nitrogen stream (a flow rate of 200 mL/min). In the thermogravimetry-differential thermal analysis, the temperature (decomposition temperature) at which the weight obtained by thermogravimetry was reduced by 5% of the weight at the beginning of the measurement was found to be 500° C. or higher, which shows that BnfBB1TP is a substance with high heat resistance.

Example 2

In this example, a method for synthesizing 4,4'-bis(6-phenylbenzo[b]naphtho[1,2-d]furan-8-yl)-4''-phenyltriphenylamine (abbreviation: BnfBB1BP), which is the organic compound of one embodiment of the present invention represented by Structural Formula (102), and the physical properties of the compound are described.

Synthesis Example 2

Step 1: Synthesis of 4,4'-bis(6-phenylbenzo[b]naphtho[1,2-d]furan-8-yl)-4''-phenyltriphenylamine (abbreviation: BnfBB1BP)

Into a 200-mL three-neck flask were put 1.4 g (3.0 mmol) of 4,4'-dibromo-4''-phenyltriphenylamine, 2.0 g (6.0 mmol) of 6-phenylbenzo[b]naphtho[1,2-d]furan-8-boronic acid, 0.31 g (1.0 mmol) of tri(ortho-tolyl)phosphine, 12 mL of toluene, 3 mL of ethanol, and 5 mL of an aqueous solution of potassium carbonate (2.0 mol/L). The mixture was degassed under reduced pressure and then, a nitrogen gas was made to flow continuously in the system. The mixture was heated to 60° C. Then, 73 mg (0.32 mmol) of palladium (II) acetate was added and the mixture was stirred at 80° C. for 6.5 hours. After the stirring, the precipitated solid was collected by suction filtration and washed with toluene, water, and ethanol. The obtained solid was purified by high performance liquid chromatography (mobile phase: chloroform) to give 1.1 g of a target pale yellow solid in a yield of 42%. Synthesis Scheme is shown in (B-1) below.

By a train sublimation method, 1.0 g of the obtained solid was purified. In the sublimation purification, the solid was heated at 420° C. for 15 hours under a pressure of 3.6 Pa. After the sublimation purification, 0.93 g of a target pale yellow solid was obtained at a collection rate of 81%.

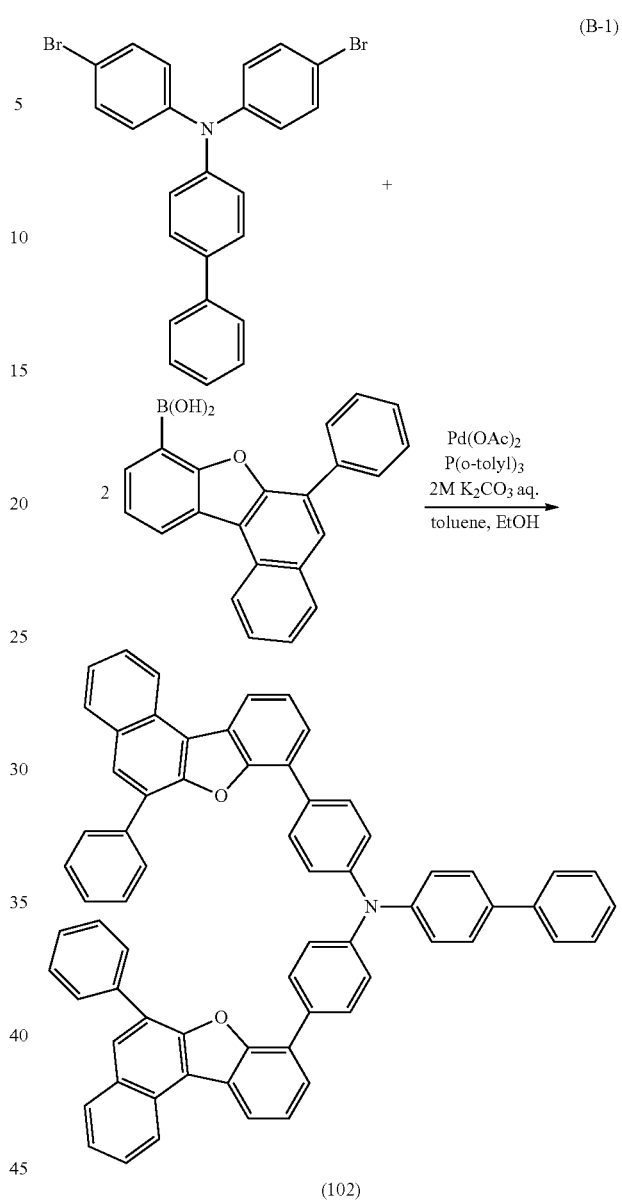

The obtained solid was subjected to nuclear magnetic resonance spectrometry ($^1$H NMR), and the results are shown below.

$^1$H NMR (dichloromethane-d$_2$, 500 MHz): δ=7.33-7.38 (m, 7H), 7.41 (t, J=7.5 Hz, 2H), 7.46 (t, J=7.5 Hz, 2H), 7.52 (t, J=7.5 Hz, 4H), 7.58-7.62 (m, 6H), 7.65 (d, J=7.5 Hz, 2H), 7.74-7.78 (m, 4H), 7.97 (d, J=9.0 Hz, 4H), 8.05 (d, J=8.0 Hz, 4H), 8.11 (t, J=4.0 Hz, 4H), 8.43 (d, J=8.0 Hz, 2H), 8.71 (d, J=8.0 Hz, 2H).

Figure 21A:
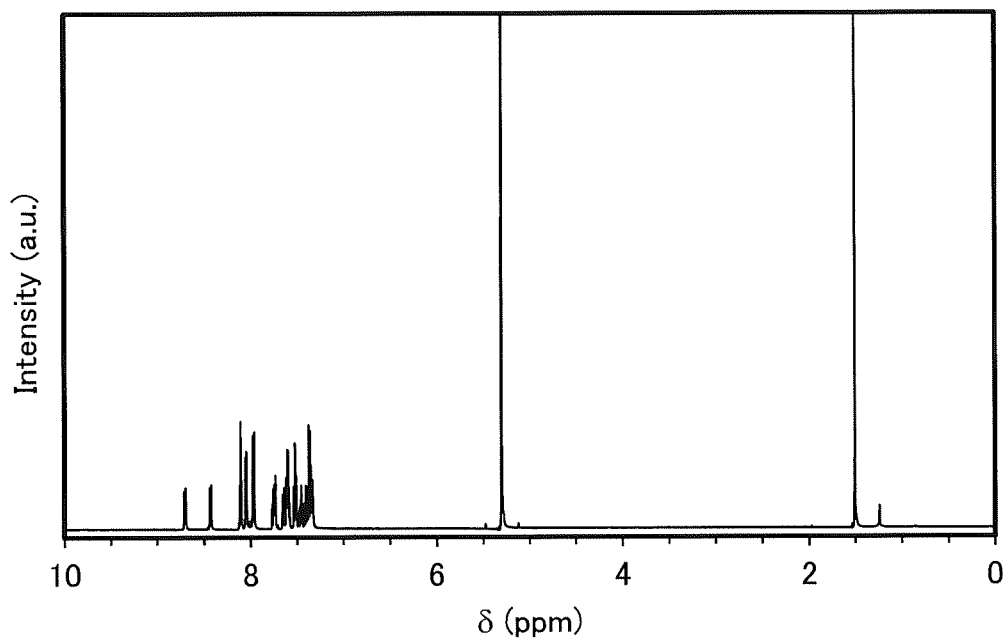
FIGS. 21A and 21B show NMR charts of a compound in Example.
Figure 21B:
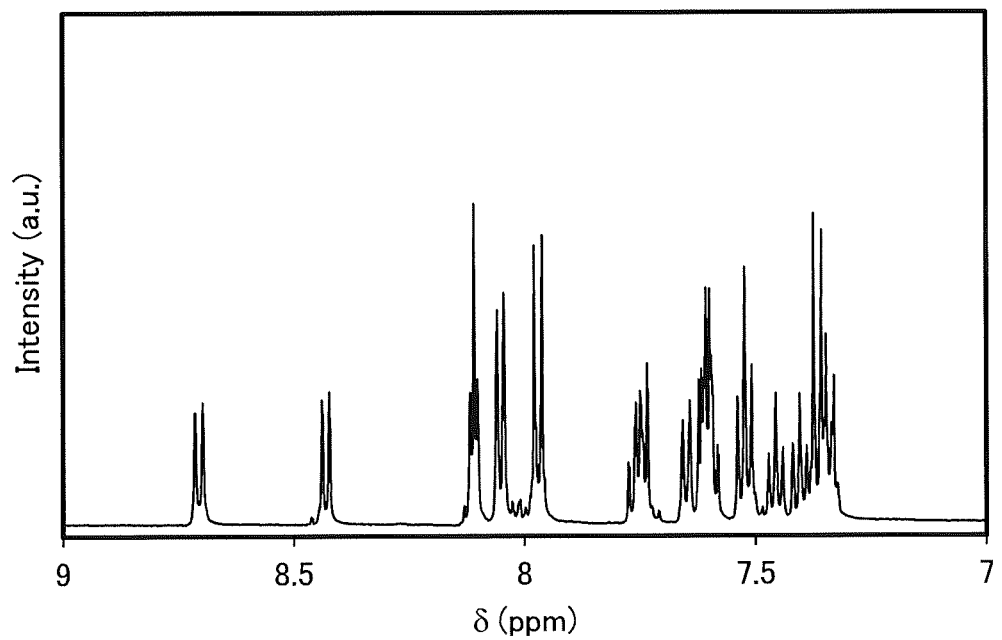

FIGS. 21A and 21B are $^1$H NMR charts of the obtained solid. Note that FIG. 21B is a chart showing an enlarged part in the range of 7.0 ppm to 9.0 ppm of FIG. 21A. The results revealed that BnfBB1BP, which was the target substance, was obtained.

<Properties of BnfBB1BP>

Figure 22:
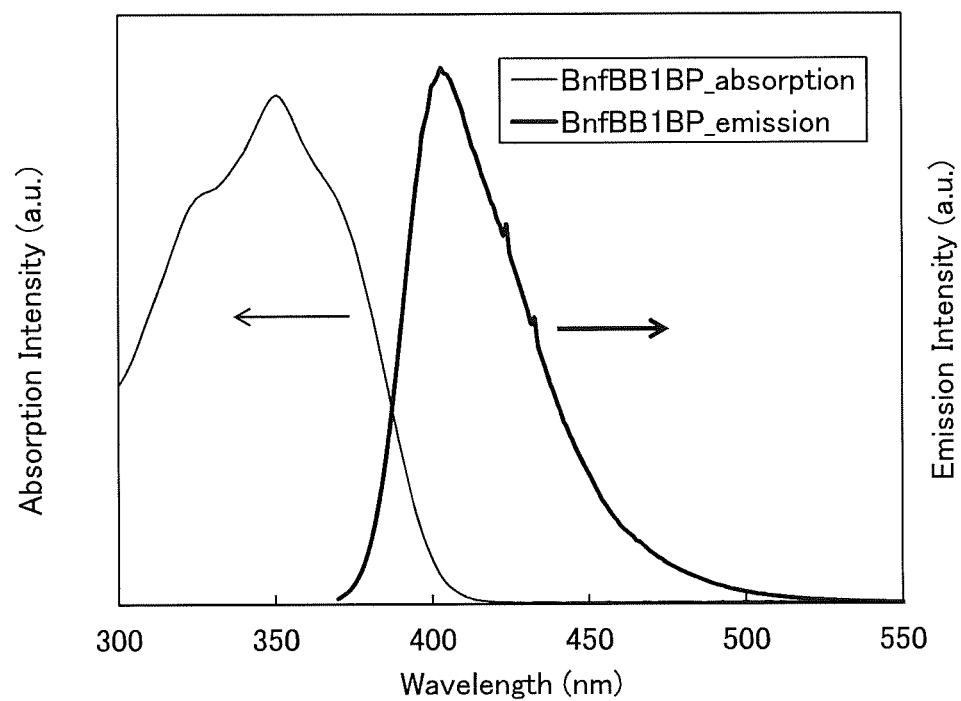
FIG. 22 shows absorption and emission spectra of a compound in Example.
Figure 23:
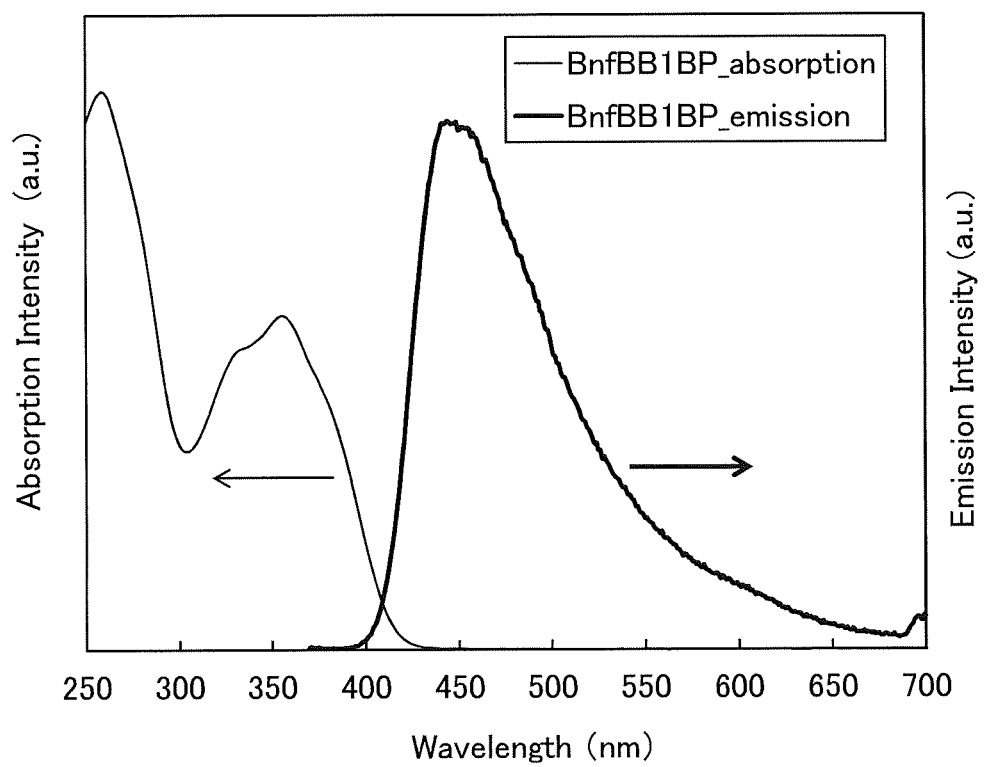
FIG. 23 shows absorption and emission spectra of a compound in Example.

Next, FIG. 22 shows an absorption spectrum and an emission spectrum of BnfBB1BP in a toluene solution. FIG. 23 shows an absorption spectrum and an emission spectrum of a thin film of BnfBB1BP. The measurement was performed in a manner similar to that described in Example 1.

As shown in FIG. 22, BnfBB1BP in the toluene solution has absorption peaks at around 370 nm, 350 nm, and 324 nm, and an emission wavelength peak at 404 nm (excitation wavelength: 360 nm). As shown in FIG. 23, the thin film of BnfBB1BP has absorption peaks at around 382 nm, 355 nm, 330 nm, 278 nm, 257 nm, and 207 nm, and an emission wavelength peak at around 450 nm (excitation wavelength: 370 nm). It was found that BnfBB1BP emitted blue light. The compound of one embodiment of the present invention can be used as a host material for a light-emitting substance or a host material for a substance emitting fluorescence in the visible region.

It was found that aggregation of the thin film of BnfBB1BP is not easily caused even under the air and the thin film suffers only a small change in shape and has high film quality.

Next, the HOMO level and the LUMO level of BnfBB1BP were obtained through a cyclic voltammetry (CV) measurement. A calculation method is similar to that described in Example 1.

Furthermore, the CV measurement was repeated 100 times, and the oxidation-reduction wave at the hundredth cycle and the oxidation-reduction wave at the first cycle were compared with each other to examine the electric stability of the compound.

As a result, in the measurement of an oxidation potential Ea [V] of BnfBB1BP, the HOMO level was −5.51 eV. In contrast, the LUMO level was −2.50 eV. When the oxidation-reduction wave was repeatedly measured, in the Ea measurement, the peak intensity of the oxidation-reduction wave after the hundredth cycle was maintained to be 79% of that of the oxidation-reduction wave at the first cycle, and in the Ec measurement, the peak intensity of the oxidation-reduction wave after the hundredth cycle was maintained to be 77% of that of the oxidation-reduction wave at the first cycle; thus, resistance to oxidation and reduction of BnfBB1BP was found to be extremely high.

Furthermore, differential scanning calorimetry (DSC measurement) of BnfBB1BP was performed. The measurement was performed in a manner similar to that described in Example 1. It was found from the DSC measurement result of the second cycle that the glass transition point of BnfBB1BP is 155° C., that is, BnfBB1BP has extremely high heat resistance.

The thermogravimetry-differential thermal analysis (TG-DTA) was performed on BnfBB1BP. The measurement was performed in a manner similar to that described in Example 1. In the thermogravimetry-differential thermal analysis, the temperature (decomposition temperature) at which the weight obtained by thermogravimetry was reduced by 5% of the weight at the beginning of the measurement was found to be 500° C. or higher, which shows that BnfBB1BP is a substance with high heat resistance.

Example 3

In this example, a method for synthesizing N,N'-bis[4-(dibenzofuran-4-yl)phenyl]-4-amino-p-terphenyl (abbreviation: DBfBB1TP), which was synthesized as a comparative substance for the organic compound of one embodiment of the present invention, and the physical properties of the compound are described.

Synthesis Example 3

Synthesis of N,N-bis[4-(dibenzofuran-4-yl)phenyl]-4-amino-p-terphenyl (abbreviation: DBfBB1TP) represented by Structural Formula (500)

Into a 200-mL three-neck flask were put 2.8 g (5.0 mmol) of N,N-bis(4-bromophenyl)-4-amino-p-terphenyl, 2.1 g (10 mmol) of dibenzofuran-4-boronic acid, 0.63 g (2.0 mmol) of tri(ortho-tolyl)phosphine, 20 mL of toluene, 5 mL of ethanol, and 10 mL of an aqueous solution of potassium carbonate (2.0 mol/L). The mixture was degassed under reduced pressure and then, a nitrogen gas was made to flow continuously in the system. The mixture was heated to 60° C. Then, 97 mg (0.40 mmol) of palladium(II) acetate was added and the mixture was stirred at 80° C. for 8.5 hours. After the stirring, the precipitated solid was collected by suction filtration and washed with toluene, water, and ethanol. An organic layer of the obtained filtrate was washed with water and then with saturated saline, and dried with magnesium sulfate. The mixture was gravity-filtered, and the obtained filtrate was concentrated to give a solid. This solid and the precipitated solid collected after the reaction were purified together by high performance liquid chromatography (mobile phase: chloroform) to give 1.8 g of a target pale yellow solid in a yield of 48%. Synthesis Scheme is shown in (C-1) below.

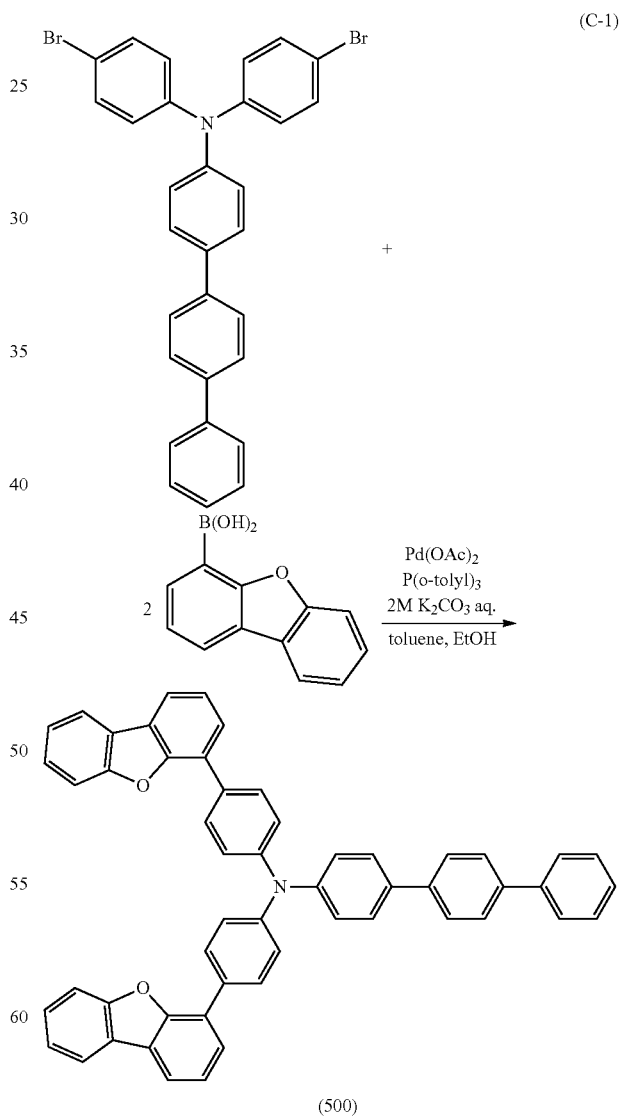

By a train sublimation method, 1.8 g of the obtained solid was purified. In the sublimation purification, the solid was heated at 436° C. for 15 hours under a pressure of 3.7 Pa. After the sublimation purification, 1.6 g of a target pale yellow solid was obtained at a collection rate of 91%.

The obtained solid was subjected to nuclear magnetic resonance spectrometry ($^1$H NMR), and the results are shown below.

$^1$H NMR (chloroform-d, 500 MHz): δ=7.35-7.39 (m, 5H), 7.40 (d, J=9.0 Hz, 4H), 7.44 (t, J=7.5 Hz, 2H), 7.48 (q, J=7.5 Hz, 4H), 7.64 (t, J=7.5 Hz, 7H), 7.67-7.73 (m, 5H), 7.91-7.94 (m, 6H), 8.01 (d, J=7.0 Hz, 2H).

<Properties of DBfBB1TP>

The HOMO level and the LUMO level of DBfBB1TP were obtained through a cyclic voltammetry (CV) measurement. A calculation method is similar to that described in Example 1.

In the measurement of an oxidation potential Ea [V] of DBfBB1TP, the HOMO level was −5.49 eV. In contrast, the LUMO level was −2.31 eV. The LUMO level of each of BnfBB1TP and BnfBB1BP was approximately −2.5 eV; thus, it was found that a substance including a benzo[b]naphtho[1,2-d]furan skeleton can have the LUMO level lower than that of a substance including a dibenzofuran (DBf) skeleton.

It was found from the DSC measurement and the TG-DTA measurement of DBfBB1TP performed in manners similar to those described in Example 1 that the glass transition point is 124° C., the melting point is 258° C., and the decomposition temperature is 483° C. The above results, Example 1, and Example 2 show that BnfBB1TP and BnfBB1BP each including the benzo[b]naphtho[1,2-d]furan skeleton of the present invention have higher heat resistance than DBfBB1TP including a dibenzofuran skeleton. It was also found that the compound of the present invention has a high collection rate in sublimation purification, excellent heat resistance, and a high sublimation property.

Example 4

In this example, fabrication examples of light-emitting elements each including the organic compound of one embodiment of the present invention and characteristics of the light-emitting elements are described. A cross-sectional view of each of the light-emitting elements fabricated in this example is similar to that in FIG. 1B. Table 1 shows details of the element structures. In addition, structures and abbreviations of compounds used here are shown below. Note that Examples described above can be referred to for other compounds.

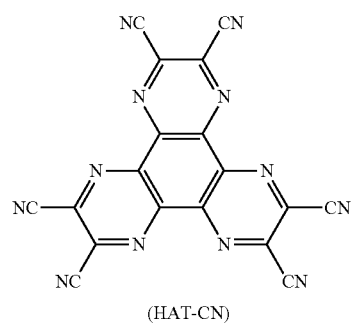

(HAT-CN)

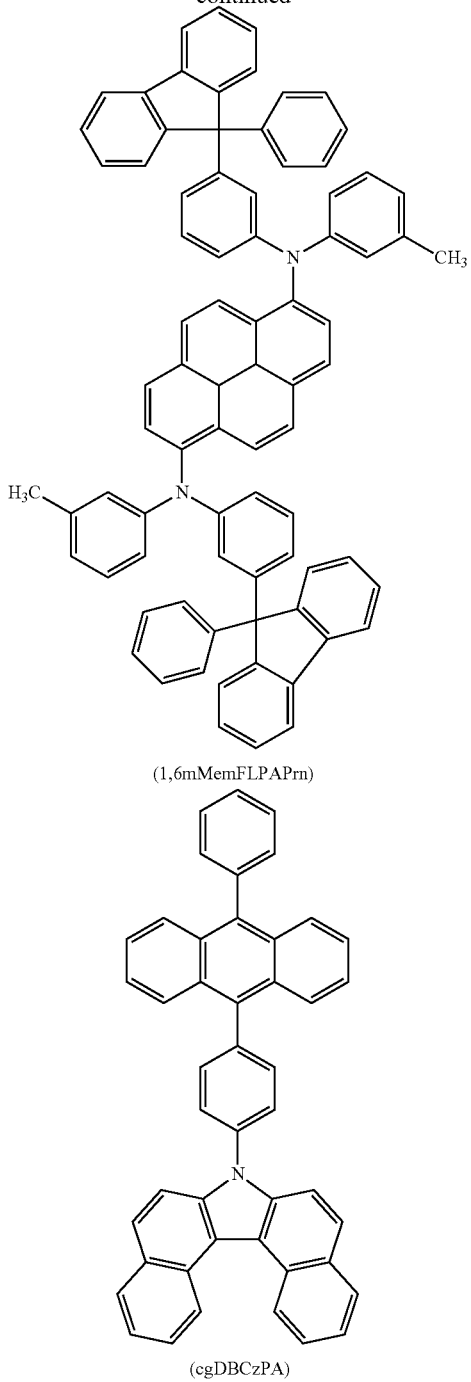

(1,6mMemFLPAPrn)

(cgDBCzPA)

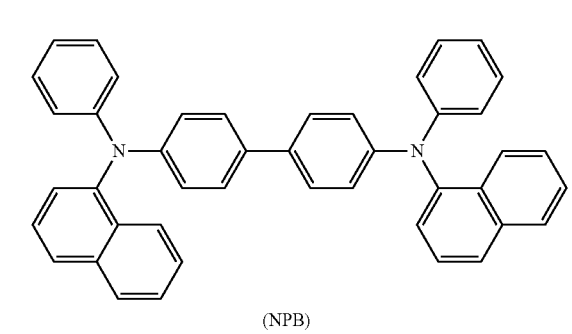

(NPB)

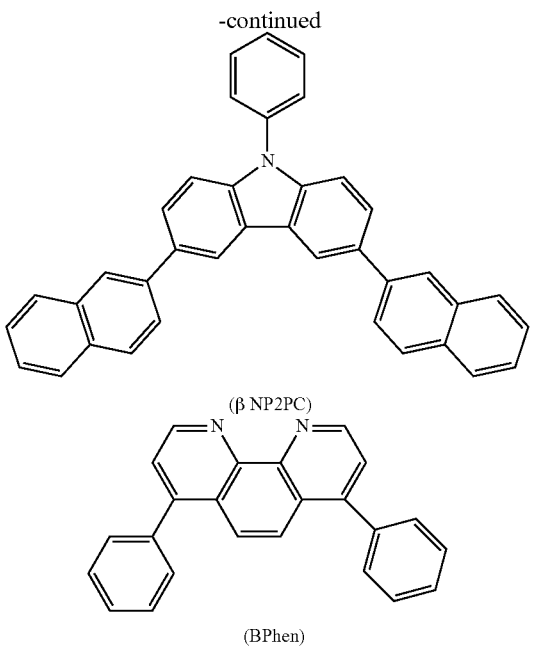

(β NP2PC)

(BPhen)

was deposited over the hole-injection layer 111 by evaporation to a thickness of 10 nm.

Next, as the second hole-transport layer 112-b, N,N-bis[4-(6-phenylbenzo[b]naphtho[1,2-d]furan-8-yl)phenyl]-4-amino-p-terphenyl (abbreviation: BnfBB1TP), which is the organic compound of one embodiment of the present invention, was deposited over the first hole-transport layer 112-a by evaporation to a thickness of 10 nm.

Next, as the third hole-transport layer 112-c, 3,6-bis[4-(2-naphthyl)phenyl]-9-phenyl-9H-carbazole (abbreviation: PNP2PC) was deposited over the second hole-transport layer 112-b by evaporation to a thickness of 10 nm.

Next, as the light-emitting layer 113, 7-[4-(10-phenyl-9-anthryl)phenyl]-7H-dibenzo[c,g]carbazole (abbreviation: cgDBCzPA) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) were deposited over the third hole-transport layer 112-c by co-evaporation to a thickness of 25 nm such that the weight ratio of cgDBCzPA to 1,6mMemFLPAPrn was 1:0.03. In the light-emitting layer 113, cgDBCzPA is a host material and 1,6mMemFLPAPrn is a light-emitting material.

Next, as the first electron-transport layer 114-b, cgDBCzPA was deposited over the light-emitting layer 113 by evaporation to a thickness of 10 nm. Then, as the second electron-transport layer 114-a, bathophenanthroline (abbre-

TABLE 1

| | First Electrode | Hole-injection Layer | Hole-transport Layer (112) | | | Light-emitting Layer | Electron-transport Layer (114) | | Electron-injection Layer | Second Electrode |
|---|---|---|---|---|---|---|---|---|---|---|
| | (101) | (111) | 112-a | 112-b | 112-c | (113) | 114-a | 114-b | (115) | (102) |
| Thickness (nm) | 70 | 5 | 10 | 10 | 10 | 25 | 10 | 15 | 1 | 200 |
| Light-emitting Element 1 | ITSO | HAT-CN | NPB | * | βNP2PC | cgDBCzPA:1,6mMemFLPAPrn (1:0.03) | cgDBCzPA | Bphen | LiF | Al |
| Light-emitting Element 2 | ITSO | HAT-CN | NPB | ** | βNP2PC | cgDBCzPA:1,6mMemFLPAPrn (1:0.03) | cgDBCzPA | BPhen | LiF | Al |
| Comparative Light-emitting Element 3 | ITSO | HAT-CN | NPB | *** | βNP2PC | cgDBCzPA:1,6mMemFLPAPrn (1:0.03) | cgDBCzPA | BPhen | LiF | Al |

* BnfBB1TP
** BnfBB1BP
*** DBfBB1BP

<Fabrication of Light-Emitting Elements>
<<Fabrication of Light-Emitting Element 1>>

As the electrode 101, an ITSO film was formed to a thickness of 70 nm over a glass substrate by a sputtering method. The electrode area of the electrode 101 was set to 4 mm² (2 mm×2 mm). Next, in pretreatment for forming the light-emitting element over the substrate, a surface of the substrate was washed with water and dried at 200° C. for 1 hour, and then UV ozone treatment was performed for 370 seconds. After that, the substrate was transferred into a vacuum evaporation apparatus where a degree of vacuum was kept at approximately $10^{-4}$ Pa, and baking was performed at 170° C. for 30 minutes. Then, the substrate was cooled down for approximately 30 minutes.

Next, as the hole-injection layer 111, 2,3,6,7,10,11-hexacyano-1,4,5,8,9,12-hexaazatriphenylene (abbreviation: HAT-CN) was deposited over the electrode 101 by evaporation to a thickness of 5 nm.

Next, as the first hole-transport layer 112-a, 4,4'-bis[N-(1-naphthyl)-N-phenylamino]biphenyl (abbreviation: NPB)

viation: BPhen) was deposited over the first electron-transport layer 114-b by evaporation to a thickness of 15 nm.

After that, as the electron-injection layer 115, lithium fluoride (LiF) was deposited over the second electron-transport layer 114-a by evaporation to a thickness of 1 nm.

As the electrode 102, aluminum (Al) was deposited over the electron-injection layer 115 to a thickness of 200 nm.

Next, in a glove box containing a nitrogen atmosphere, a glass substrate over which the light-emitting element 1 was formed was fixed to a substrate (a counter substrate) with a sealant for an organic EL device, whereby the light-emitting element 1 was sealed. Specifically, a drying agent was attached to the counter substrate, the sealant was applied to the counter glass substrate so as to surround the light-emitting element, and the counter glass substrate and the substrate over which the light-emitting element was formed were bonded to each other. Then, irradiation with ultraviolet light having a wavelength of 365 nm at 6 J/cm² and heat treatment at 80° C. for one hour were performed. Through the above steps, the light-emitting element 1 was fabricated.

<<Fabrication of Light-Emitting Element 2>>

A light-emitting element 2 was fabricated through the same steps as those for the light-emitting element 1 except for the step of forming the second hole-transport layer 112-b.

As the second hole-transport layer 112-b of the light-emitting element 2, BnfBB1BP was deposited by evaporation to a thickness of 10 nm.

<<Fabrication of Comparative Light-Emitting Element 3>>

The comparative light-emitting element 3 was fabricated through the same steps as those for the light-emitting element 1 except for the step of forming the second hole-transport layer 112-b.

As the second hole-transport layer 112-b of the comparative light-emitting element 3, DBfBB1TP was deposited by evaporation to a thickness of 10 nm.

<Characteristics of Light-Emitting Elements>

Next, the characteristics of the fabricated light-emitting element 1, light-emitting element 2, and comparative light-emitting element 3 were measured. For measuring the luminance and the CIE chromaticity, a luminance colorimeter (BM-5A manufactured by TOPCON TECHNOHOUSE CORPORATION) was used. For measuring the electroluminescence spectrum, a multi-channel spectrometer (PMA-11 manufactured by Hamamatsu Photonics K.K.) was used.

Figure 24:
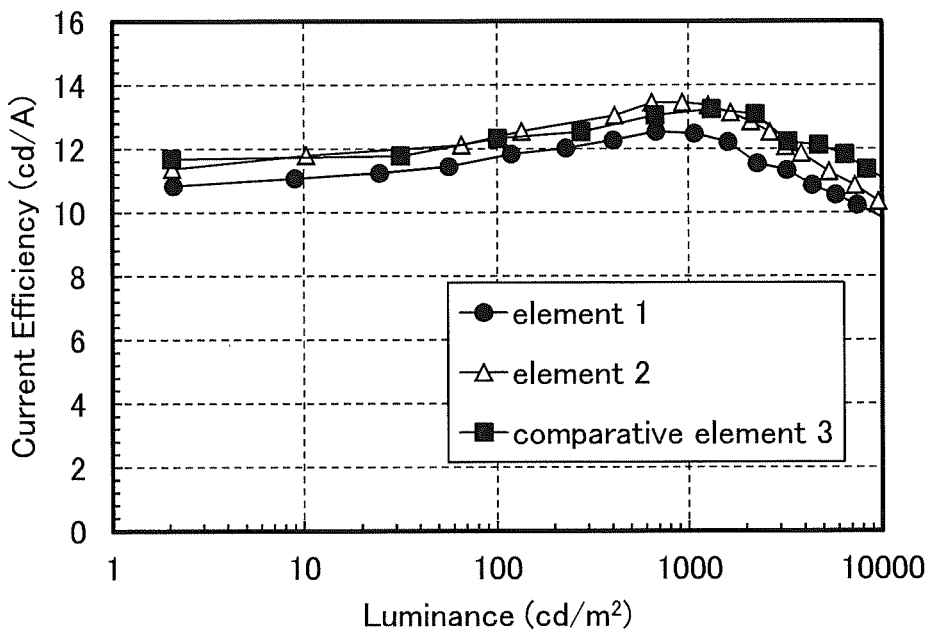
FIG. 24 shows current efficiency-luminance characteristics of light-emitting elements in Example.
Figure 25:
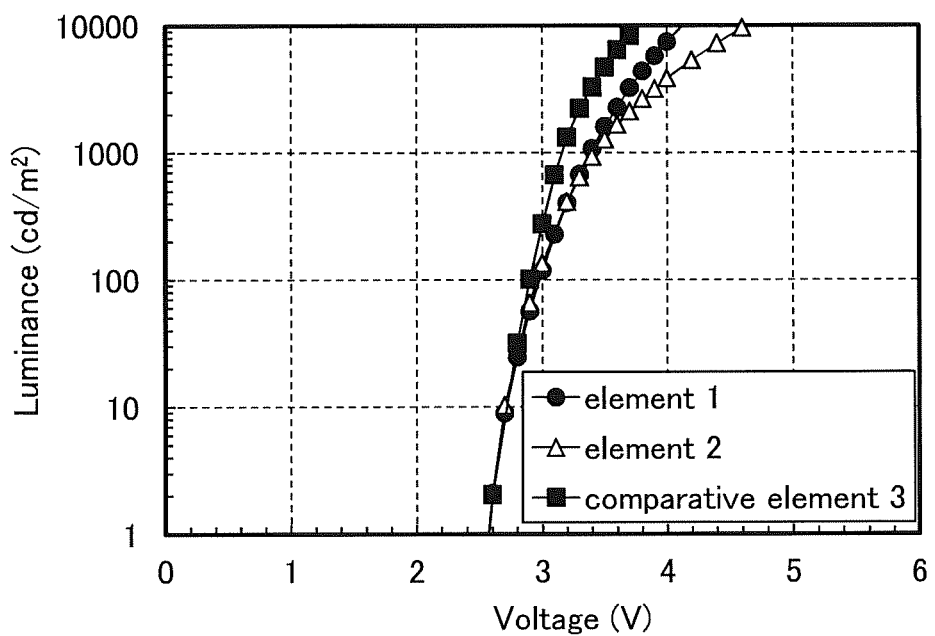
FIG. 25 shows luminance-voltage characteristics of light-emitting elements in Example.
Figure 26:
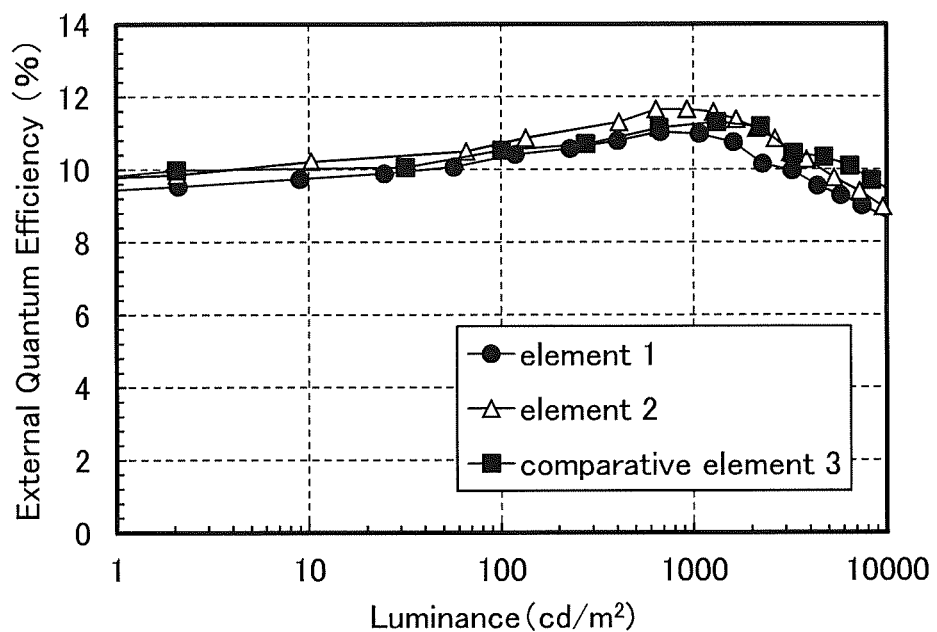
FIG. 26 shows external quantum efficiency-luminance characteristics of light-emitting elements in Example.

FIG. 24 shows current efficiency-luminance characteristics of the light-emitting element 1, the light-emitting element 2, and the comparative light-emitting element 3. FIG. 25 shows luminance-voltage characteristics. FIG. 26 shows external quantum efficiency-luminance characteristics. The measurements of the light-emitting elements were performed at room temperature (in an atmosphere kept at 23° C.).

Table 2 shows the element characteristics of the light-emitting element 1, the light-emitting element 2, and the comparative light-emitting element 3 at around 1000 cd/m$^2$.

retical external quantum efficiency of a fluorescent element is at most 6.25%. The light-emitting element 1, the light-emitting element 2, and the comparative light-emitting element 3 each have external quantum efficiency of higher than or equal to 11%, which exceeds a theoretical limit. This is probably because in the light-emitting element 1, the light-emitting element 2, and the comparative light-emitting element 3, light emission derived from the singlet excitons generated by recombination of carriers injected from the pair of electrodes is obtained, and some of the triplet excitons are converted into singlet excitons by TTA described in Embodiment 3 and contribute to fluorescence. Although not described in this example, transient fluorescence was measured, whereby delayed fluorescence was observed in each of the light-emitting element 1, the light-emitting element 2, and the comparative light-emitting element 3. Accordingly, it was found that external quantum efficiency higher than a theoretical limit was obtained by TTA in each of the light-emitting element 1, the light-emitting element 2, and the comparative light-emitting element 3.

As shown in Table 2, the driving voltage of each of the light-emitting element 1, the light-emitting element 2, and the comparative light-emitting element 3 is lower than or equal to 3.5 V at around 1000 cd/m$^2$, which exhibits high power efficiency.

Figure 27:
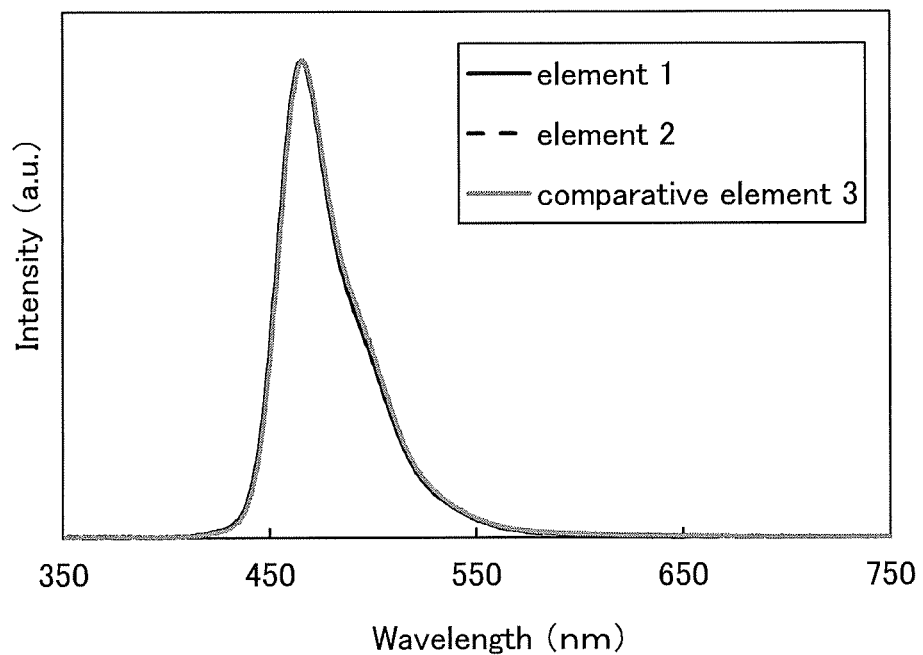
FIG. 27 shows electroluminescence spectra of light-emitting elements in Example.

As shown in FIG. 27, the electroluminescence spectrum of each of the light-emitting element 1, the light-emitting element 2, and the comparative light-emitting element 3 has a peak at around 465 nm and a full width at half maximum of approximately 40 nm; thus, the light-emitting element 1, the light-emitting element 2, and the comparative light-emitting element 3 emit blue light with high color purity.

<Reliability of Light-Emitting Elements>

Next, driving tests at a constant current of 2 mA were performed on the light-emitting element 1, the light-emitting

TABLE 2

| | Voltage (V) | Current Density (mA/cm$^2$) | CIE Chromaticity (x, y) | Luminance (cd/m$^2$) | Current Efficiency (cd/A) | Power Efficiency (lm/W) | External Quantum Efficiency (%) |
|---|---|---|---|---|---|---|---|
| Light-emitting Element 1 | 3.40 | 8.62 | (0.139, 0.159) | 1080 | 12.5 | 11.5 | 11.0 |
| Light-emitting Element 2 | 3.40 | 6.92 | (0.138, 0.160) | 930 | 13.5 | 12.4 | 11.7 |
| Comparative Light-emitting Element 3 | 3.20 | 9.97 | (0.139, 0.165) | 1320 | 13.2 | 13.0 | 11.3 |

FIG. 27 shows electroluminescence spectra of the light-emitting element 1, the light-emitting element 2, and the comparative light-emitting element 3 to which a current at a current density of 12.5 mA/cm$^2$ was supplied.

As shown in FIG. 24, FIG. 26, and Table 2, the light-emitting element 1, the light-emitting element 2, and the comparative light-emitting element 3 each have high current efficiency and high external quantum efficiency. The maximum external quantum efficiency of each of the light-emitting element 1, the light-emitting element 2, and the comparative light-emitting element 3 is higher than or equal to 11%, which is an excellent value for a fluorescent element.

Figure 28:
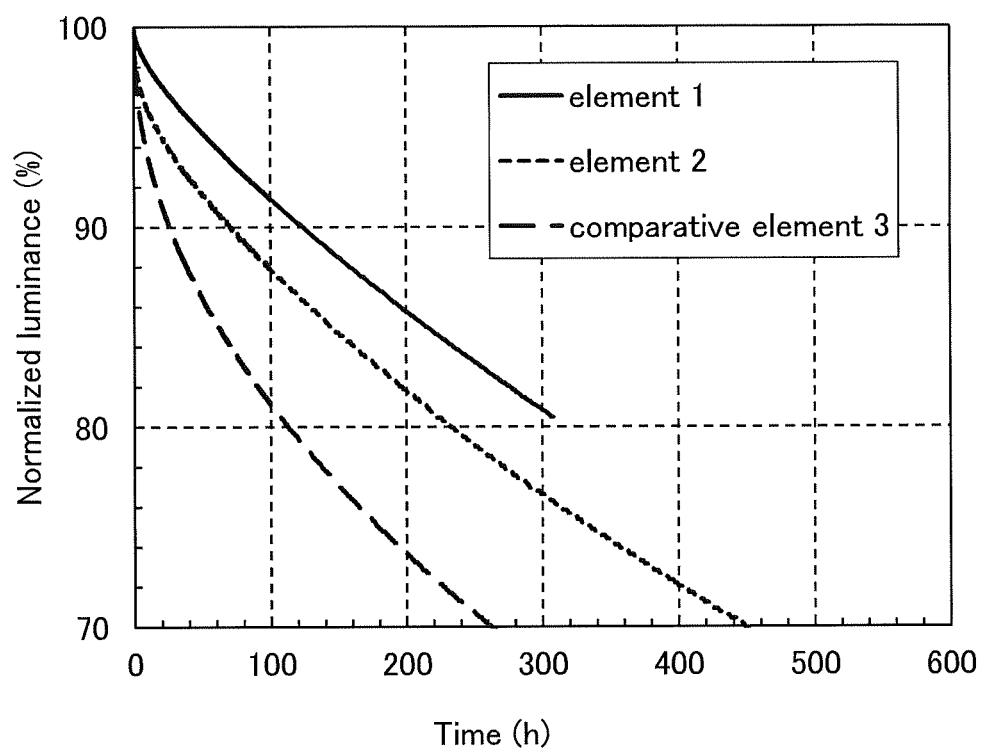
FIG. 28 shows reliability test results of light-emitting elements in Example.

Since the probability of formation of singlet excitons which are generated by recombination of carriers (holes and electrons) injected from a pair of electrodes is 25%, when the light extraction efficiency to the outside is 25%, theoelement 2, and the comparative light-emitting element 3. FIG. 28 shows the results. As shown in FIG. 28, LT$_{70}$ (time for which luminance is reduced by 30%) of each of the light-emitting element 1, the light-emitting element 2, and the comparative light-emitting element 3 is longer than 250 hours, which means that the light-emitting elements have high reliability. In addition, as shown in FIG. 28, the light-emitting elements 1 and 2 have higher reliability than the comparative light-emitting element 3. Accordingly, it was found that a benzo[b]naphtho[1,2-d]furan skeleton is preferred to a dibenzofuran skeleton in order to achieve high reliability.

Example 5

In this example, a method for synthesizing N,N-bis[4-(benzo[b]naphtho[1,2-d]furan-6-yl)phenyl]-4-amino-p-terphenyl (abbreviation: Bnf(6)BB1TP), which is the organic compound of one embodiment of the present invention represented by Structural Formula (106), and the physical properties of the compound are described.

Synthesis Example 4

Step 1: Synthesis of N,N-bis[4-(4,4,5,5-tetramethyl-1,3,2-dioxaborolan-2-yl)phenyl]-4-amino-p-terphenyl Into a 200-mL three-neck flask were put 1.7 g (3.0 mmol) of N,N-bis(4-bromophenyl)-4-amino-p-terphenyl, 1.4 g (3.0 mmol) of bis(pinacolato)diboron, 0.10 g (0.20 mmol) of 2-di-tert-butylphosphino-2',4',6'-triisopropylbiphenyl (abbreviation: tBuXphos), and 1.3 g (12 mmol) of potassium acetate. Then, the air in the system was replaced with nitrogen. After 30 mL of xylene was added to this mixture, the resulting mixture was degassed under reduced pressure and then, a nitrogen gas was made to flow continuously in the system. After this mixture was heated to 60° C., 88 mg (0.10 mmol) of [1,1'-bis(diphenylphosphino)ferrocene]palladium(II) dichloride was added and stirring was performed at 120° C. for 7.5 hours. Disappearance of the source material was checked with thin layer chromatography, and then, the next reaction was performed. Synthesis Scheme of Step 1 is shown in (D-1) below.

Step 2: Synthesis of Bnf(6)BB1TP

To the mixture obtained in Step 1, 2.1 g (6.0 mmol) of 6-iodobenzo[b]naphtho[1,2-d]furan, 85 mg (0.20 mmol) of tBuXphos, and 4.1 g (12 mmol) of cesium carbonate were added. The mixture was degassed under reduced pressure and then, a nitrogen gas was made to flow continuously in the system. After this mixture was heated to 60° C., 86 mg (0.10 mmol) of [1,1'-bis(diphenylphosphino)ferrocene]palladium(II) dichloride was added and this mixture was stirred at 120° C. for 15 hours. After the stirring, the obtained mixture was washed with water and saturated saline, and dried with magnesium sulfate. The resulting mixture was gravity-filtered and the filtrate was concentrated to give a solid. The obtained solid was purified by high performance liquid chromatography (HPLC) to give 1.0 g of a target pale yellow solid in a yield of 60%. Synthesis Scheme of Step 2 is shown in (D-2) below.

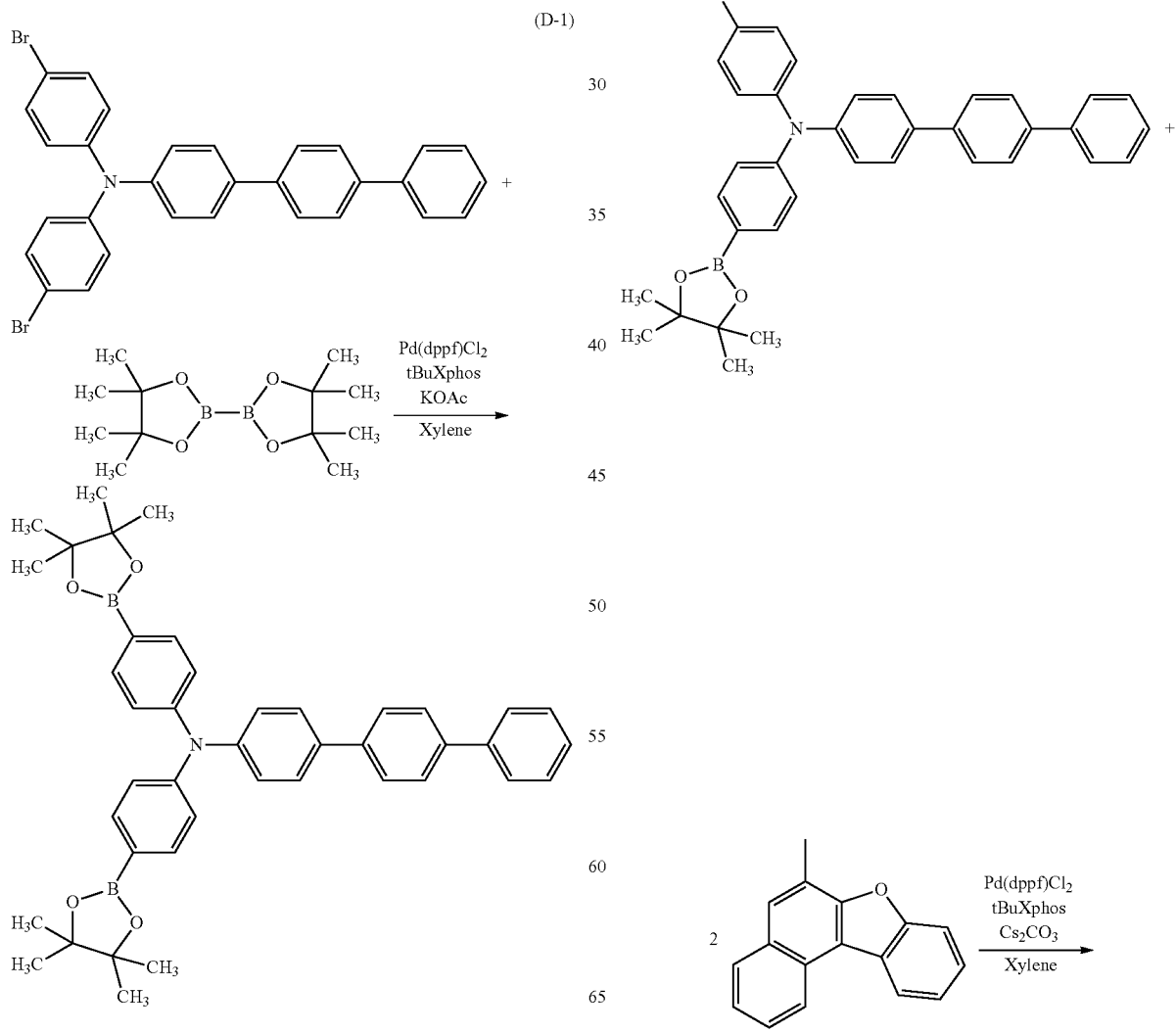

-continued

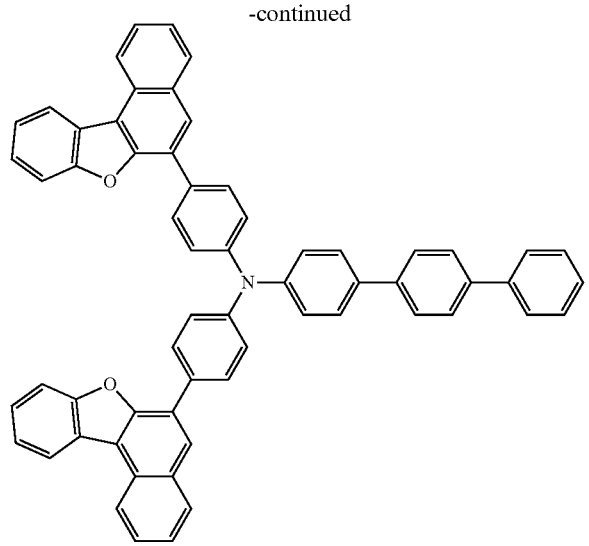

(106)

By a train sublimation method, 0.89 g of the obtained solid was purified. In the sublimation purification, the solid was heated at 410° C. for 15 hours under a pressure of 3.1 Pa with a flow rate of argon of 15 mL/min. After the sublimation purification, 0.59 g of a target pale brown solid was obtained at a collection rate of 67%.

The obtained solid was subjected to nuclear magnetic resonance spectrometry ($^1$H NMR), and the results are shown below.

$^1$H NMR (chloroform-d, 500 MHz): δ=7.35-7.60 (m, 14H), 7.65-7.77 (m, 12H), 7.84 (d, J=8.5 Hz, 1H), 7.95-8.09 (m, 8H), 8.39 (d, J=8.5 Hz, 1H), 8.46-8.50 (m, 1H), 8.68 (t, J=8.5 Hz, 2H).

Figure 29A:
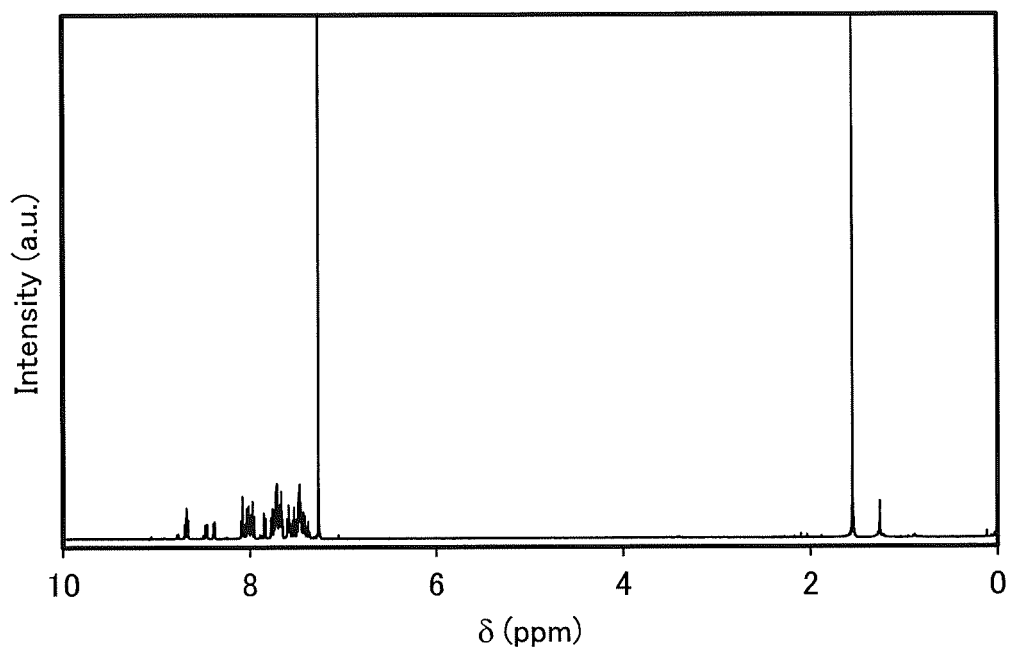
FIGS. 29A and 29B show NMR charts of a compound in Example.
Figure 29B:
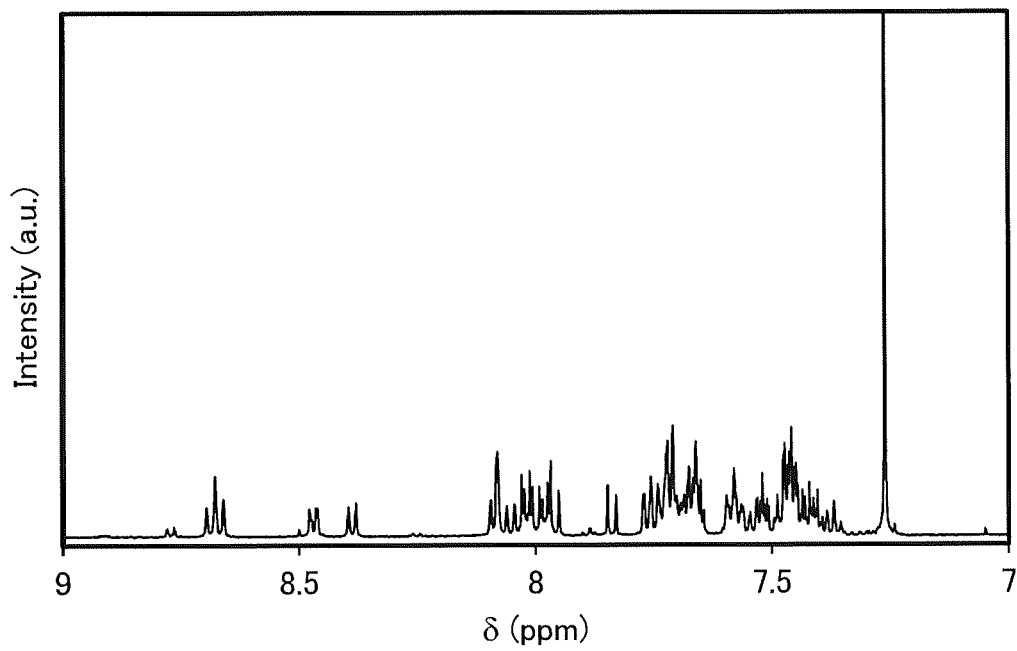

FIGS. 29A and 29B are $^1$H NMR charts of the obtained solid. Note that FIG. 29B is a chart showing an enlarged part in the range of 7.0 ppm to 9.0 ppm of FIG. 29A. The results revealed that Bnf(6)BB1TP, which was the target substance, was obtained.

The MS spectrum of the obtained solid was measured by a laser desorption ionization (LDI-TOFMS) method. The LDI-TOFMS measurement was performed using an ultra-high resolution MALDI-TOFMS system manufactured by JEOL Ltd. The measurement was performed in a positive ion spiral mode, and Bnf(6)BB1TP in chloroform at a given concentration was dropped on a target plate. Laser power was set to 40 and integration was performed more than or equal to 200 times; as a result, nm/z 829.3, which indicated that Bnf(6)BB1TP (the target substance) was obtained, was observed.

<Properties of Bnf(6)BB1TP>

Figure 30:
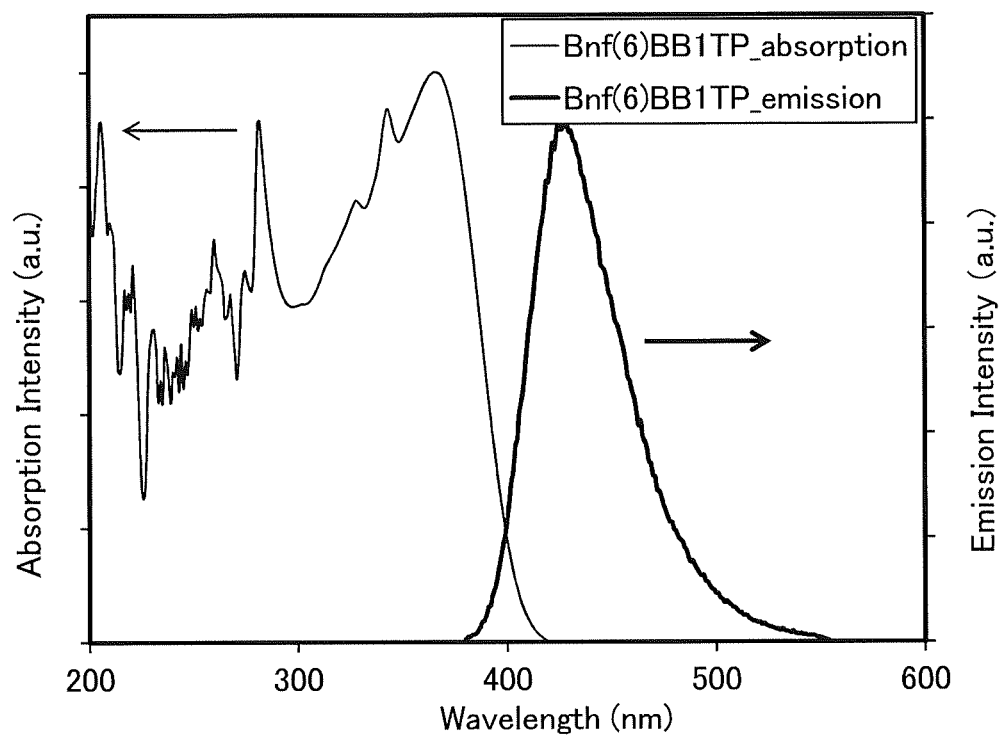
FIG. 30 shows absorption and emission spectra of a compound in Example.
Figure 31:
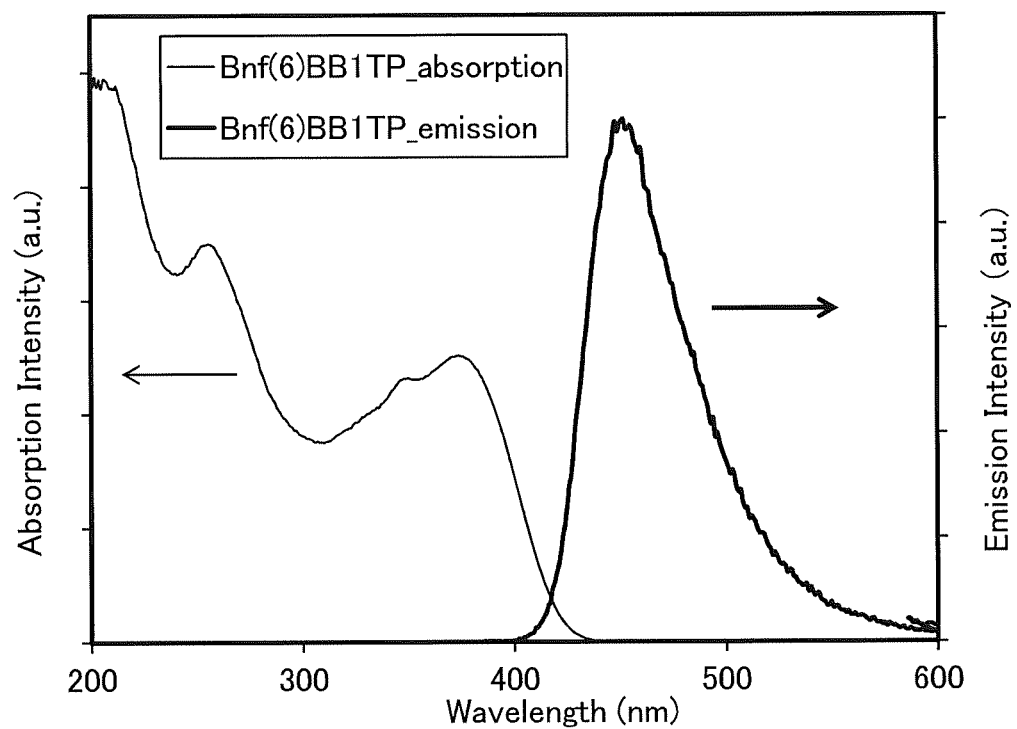
FIG. 31 shows absorption and emission spectra of a compound in Example.

Next, FIG. 30 shows an absorption spectrum and an emission spectrum of Bnf(6)BB1TP in a toluene solution. FIG. 31 shows an absorption spectrum and an emission spectrum of a thin film of Bnf(6)BB1TP. The measurement was performed in a manner similar to that described in Example 1.

As shown in FIG. 30, Bnf(6)BB1TP in the toluene solution has an absorption peak at around 367 nm, and an emission wavelength peak at 424 nm (excitation wavelength: 366 nm). As shown in FIG. 31, the thin film of Bnf(6)BB1TP has absorption peaks at around 374 nm, 350 nm, and 256 nm, and an emission wavelength peak at around 451 nm (excitation wavelength: 380 nm). It was found that Bnf(6)BB1TP emitted blue light. The compound of one embodiment of the present invention can be used as a host material for a light-emitting substance or a host material for a substance emitting fluorescence in the visible region.

It was found that aggregation of the thin film of Bnf(6) BB1TP is not easily caused even under the air and the thin film suffers only a small change in shape and has high film quality.

Next, the HOMO level and the LUMO level of Bnf(6) BB1TP were obtained through a cyclic voltammetry (CV) measurement. A calculation method is similar to that described in Example 1.

Furthermore, the CV measurement was repeated 100 times, and the oxidation-reduction wave at the hundredth cycle and the oxidation-reduction wave at the first cycle were compared with each other to examine the electric stability of the compound.

As a result, in the measurement of an oxidation potential Ea [V] of Bnf(6)BB1TP, the HOMO level was −5.50 eV. In contrast, the LUMO level was −2.51 eV. When the oxidation-reduction wave was repeatedly measured, in the Ea measurement, the peak intensity of the oxidation-reduction wave after the hundredth cycle was maintained to be 88% of that of the oxidation-reduction wave at the first cycle, and in the Ec measurement, the peak intensity of the oxidation-reduction wave after the hundredth cycle was maintained to be 99% of that of the oxidation-reduction wave at the first cycle; thus, resistance to oxidation and reduction of Bnf(6) BB1TP was found to be extremely high.

Furthermore, differential scanning calorimetry (DSC measurement) of Bnf(6)BB1TP was performed. The measurement was performed in a manner similar to that described in Example 1. It was found from the DSC measurement result of the second cycle that the glass transition point of Bnf(6)BB1TP is 163° C., that is, Bnf(6)BB1TP has extremely high heat resistance.

The thermogravimetry-differential thermal analysis (TG-DTA) was performed on Bnf(6)BB1TP. The measurement was performed in a manner similar to that described in Example 1. In the thermogravimetry-differential thermal analysis, the temperature (decomposition temperature) at which the weight obtained by thermogravimetry was reduced by 5% of the weight at the beginning of the measurement was found to be 500° C. or higher, which shows that Bnf(6)BB1TP is a substance with high heat resistance.

Example 6

In this example, a method for synthesizing N,N'-bis[4-(benzo[b]naphtho[1,2-d]furan-8-yl)phenyl]-4-amino-p-terphenyl (abbreviation: Bnf(8)BB1TP), which is the organic compound of one embodiment of the present invention represented by Structural Formula (117), and the physical property of the compound are described.

Synthesis Example 5

Step 1: Synthesis of N,N'-bis[4-(4,4,5,5-tetramethyl-1,3,2-dioxaborolan-2-yl)phenyl]-4-amino-p-terphenyl Into a 200-mL three-neck flask were put 0.56 g (1.0 mmol) of N,N'-bis(4-bromophenyl)-4-amino-p-terphenyl, 0.52 g (2.0 mmol) of bis(pinacolato)diboron, 0.85 g (0.20 mmol) of 2-di-tert-butylphosphino-2',4',6'-triisopropylbiphenyl (abbreviation: tBuXphos), and 0.39 g (4.0 mmol) of potassium acetate. Then, the air in the system was replaced with nitrogen. After 10 mL of xylene was added to this mixture, the resulting mixture was degassed under reduced pressure and then, a nitrogen gas was made to flow continuously in the system. After this mixture was heated to 60° C., 87 mg (0.10 mmol) of [1,1'-bis(diphenylphosphino)ferrocene]palladium(II) dichloride was added and stirring was performed at 120° C. for 6 hours. Disappearance of the source material was checked with thin layer chromatography, and then, the next reaction was performed. Synthesis Scheme of Step 1 is shown in (E-1) below.

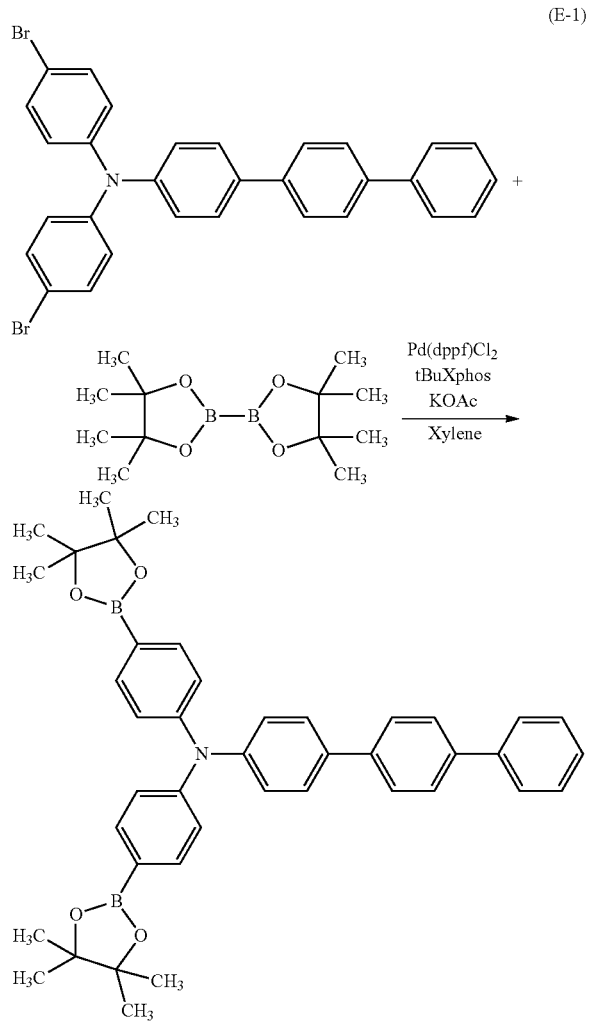

Step 2: Synthesis of Bnf(8)BB1TP

To the mixture obtained in Step 1, 0.51 g (2.0 mmol) of 8-chlorobenzo[b]naphtho[1,2-d]furan, 83 mg (0.20 mmol) of tBuXphos, and 1.4 g (4.0 mmol) of cesium carbonate were added. The mixture was degassed under reduced pressure and then, a nitrogen gas was made to flow continuously in the system. After this mixture was heated to 60° C., 82 mg (0.10 mmol) of [1,1'-bis(diphenylphosphino)ferrocene]palladium(II) dichloride was added and this mixture was stirred at 120° C. for 15 hours. After the stirring, the obtained mixture was filtered through Celite (Catalog No. 537-02305, produced by Wako Pure Chemical Industries, Ltd.), Florisil (Catalog No. 066-05265, produced by Wako Pure Chemical Industries, Ltd.), and alumina. The obtained filtrate was concentrated to give a target pale yellow solid. Synthesis Scheme of Step 2 is shown in (E-2) below.

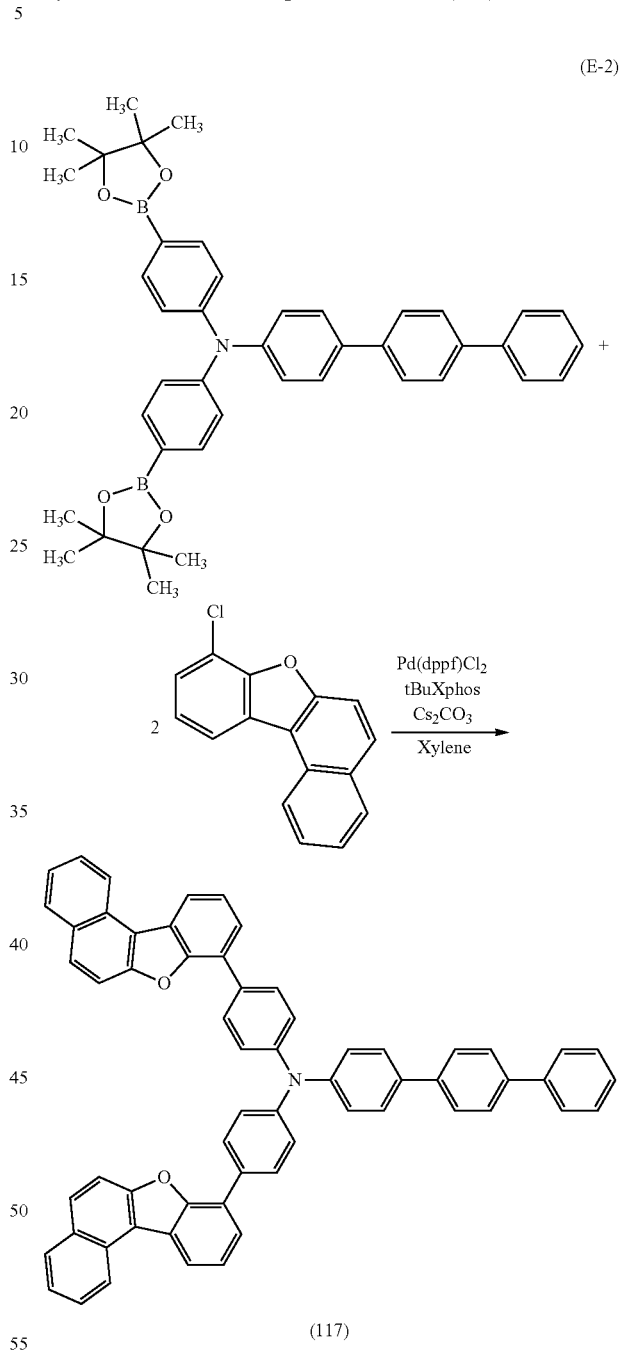

The MS spectrum of the obtained solid was measured by LDI-TOFMS. The measurement was performed in a manner similar to that described in Example 5. As a result of the measurement, m/z 829.3, which indicated that Bnf(8)BB1TP (the target substance) was obtained, was observed.

Example 7

In this example, light-emitting elements each including Bnf(6)BB1TP, which is the organic compound of one embodiment of the present invention, in the hole-transport layer 112-*b* are described. The structures of the light-emitting elements fabricated in this example are similar to those of the light-emitting elements described in Example 4; thus, the description of the fabrication method is omitted. A cross-sectional view of the structure of each of the light-emitting elements fabricated in this example is similar to that in FIG. 1B. Table 3 shows details of the element structures. In addition, structures and abbreviations of compounds used here are shown below. Note that Examples described above can be referred to for other compounds.

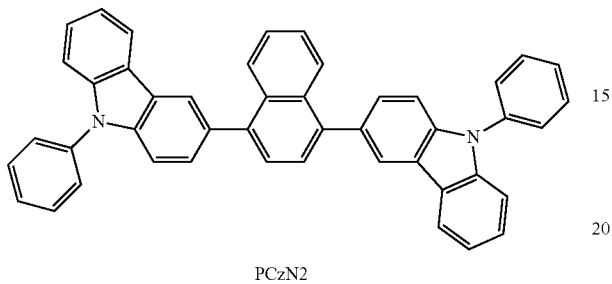

PCzN2

TABLE 3

| | First Electrode | Hole-injection Layer | Hole-transport Layer (112) | | | Light-emitting Layer | Electron-transport Layer (114) | | Electron-injection Layer | Second Electrode |
|---|---|---|---|---|---|---|---|---|---|---|
| | (101) | (111) | 112-a | 112-b | 112-c | (113) | 114-a | 114-b | (115) | (102) |
| Thickness (nm) | 70 | 5 | 10 | 10 | 10 | 25 | 15 | 10 | 1 | 200 |
| Light-emitting Element 4 | ITSO | HAT-CN | NPB | * | PCzN2 | cgDBCzPA:1,6mMemFLPAPrn (1:0.03) | cgDBCzPA | NBPhen | LiF | Al |
| Comparative Light-emitting Element 5 | ITSO | HAT-CN | NPB | ** | PCzN2 | cgDBCzPA:1,6mMemFLPAPrn (1:0.03) | cgDBCzPA | NBPhen | LiF | Al |

<Hole-Transport Layer 112-*c* of Light-Emitting Element>

As the hole-transport layer 112-*c*, 3,3'-(naphthalen-1,4-diyl)bis(9-phenyl-9H-carbazole) (abbreviation: PCzN2) was deposited over the hole-transport layer 112-*b* of each of a light-emitting element 4 and a comparative light-emitting element 5 by evaporation to a thickness of 10 nm.

<Characteristics of Light-Emitting Elements>

Next, the characteristics of the fabricated light-emitting element 4 and comparative light-emitting element 5 were measured. The measurement was performed in a manner similar to that described in Example 4.

Figure 32:
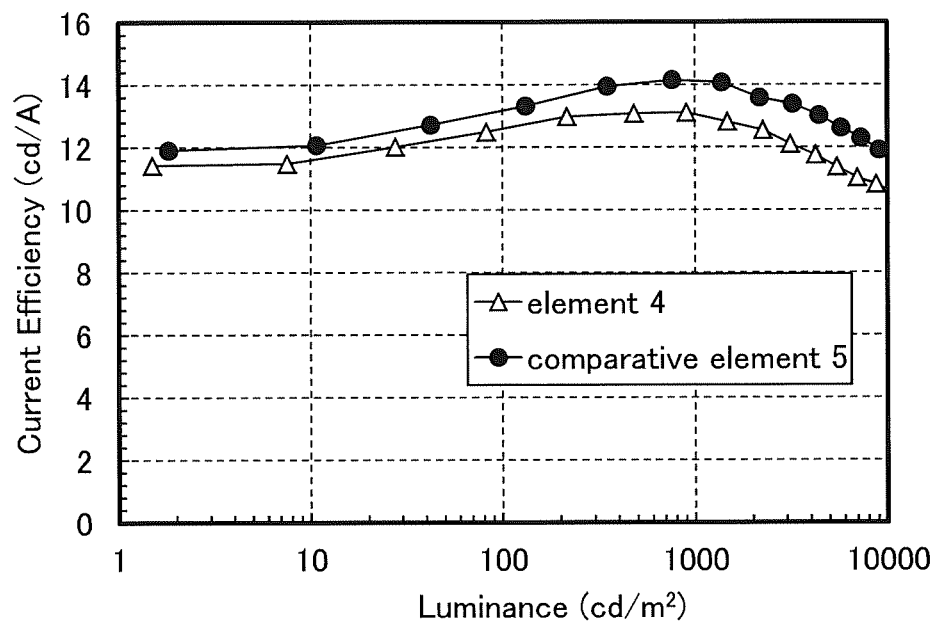
FIG. 32 shows current efficiency-luminance characteristics of light-emitting elements in Example.
Figure 33:
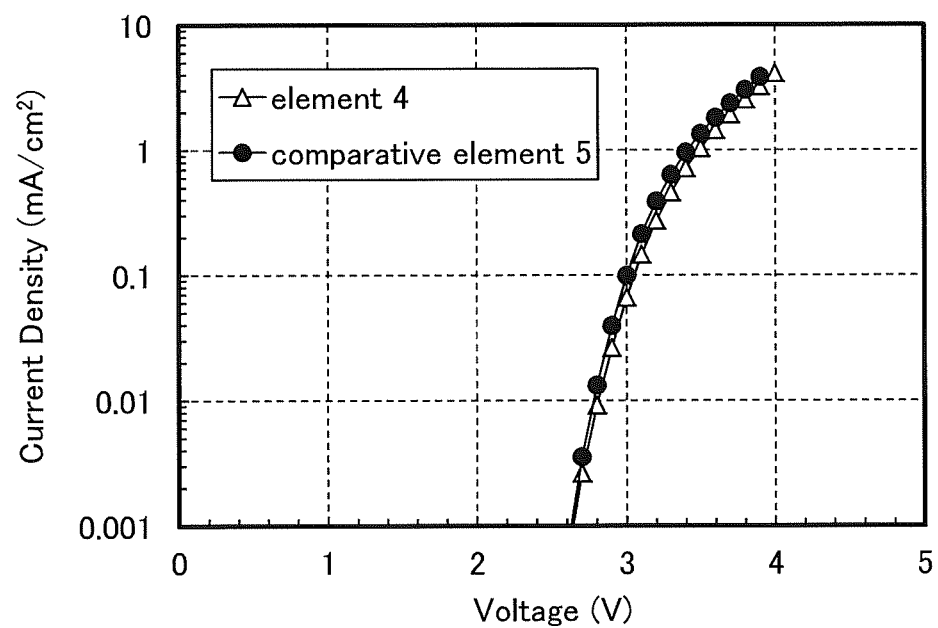
FIG. 33 shows current density-voltage characteristics of light-emitting elements in Example.
Figure 34:
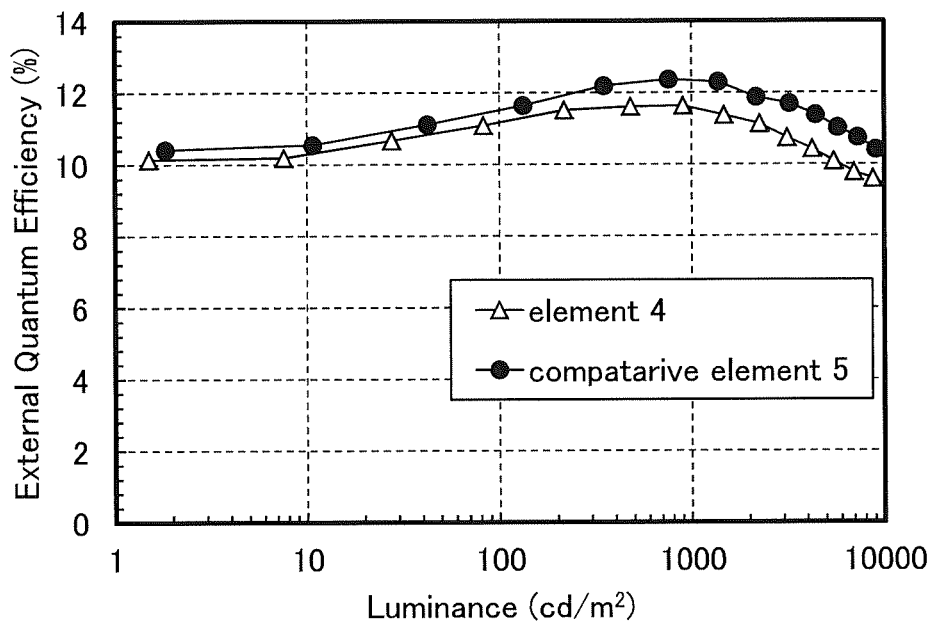
FIG. 34 shows external quantum efficiency-luminance characteristics of light-emitting elements in Example.

FIG. 32 shows current efficiency-luminance characteristics of the light-emitting element 4 and the comparative light-emitting element 5. FIG. 33 shows current density-voltage characteristics. FIG. 34 shows external quantum efficiency-luminance characteristics.

Table 4 shows the element characteristics of the light-emitting element 4 and the comparative light-emitting element 5 at around 1000 cd/m$^2$.

TABLE 4

| | Voltage (V) | Current Density (mA/cm$^2$) | CIE Chromaticity (x, y) | Luminance (cd/m$^2$) | Current Efficiency (cd/A) | Power Efficiency (lm/W) | External Quantum Efficiency (%) |
|---|---|---|---|---|---|---|---|
| Light-emitting Element 4 | 3.20 | 6.87 | (0.141, 0.154) | 901 | 14.2 | 12.9 | 11.6 |

TABLE 4-continued

| | Voltage (V) | Current Density (mA/cm$^2$) | CIE Chromaticity (x, y) | Luminance (cd/m$^2$) | Current Efficiency (cd/A) | Power Efficiency (lm/W) | External Quantum Efficiency (%) |
|---|---|---|---|---|---|---|---|
| Comparative Light-emitting Element 5 | 3.10 | 5.36 | (0.140, 0.160) | 758 | 13.1 | 14.3 | 12.4 |

Figure 35:
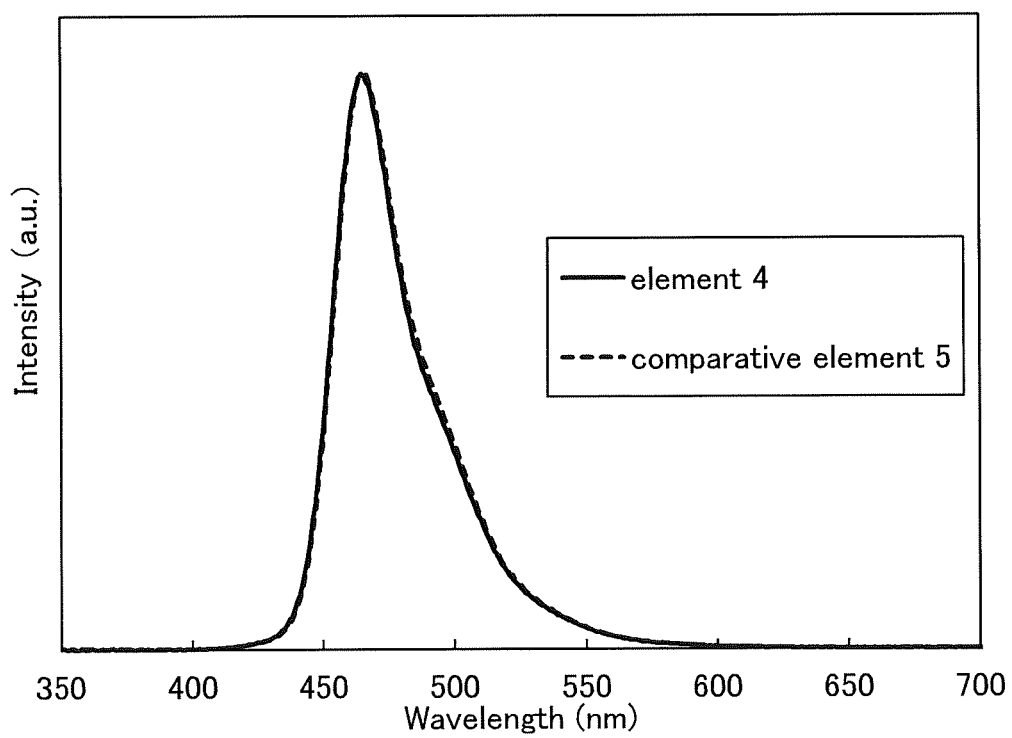
FIG. 35 shows electroluminescence spectra of light-emitting elements in Example.

FIG. 35 shows electroluminescence spectra of the light-emitting element 4 and the comparative light-emitting element 5 to which a current at a current density of 12.5 mA/cm$^2$ was supplied.

As shown in FIG. 32, FIG. 34, and Table 4, the light-emitting element 4 and the comparative light-emitting element 5 each have high current efficiency and high external quantum efficiency. The maximum external quantum efficiency of each of the light-emitting element 4 and the comparative light-emitting element 5 is higher than or equal to 11%, which is an excellent value for a fluorescent element. As in the light-emitting elements described in Example 4, external quantum efficiency higher than a theoretical limit was obtained by TTA in each of the light-emitting element 4 and the comparative light-emitting element 5.

As shown in Table 4, the driving voltage of each of the light-emitting element 4 and the comparative light-emitting element 5 is lower than or equal to 3.2 V at around 1000 cd/m$^2$, which exhibits high power efficiency.

As shown in FIG. 35, the electroluminescence spectrum of each of the light-emitting element 4 and the comparative light-emitting element 5 has a peak at around 465 nm and a full width at half maximum of approximately 35 nm; thus, the light-emitting element 4 and the comparative light-emitting element 5 emit blue light with high color purity.

<Reliability of Light-Emitting Elements>

Figure 36:
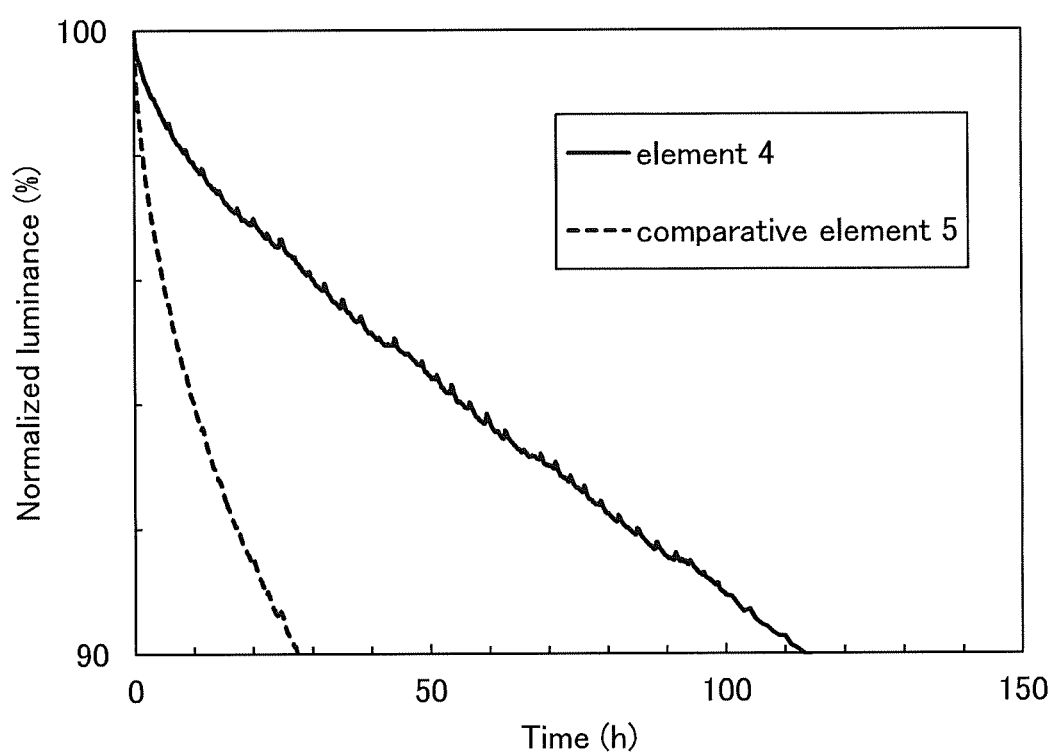
FIG. 36 shows reliability test results of light-emitting elements in Example.

Next, driving tests at a constant current of 2 mA were performed on the light-emitting element 4 and the comparative light-emitting element 5. FIG. 36 shows the results. As shown in FIG. 36, LT$_{90}$ (time for which luminance is reduced by 10%) of the light-emitting element 4 is longer than 100 hours, which means that the light-emitting element has high reliability. In addition, as shown in FIG. 36, the light-emitting element 4 has higher reliability than the comparative light-emitting element 5. Accordingly, it was found that a benzo[b]naphtho[1,2-d]furan skeleton is preferred to a dibenzofuran skeleton in order to achieve high reliability.

REFERENCE NUMERALS

50: adhesive layer, 51: adhesive layer, 52: adhesive layer, 100: light-emitting element, 101: electrode, 102: electrode, 103: EL layer, 110: light-emitting element, 111: hole-injection layer, 112: hole-transport layer, 112-a: hole-transport layer, 112-b: hole-transport layer, 112-c: hole-transport layer, 113: light-emitting layer, 114: electron-transport layer, 114-a: electron-transport layer, 114-b: electron-transport layer, 115: electron-injection layer, 120: light-emitting element, 121: host material, 122: guest material, 131: hole-injection material, 132: hole-transport material, 133: hole-transport material, 134: hole-transport material, 135: host material, 136: guest material, 150: light-emitting element, 201: resin layer, 202: resin layer, 300: display device, 311: electrode, 311b: electrode, 340: liquid crystal element, 351: substrate, 360: light-emitting element, 360b: light-emitting element, 360g: light-emitting element, 360r: light-emitting element, 360w: light-emitting element, 361: substrate, 362: display portion, 364: circuit portion, 365: wiring, 366: circuit portion, 367: wiring, 372: FPC, 373: IC, 374: FPC, 375: IC, 400: display device, 401: transistor, 402: transistor, 403: transistor, 405: capacitor, 406: connection portion, 410: pixel, 411: insulating layer, 412: insulating layer, 413: insulating layer, 414: insulating layer, 415: insulating layer, 416: spacer, 417: adhesive layer, 419: connection layer, 421: electrode, 422: EL layer, 423: electrode, 424: optical adjustment layer, 425: coloring layer, 426: light-blocking layer, 451: opening, 476: insulating layer, 478: insulating layer, 501: transistor, 502: electrode, 503: transistor, 505: capacitor, 506: connection portion, 510: electrode, 511: insulating layer, 512: insulating layer, 513: insulating layer, 514: insulating layer, 517: adhesive layer, 519: connection layer, 521: light-emitting unit, 522: light-emitting unit, 523: charge-generation layer, 529: liquid crystal element, 543: connector, 562: electrode, 563: liquid crystal, 564a: alignment film, 564b: alignment film, 576: insulating layer, 578: insulating layer, 599: polarizing plate, 601: source side driver circuit, 602: pixel portion, 603: gate side driver circuit, 604: sealing substrate, 605: sealant, 607: space, 608: wiring, 610: element substrate, 611: switching TFT, 612: current controlling TFT, 613: electrode, 614: insulator, 616: EL layer, 617: electrode, 618: light-emitting element, 623: n-channel TFT, 624: p-channel TFT, 700: display panel, 701: resin layer, 702: resin layer, 800: display panel, 901: housing, 902: liquid crystal layer, 903: backlight, 904: housing, 905: driver IC, 906: terminal, 1001: substrate, 1002: base insulating film, 1003: gate insulating film, 1006: gate electrode, 1007: gate electrode, 1008: gate electrode, 1020: interlayer insulating film, 1021: interlayer insulating film, 1022: electrode, 1025B: lower electrode, 1024B: electrode, 1025G: lower electrode, 1024G: electrode, 1025R: lower electrode, 1024R: electrode, 1026: partition, 1028: EL layer, 1029: electrode, 1031: sealing substrate, 1032: sealant, 1033: base material, 1034B: coloring layer, 1034G: coloring layer, 1034R: coloring layer, 1035: black layer (black matrix), 1036: overcoat layer, 1037: interlayer insulating film, 1040: pixel portion, 1041: driver circuit portion, 1042: peripheral portion, 2001: housing, 2002: light source, 3001: lighting device, 3002: display device, 5000: display region, 5001: display region, 5002: display region, 5003: display region, 5004: display region, 5005: display region, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7301: housing, 7302: housing, 7303: joint portion, 7304: display portion, 7305: display portion, 7306: speaker portion, 7307: recording medium insertion portion, 7308: LED lamp, 7309: operation key, 7310: connection terminal, 7311: sensor, 7312: microphone, 7401: housing, 7402: display portion, 7403: operation button, 7404: external connection port, 7405: speaker, and 7406: microphone.

This application is based on Japanese Patent Application Serial No. 2016-179489 filed with Japan Patent Office on Sep. 14, 2016, the entire contents of which are hereby incorporated by reference.

The invention claimed is:

1. An organic compound represented by General Formula (G0):

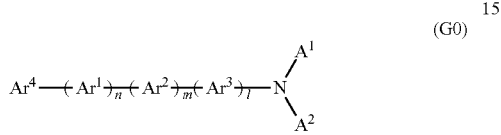

(G0)

wherein Ar$^1$, Ar$^2$, and Ar$^3$ independently represent a substituted or unsubstituted aromatic hydrocarbon group having 6 to 25 carbon atoms, wherein Ar$^4$ represents a substituted or unsubstituted aromatic hydrocarbon group having 6 to 25 carbon atoms, wherein n, m, and l independently represent an integer of 0 or 1, wherein A$^1$ represents General Formula (g0) or General Formula (g1), wherein A$^2$ represents General Formula (g0) or General Formula (g1),

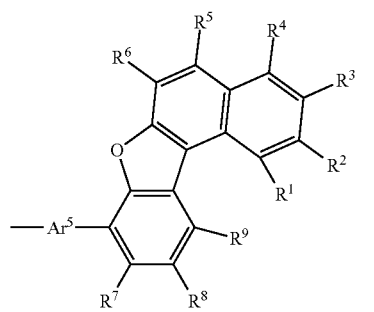

(g0)

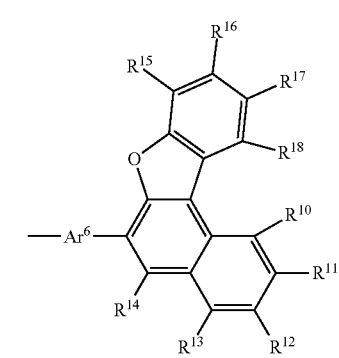

(g1)

wherein Ar$^5$ and Ar$^6$ independently represent a substituted or unsubstituted aromatic hydrocarbon group having 6 to 13 carbon atoms, wherein R$^1$ to R$^{18}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 25 carbon atoms, and wherein R$^6$ and R$^{15}$ independently represent a substituted or unsubstituted aromatic hydrocarbon group having 6 to 13 carbon atoms.

2. The organic compound according to claim 1,
wherein R$^1$ to R$^{18}$ independently represent hydrogen or a substituted or unsubstituted aromatic hydrocarbon group having 6 to 13 carbon atoms.

3. The organic compound according to claim 1,
wherein A$^1$ represents General Formula (g0-a) or General Formula (g1-a),
wherein A$^2$ represents General Formula (g0-a) or General Formula (g1-a),

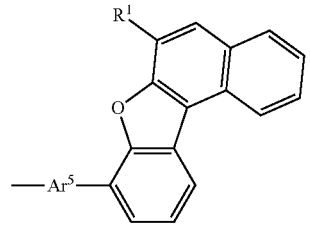

(g0-a)

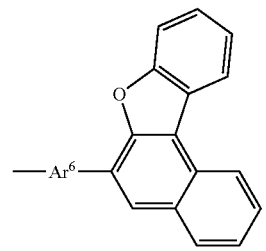

(g1-a)

wherein Ar$^5$ and Ar$^6$ independently represent a substituted or unsubstituted aromatic hydrocarbon group having 6 to 25 carbon atoms, and wherein R$^1$ represents hydrogen or a substituted or unsubstituted phenyl group.

4. The organic compound according to claim 1,
wherein General Formula (G0) are represented by any one of Structural Formulae (102), (103), (106), and (117)

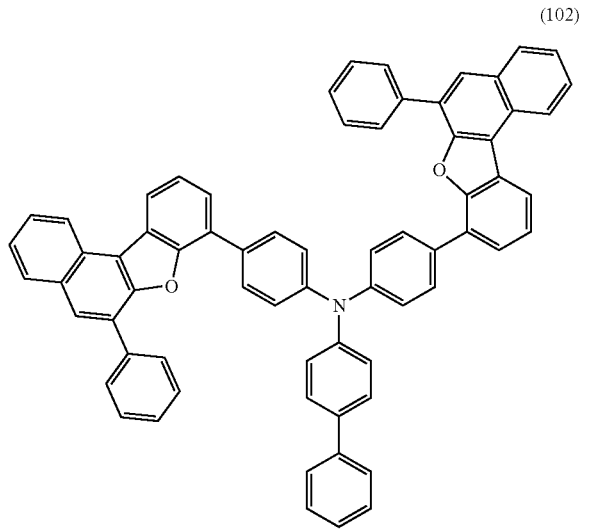

(102)

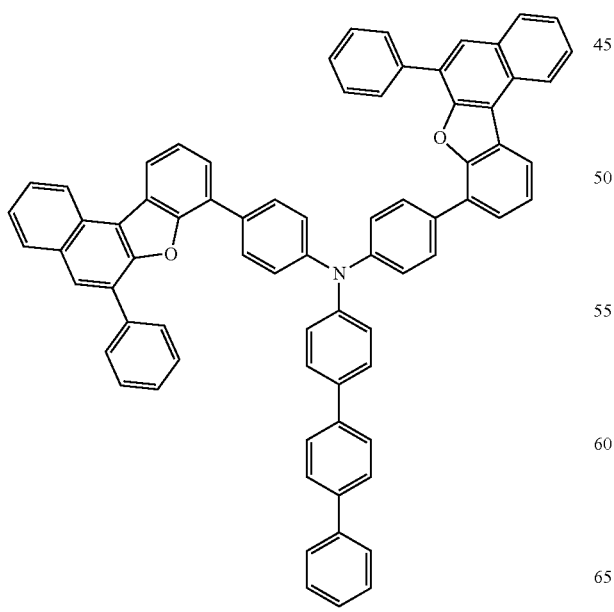

(103)

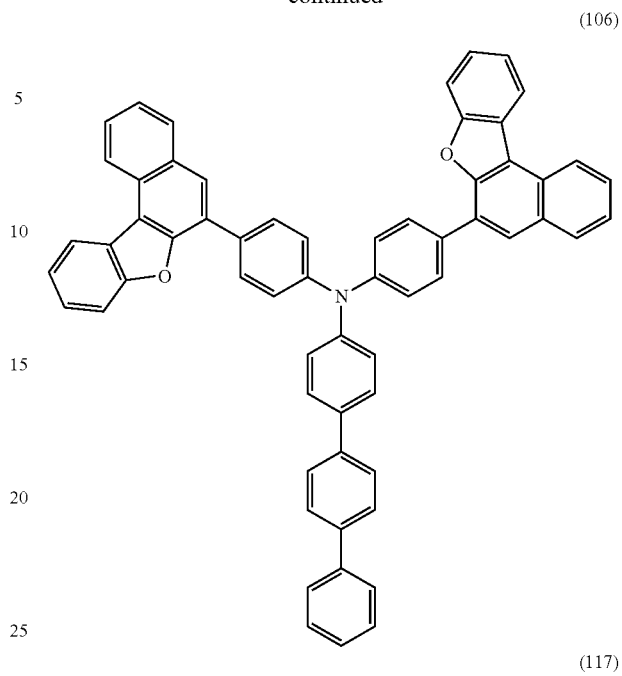

(106)

(117)

5. A light-emitting element comprising:
an anode;
a cathode; and
an electroluminescent layer,
wherein the electroluminescent layer is between the anode and the cathode, and
wherein the electroluminescent layer comprises the organic compound according to claim 1.

6. A light-emitting device comprising:
a light-emitting portion comprising the light-emitting element according to claim 5; and
a substrate.

7. An electronic device comprising:
a display portion comprising the light-emitting device according to claim 6; and
any one of an antenna, a battery, a housing, a speaker, a microphone, and an operation key.

8. An organic compound represented by General Formula (G1):

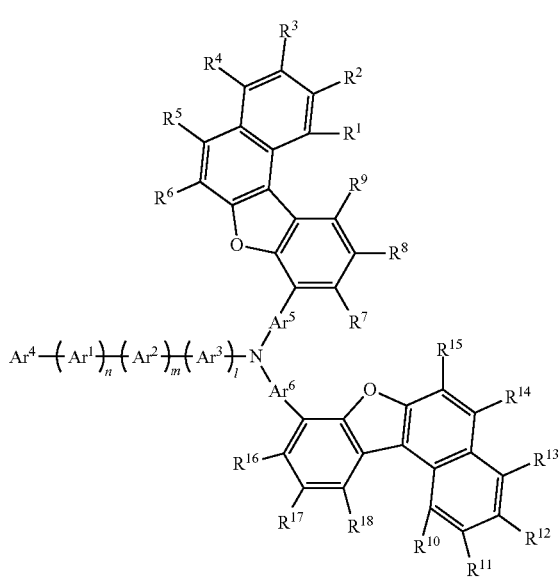

(G1)

wherein $Ar^1$, $Ar^2$, $Ar^3$, $Ar^5$, and $Ar^6$ independently represent a substituted or unsubstituted aromatic hydrocarbon group having 6 to 25 carbon atoms,
wherein $Ar^4$ represents a substituted or unsubstituted aromatic hydrocarbon group having 6 to 25 carbon atoms,
wherein n, m, and l independently represent an integer of 0 or 1,
wherein $R^1$ to $R^{18}$ independently represent any one of hydrogen, a hydrocarbon group having 1 to 6 carbon atoms, a cyclic hydrocarbon group having 3 to 6 carbon atoms, an alkoxy group having 1 to 6 carbon atoms, a cyano group, halogen, a haloalkyl group having 1 to 6 carbon atoms, and a substituted or unsubstituted aromatic hydrocarbon group having 6 to 25 carbon atoms,
wherein $R^6$ and $R^{15}$ independently represent a substituted or unsubstituted aromatic hydrocarbon group having 6 to 13 carbon atoms, and
wherein $R^1$ to $R^5$, $R^7$ to $R^{14}$, and $R^{16}$ to $R^{18}$ represent hydrogen.

9. The organic compound according to claim 8,
wherein $R^1$ to $R^{18}$ independently represent hydrogen or a substituted or unsubstituted aromatic hydrocarbon group having 6 to 13 carbon atoms.

10. The organic compound according to claim 8,
wherein $R^6$ and $R^{15}$ represent a phenyl group.

11. The organic compound according to claim 8,
wherein $Ar^5$ and $Ar^6$ represent phenylene.

12. The organic compound according to claim 8,
wherein $Ar^1$, $Ar^2$, and $Ar^3$ represent phenylene, and
wherein $Ar^5$ and $Ar^6$ represent para-phenylene.

13. A light-emitting element comprising:
an anode;
a cathode; and
an electroluminescent layer,
wherein the electroluminescent layer is between the anode and the cathode, and
wherein the electroluminescent layer comprises the organic compound according to claim 8.

14. A light-emitting device comprising:
a light-emitting portion comprising the light-emitting element according to claim 13; and
a substrate.

15. An electronic device comprising:
a display portion comprising the light-emitting device according to claim 14; and
any one of an antenna, a battery, a housing, a speaker, a microphone, and an operation key.

* * * * *